(12) United States Patent
Eggers et al.

(10) Patent No.: US 6,277,083 B1
(45) Date of Patent: Aug. 21, 2001

(54) MINIMALLY INVASIVE INTACT RECOVERY OF TISSUE

(75) Inventors: Philip E. Eggers, Dublin; Eric A. Eggers, Columbus; Andrew R. Eggers, Ostrander, all of OH (US)

(73) Assignee: Neothermia Corporation, Dublin, OH (US)

( * ) Notice: Subject to any disclaimer, the term of this patent is extended or adjusted under 35 U.S.C. 154(b) by 0 days.

(21) Appl. No.: 09/472,673

(22) Filed: Dec. 27, 1999

(51) Int. Cl.[7] ........................................... A61B 5/00
(52) U.S. Cl. .................................................. 600/564
(58) Field of Search ................... 600/564–567; 606/45–50

(56) References Cited

U.S. PATENT DOCUMENTS

| 3,910,279 | 10/1975 | Okada . |
| 3,955,578 | 5/1976 | Chamness . |

(List continued on next page.)

FOREIGN PATENT DOCUMENTS

| 195 28 440 A1 | 2/1997 | (DE) . |
| 0 829 232 A2 | 3/1998 | (EP) . |
| 0 829 232 A3 | 3/1998 | (EP) . |
| 0 841 036 | 5/1998 | (EP) . |

(List continued on next page.)

OTHER PUBLICATIONS

Atkins, Hedley. *The Treatment of Breast Cancer.* Baltimore: University Park Press. 1974.58–59.

Cardenosa, Gilda. *Breast Imaging Companion.* Philadelphia: Lippincott–Raven Publishers. 1997. 308–310, 386–387, 391, 395–396.

(List continued on next page.)

*Primary Examiner*—Max Hindenburg
(74) *Attorney, Agent, or Firm*—Mueller and Smith, LPA

(57) ABSTRACT

System, method and apparatus for carrying out the recovery of an intact volume of tissue wherein a delivery cannula distal end is positioned in confronting adjacency with the volume of tissue to be recovered. An expandable metal capture component is expressed from the distal end of the cannula to expand while being electrically excited to electrosurgically cut around and circumscribe the tissue volume. Pursing cables are tensioned to complete the envelopment of the tissue volume, whereupon the volume is recovered by withdrawal of the instrument.

86 Claims, 42 Drawing Sheets

U.S. PATENT DOCUMENTS

| | | |
|---|---|---|
| 4,418,692 * | 12/1983 | Guay .................................... 606/45 |
| 4,611,594 | 9/1986 | Grayhack . |
| 4,638,802 | 1/1987 | Okada . |
| 4,997,435 | 3/1991 | Demeter . |
| 5,026,371 | 6/1991 | Rydell et al. . |
| 5,064,428 | 11/1991 | Cope . |
| 5,078,716 | 1/1992 | Doll . |
| 5,083,570 | 1/1992 | Mosby . |
| 5,100,423 * | 3/1992 | Fearnot ................................ 606/45 |
| 5,111,828 | 5/1992 | Kornberg . |
| 5,183,464 | 2/1993 | Dubrul . |
| 5,192,286 | 3/1993 | Phan . |
| 5,197,484 | 3/1993 | Kornberg . |
| 5,217,458 | 6/1993 | Parins . |
| 5,275,611 | 1/1994 | Behl . |
| 5,279,539 | 1/1994 | Bohan et al. . |
| 5,300,070 | 4/1994 | Gentelia . |
| 5,312,360 | 5/1994 | Behl . |
| 5,324,288 | 6/1994 | Billings . |
| 5,336,227 | 8/1994 | Nakao . |
| 5,353,804 | 10/1994 | Kornberg . |
| 5,370,647 | 12/1994 | Graber . |
| 5,397,320 | 3/1995 | Essig . |
| 5,415,656 | 5/1995 | Tihon . |
| 5,417,687 * | 5/1995 | Nardella et al. ...................... 606/45 |
| 5,417,697 | 5/1995 | Wilk . |
| 5,423,809 | 6/1995 | Klicek . |
| 5,423,830 | 6/1995 | Schneebaum . |
| 5,431,676 | 7/1995 | Dubrul . |
| 5,437,665 | 8/1995 | Munro . |
| 5,445,142 | 8/1995 | Hassler . |
| 5,454,790 | 10/1995 | Dubrul . |
| 5,465,731 | 11/1995 | Bell . |
| 5,486,182 | 1/1996 | Nakao . |
| 5,499,989 | 3/1996 | LaBash . |
| 5,514,153 | 5/1996 | Bonutti . |
| 5,599,348 | 2/1997 | Gentelia . |
| 5,626,578 | 5/1997 | Tihon . |
| 5,630,822 | 5/1997 | Hermann . |
| 5,643,282 | 7/1997 | Kieturakis . |
| 5,647,372 | 7/1997 | Tovey . |
| 5,658,279 | 8/1997 | Nardella . |
| 5,674,184 | 10/1997 | Hassler . |
| 5,709,697 | 1/1998 | Ratcliff . |
| 5,741,271 | 4/1998 | Nakao . |
| 5,746,740 | 5/1998 | Nicholas . |
| 5,749,870 | 5/1998 | Gloth et al. . |
| 5,749,889 | 5/1998 | Bacich . |
| 5,759,187 | 6/1998 | Nakao . |
| 5,779,715 | 7/1998 | Tu . |
| 5,782,840 | 7/1998 | Nakao . |
| 5,794,626 | 8/1998 | Kieturakis . |
| 5,795,308 | 8/1998 | Russin . |
| 5,797,907 | 8/1998 | Clement . |
| 5,807,276 | 9/1998 | Russin . |
| 5,810,806 | 9/1998 | Ritchart . |
| 5,814,052 | 9/1998 | Nakao . |
| 5,824,002 | 10/1998 | Gentelia . |
| 5,846,248 | 12/1998 | Chu . |
| 5,848,978 | 12/1998 | Cecchi . |
| 5,857,982 | 11/1999 | Millman . |
| 5,882,316 | 3/1999 | Chu . |
| 5,904,679 | 5/1999 | Clayman . |
| 5,913,857 | 7/1999 | Ritchart . |
| 5,925,044 | 6/1999 | Hofman . |
| 5,928,163 | 7/1999 | Roberts . |
| 5,957,923 | 9/1999 | Hahnen . |
| 5,968,056 | 10/1999 | Chu . |
| 5,980,515 | 12/1999 | Tu . |
| 5,997,547 | 11/1999 | Nakao . |
| 6,013,086 | 1/2000 | Ouchi . |
| 6,019,720 | 2/2000 | Bito . |
| 6,019,758 | 2/2000 | Slater . |
| 6,022,362 | 2/2000 | Lee . |
| 6,027,508 | 2/2000 | Ren . |
| 6,030,365 | 2/2000 | Laufer . |
| 6,030,403 | 2/2000 | Long . |
| 6,033,402 | 3/2000 | Tu . |
| 6,036,698 | 3/2000 | Fawzi . |
| 6,036,708 | 3/2000 | Van Sciver . |

FOREIGN PATENT DOCUMENTS

| | | |
|---|---|---|
| 2275226 | 1/1976 | (FR) . |
| 2311468 | 1/1997 | (GB) . |
| 1004723 | 8/1998 | (NL) . |
| 8206417-1 | 11/1982 | (SE) . |
| 1355266 | 6/1986 | (SU) . |
| 1235497 | 11/1987 | (SU) . |
| WO 95/02370 | 1/1995 | (WO) . |
| WO 95/02371 | 1/1995 | (WO) . |
| WO 97/42991 | 11/1997 | (WO) . |
| WO 97/43958 | 11/1997 | (WO) . |
| WO 98/08441 | 2/1998 | (WO) . |
| WO 98/06448 | 3/1998 | (WO) . |
| WO 9904704 | 2/1999 | (WO) . |
| WO 99/39648 | 8/1999 | (WO) . |
| WO 99/44506 | 9/1999 | (WO) . |
| WO 99/52441 | 10/1999 | (WO) . |
| WO 99/53851 | 10/1999 | (WO) . |

OTHER PUBLICATIONS

Chung, Y, et al., "Generation and Observation of Radio Frequency Thermal Lesion Ablation for Interventional Magnetic Resonance Imaging." *Invest Radiol* 1997; 32: 466–474.

D'Angelo, Philip C., et al. "Stereotactic Excisional Breast Biopsies Utilizing the Advanced Breast Biopsy Instrumentation System." *Am J Surg.* 1997; 174: 297–302.

Daniel, BL, et al. "Breast Lesion Localization: A Freehand, Interactive MR Imaging–Guided Technique." *Radiology* 1998: 207: 455–463.

Ferzli, George S., et al. "Advanced Breast Biopsy Instsrumentation: A Critique." *J Am Coll Surg* 1997; 185: 145–151.

Fornage, BD. "Guided Needle Biopsy of Nonpalpable Breasr Masses." *Mastology—Breast Diseases.* Eds. A.S.S. Figueira Fo., et al. Amsterdam: Elsevier, 1995. 96–107.

Fornage, BD. "Percutaneous Needle Biopsy of the Breast." *Mastology—Breast Diseases.* Eds. A.S.S. Figueira Fo., et al. Amsterdam: Elsevier, 1995. 90–95.

Gorczyca, DP., et al. "Wire Localization of Breast Lesions Before Biopsy: Use of an MR–Compatible Device in Phantoms and Cadavers." *AJR* 1995; 165: 835–838.

Harris, Jay R., et al. "Cancer of the Breast." *Cancer: Principles and Practices of Oncology, Fourth Edition.* Eds. DeVita, et al. Philadelphia: J.B. Lippincott Co., 1993. 1264–1285.

Hendrick, RE., et al. "Principles of Stereotactic Mamm0ography and Quality Assurance." *Percutaneous Breast Biopsy.* Eds. Parker, et al. New York: Raven Press, 1993. 49–59.

Heywang–Kobrunner, SH, et al. "New Methods for Minimally Invasive Clarification of Uncertain Mannographic and MR Tomographic Results." *Zentralbl. Chir.* 1998; 123 (Supp 5): 66–69.

Jellins, J. "Current Concepts in Breast Ultrasound: Developments in Technology and Quality Assurance." *Mastology—Breast Diseases*. . Eds. A.S.S. Figueira Fo., et al. Amsterdam: Elsevier, 1995. 79–83.

Jobe, William E. "Historical Perspectives." *Percutaneous Breast Biopsy*. Eds. Parker, et al. New York: Raven Press, 1993. 1–5.

Kahn, T., et al. "In Vivo MRI Thermometry Using a Phase-Sensitive Sequence: Preliminary Experience During MRI–Guided Laser–Induced Interstitial Thermotherapy of Brain Tumors." *JMRI* 1998; 8: 160–164.

Kelley, WE., et al. "Advanced Breast Biopsy Instumentation." *J Am Coll Surg* 1997; 604–605.

Kuhl, CK, et al. "Interventional Breast MR Imaging: Clinical Use of a Stereotactic Localization and Biopsy Device." *Radiology* 1997; 204: 667–675.

Matthews, BD. "Initial Experience with the Advanced Breast Biopsy Instrumentation System." *Am J Surg.* 1999; 177: 97–101.

Parker, Steve H. "The Advanced Breast Biopsy Instrumentation: Another Trojan Hourse?" *AJR* 1998; 171: 51–53.

Parker, Steve H. "Needle Selection." *Percutaneous Breast Biopsy*. Eds. Parker, et al. New York: Raven Press, 1993. 7–14.

Parker, Steve H. "Stereotactic Large–Core Breast Biopsy." *Percutaneous Breast Biopsy*. Eds. Parker, et al. New York: Raven Press, 1993. 61–79.

Rosen, Paul Peter. *Rosen's Breast Pathology*. Philadelphia: Lippincott–Raven Publishers, 1997. 837–858.

Stavros, AT, et al. "An Introduction to Breast Ultrasound." *Percutaneous Breast Biopsy*. Eds. Parker, et al. New York: Raven Press, 1993. 95–109.

Truell, JE., et al. "The Pathologist's Perspective." *Percutaneous Breast Biopsy*. Eds. Parker, et al. New York: Raven Press, 1993. 15–23.

Vogl, TJ., et al. "Magnetic Resonance Imaging–Guided Abdominal Interventional Radiology: Laser–Induced Thermotherapy of Liver Metastases." *Endoscopy* 1997; 29: 577–583.

* cited by examiner

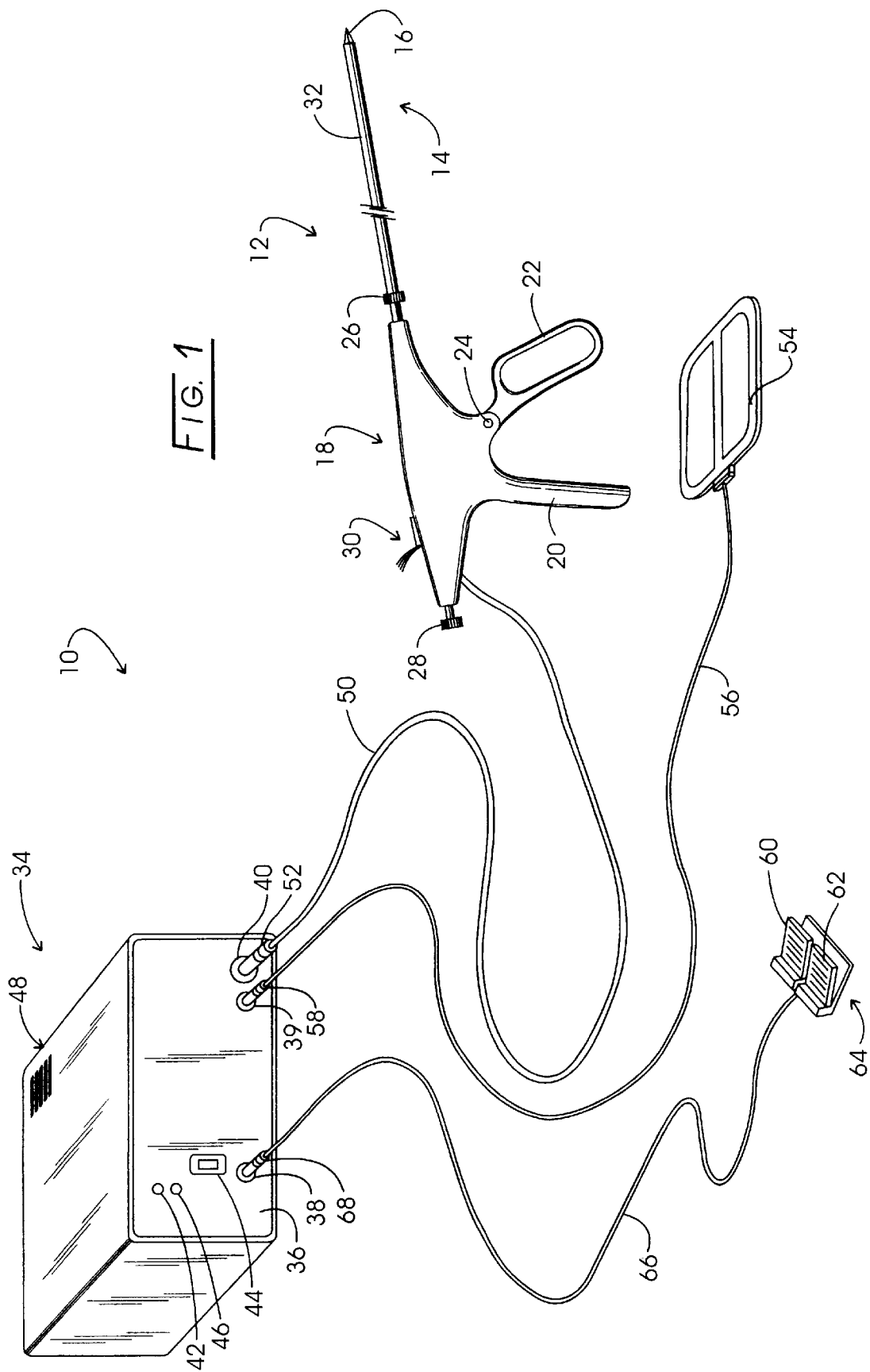

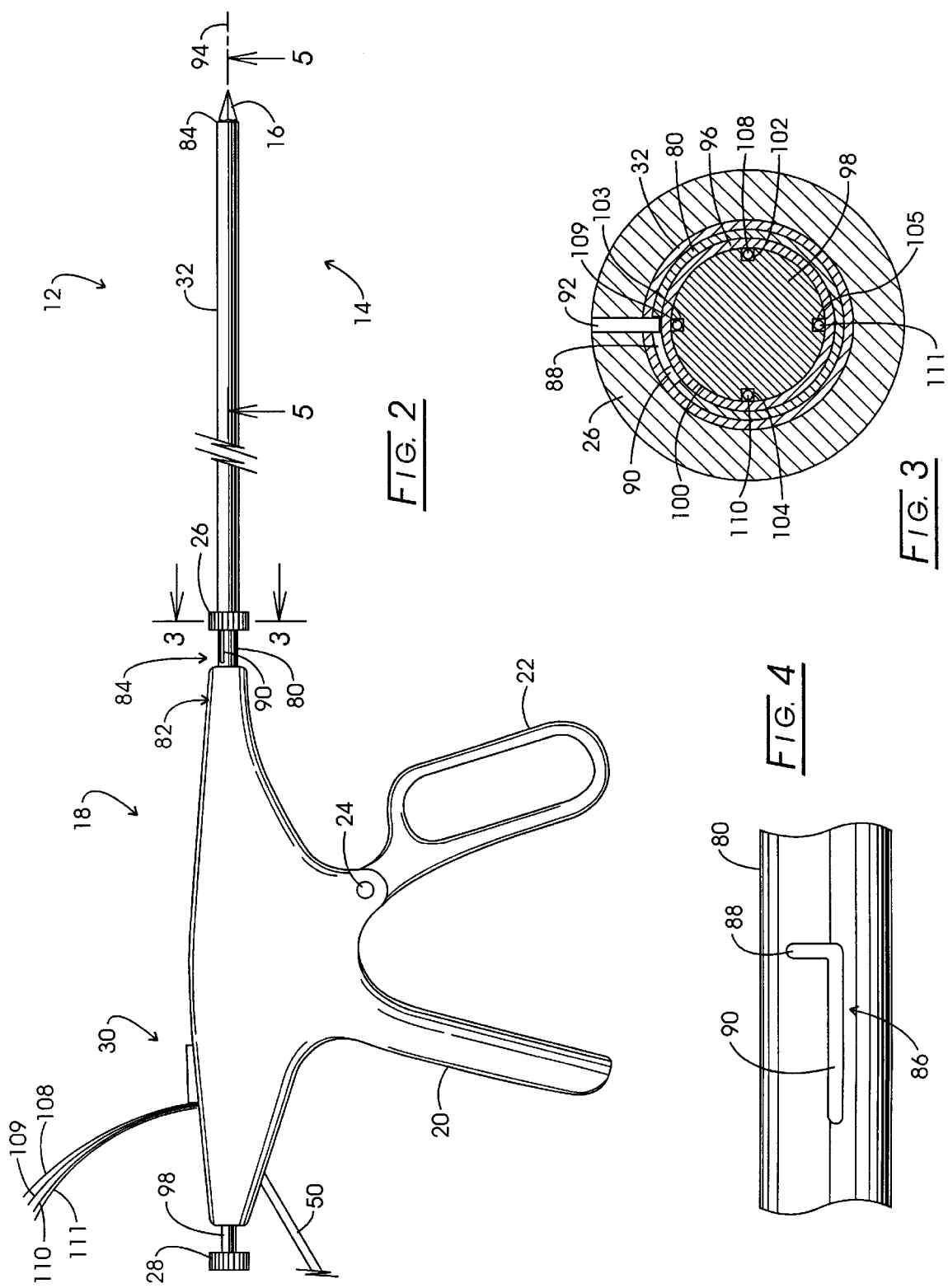

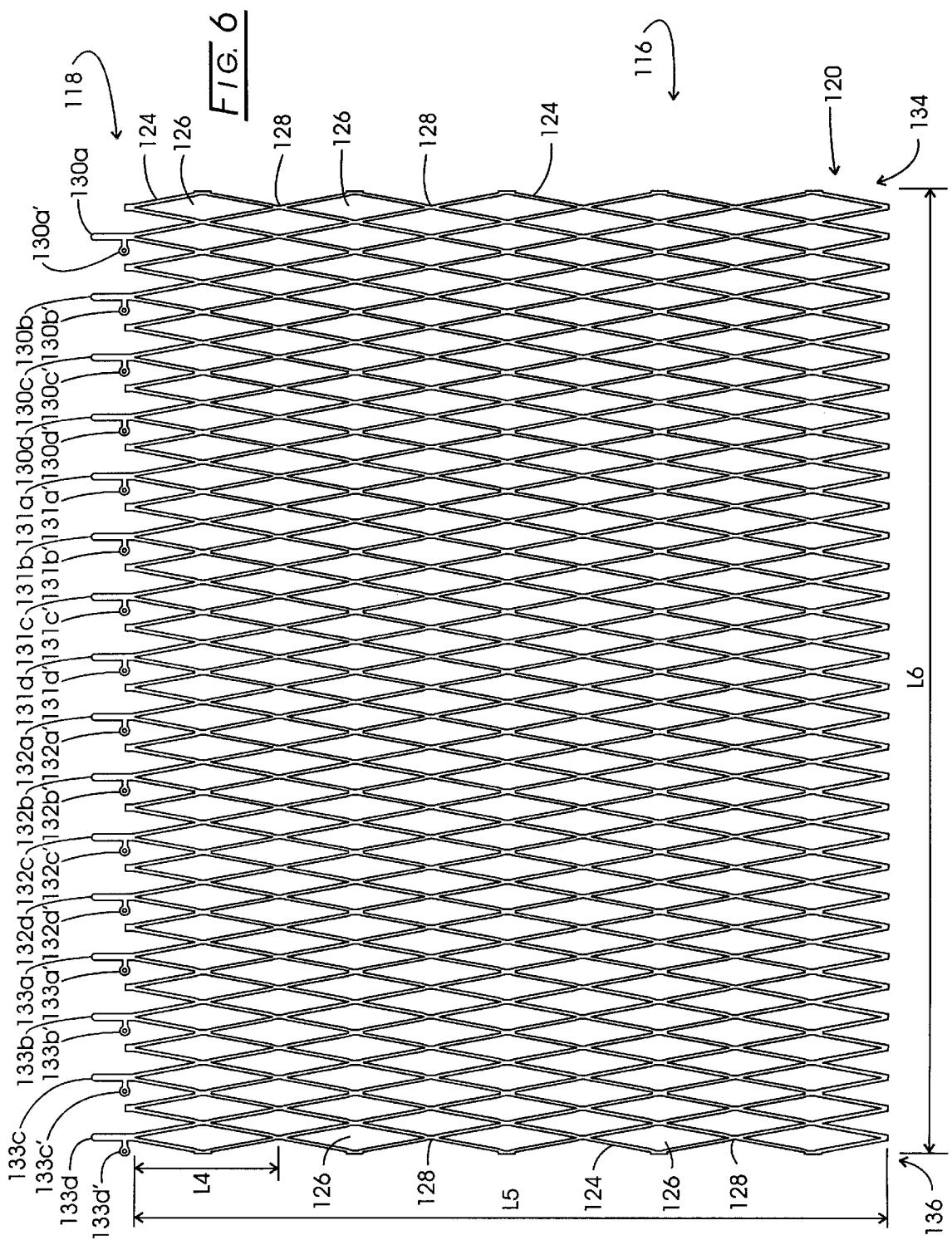

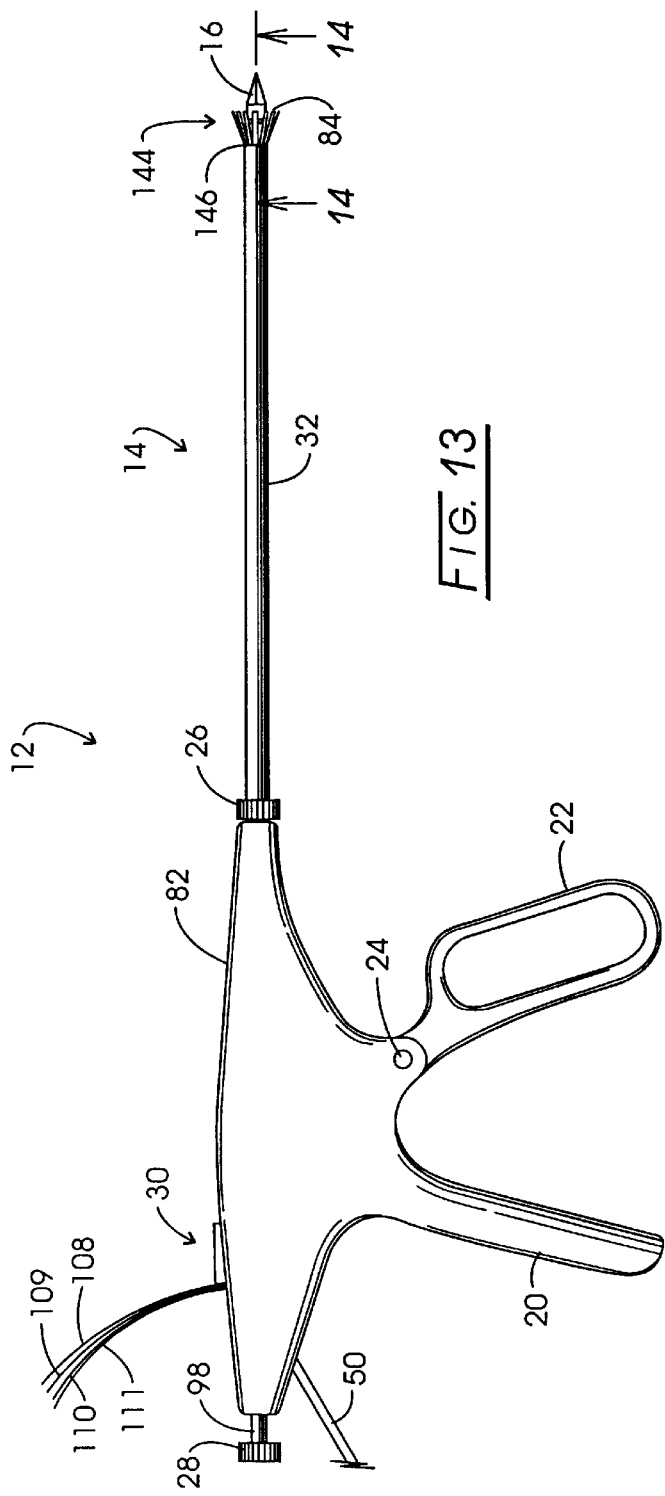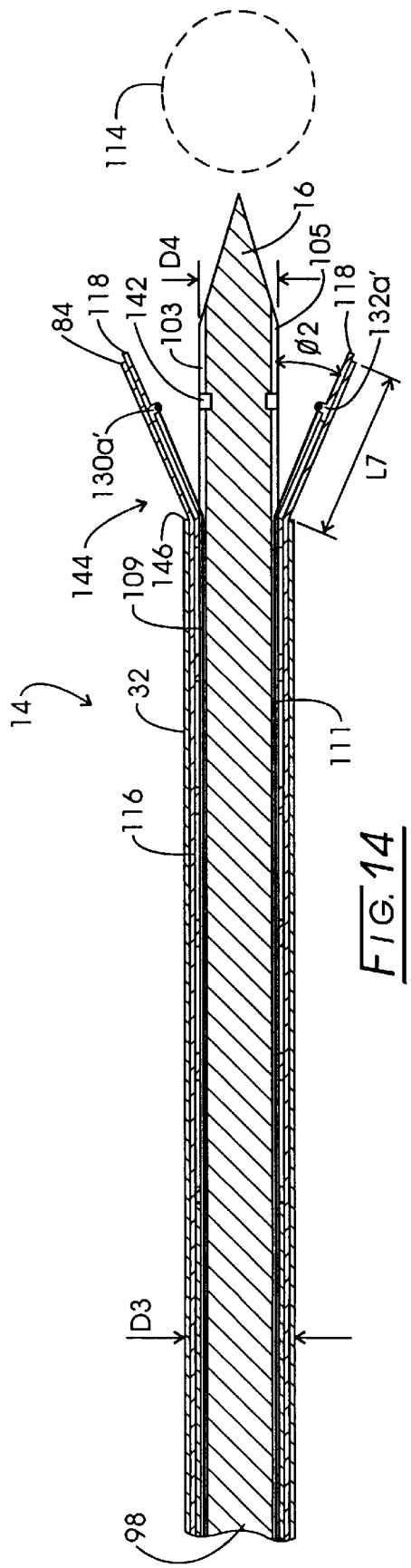
FIG. 13
FIG. 14

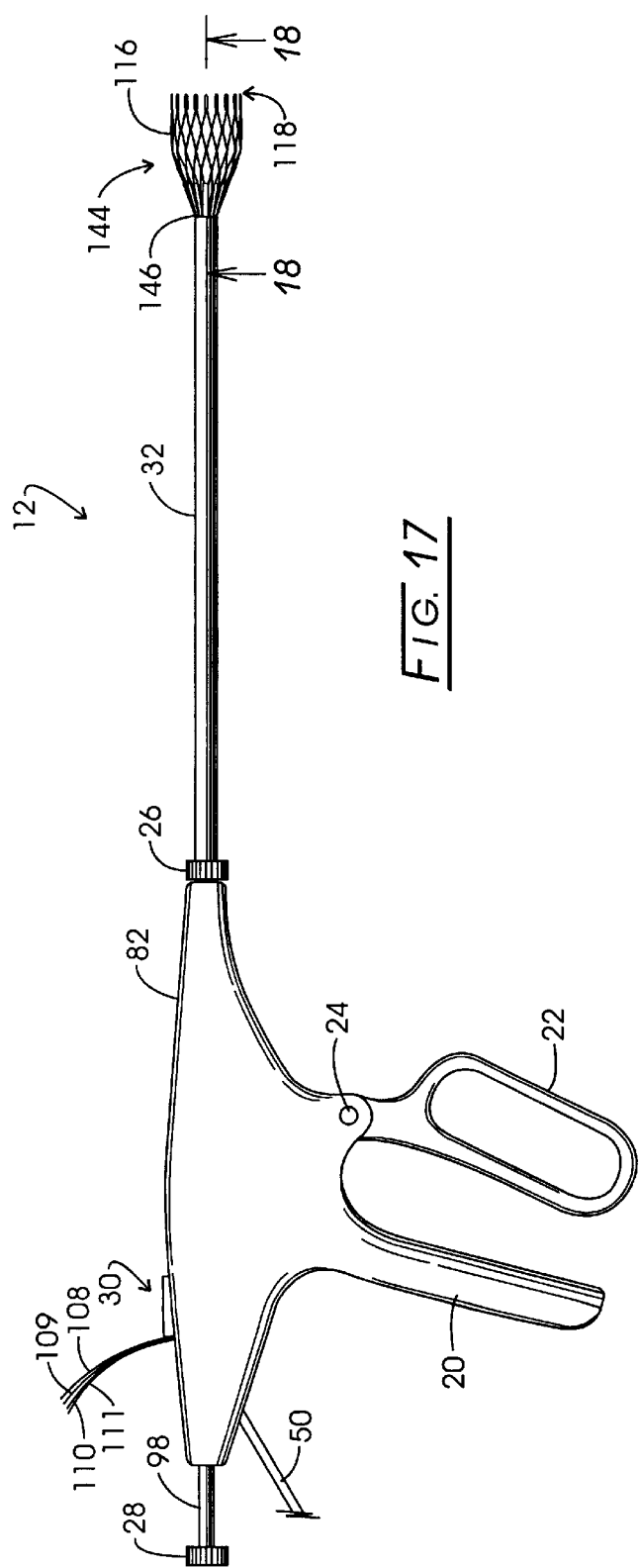
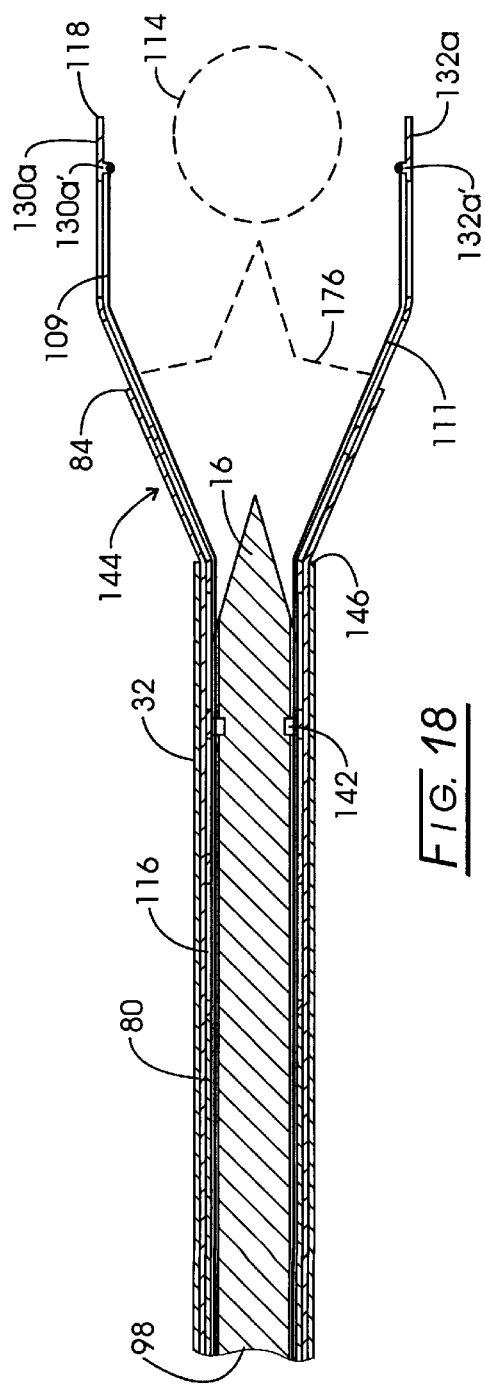
FIG. 17
FIG. 18

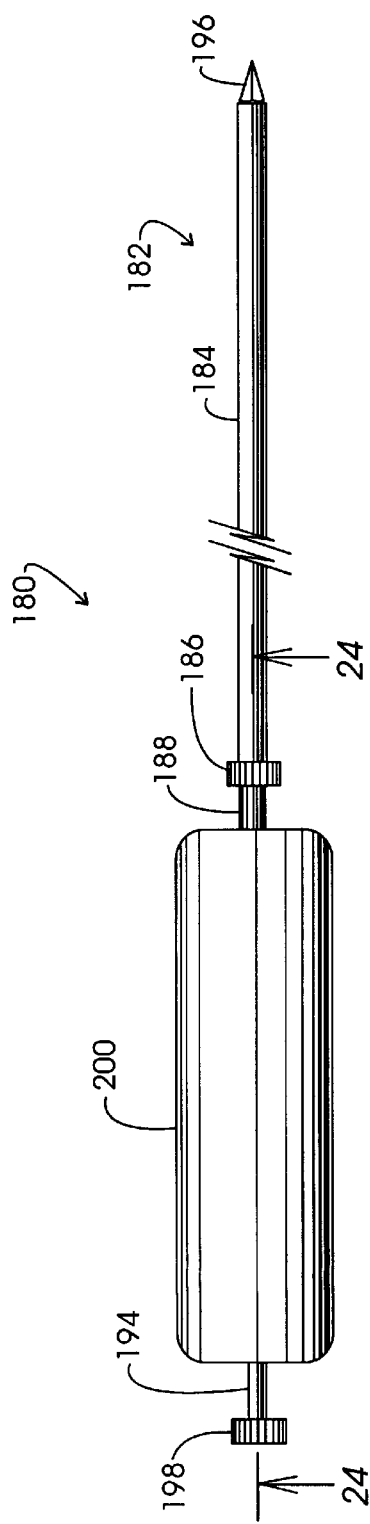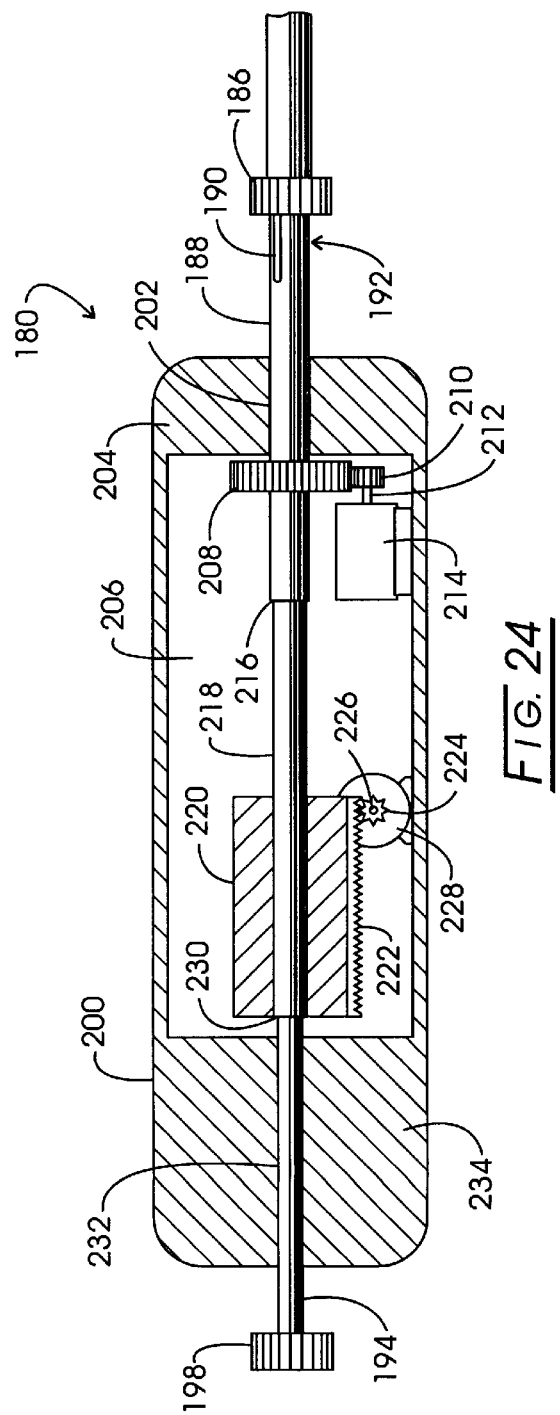

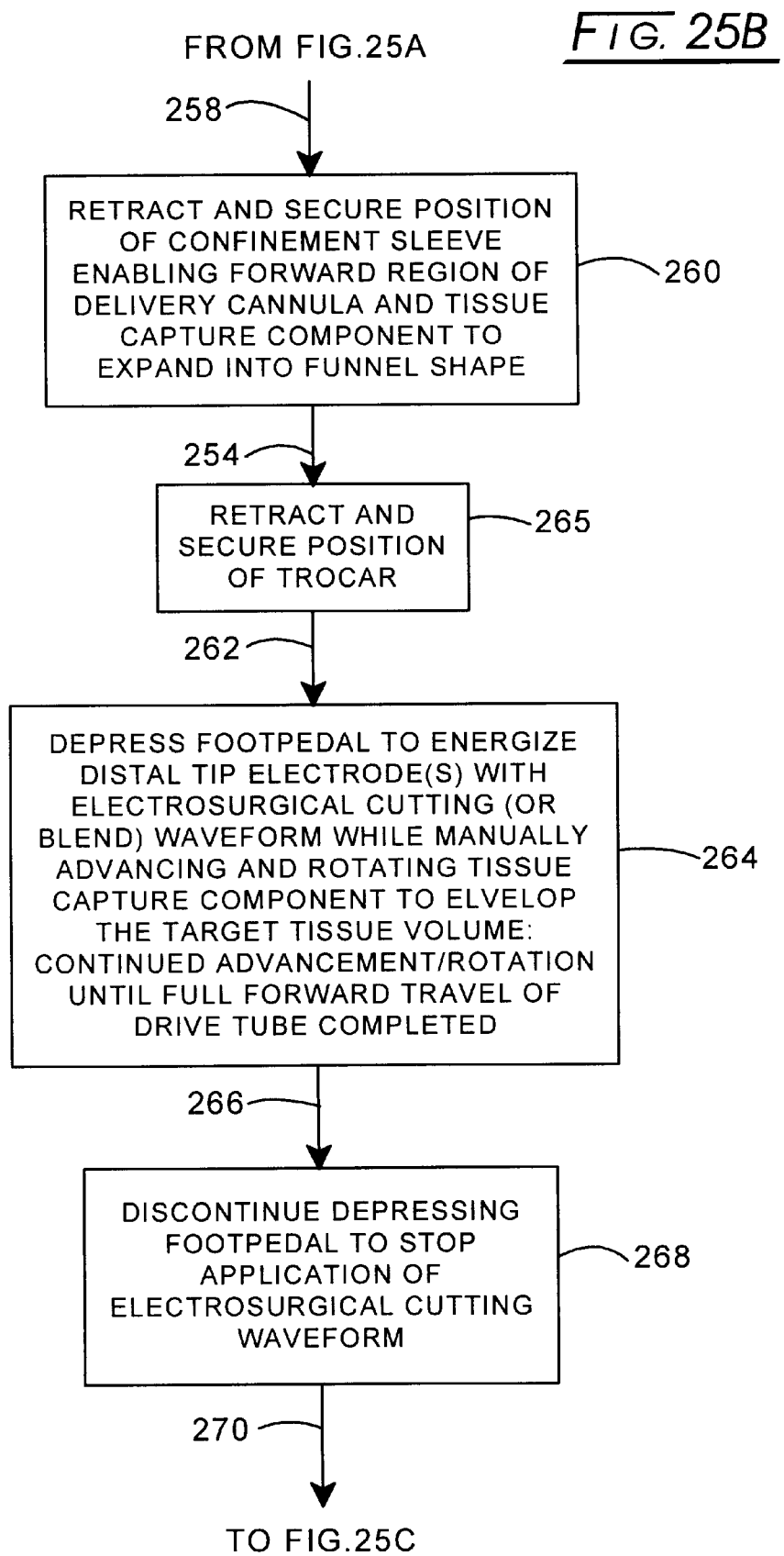

FIG. 25C

FROM FIG.25B

270

272 — OPTIONALLY, DEPRESS SWITCH OF CONTROL SYSTEM WHICH FIRST ENERGIZES DISTAL TIP ELECTRODE(S) WITH ELECTROSURGICAL CUTTING (OR BLEND) WAVEFORM WHILE UTILIZING MOTION-CONTROLLED MOTORS TO AUTOMATICALLY ROTATE WHILE EXTENDING TISSUE CAPTURE COMPONENT TO AUTOMATICALLY ENVELOP THE TARGET TISSUE VOLUME; EXTENTION CONTINUED UNTIL FULL FORWARD TRAVEL OF DRIVE TUBE COMPLETED AND ELECTROSURGICAL GENERATOR CUTTING WAVEFORM APPLICATION IS AUTOMATICALLY TERMINATED

274

276 — OPTIONALLY SLIDE DILATOR FORWARD TO RADIALLY EXPAND THE TISSUE WHICH SPANS THE PATHWAY BETWEEN THE CAPTURED TISSUE VOLUME AND THE SURFACE OF THE TISSUE (e.g., SKIN SURFACE)

278

280 — REMOVE TISSUE CAPTURE COMPONENT FROM BODY AND SEVER PURSING CABLE TO EXPEL CAPTURED TARGET TISSUE VOLUME (e.g., FOR SUBSEQUENT PATHOLOGICAL EXAMINATION)

282

END — 284

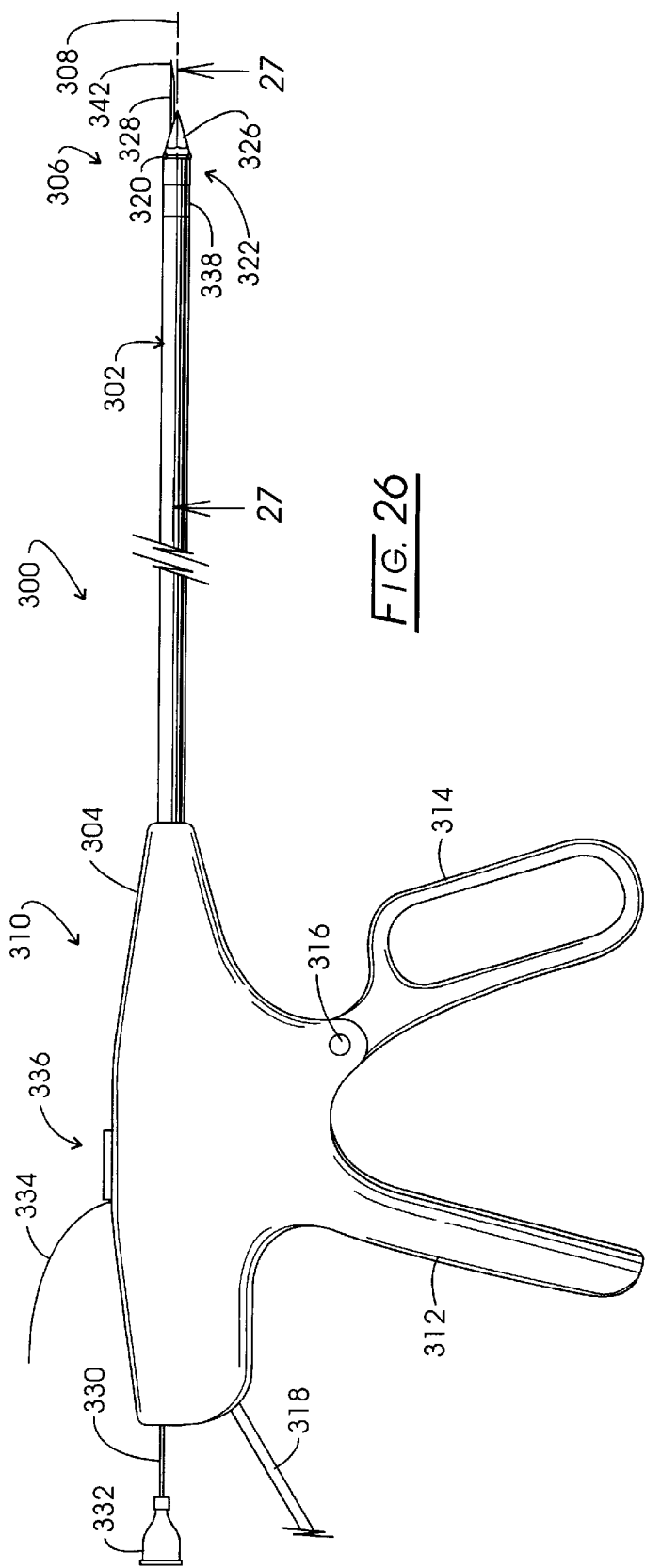
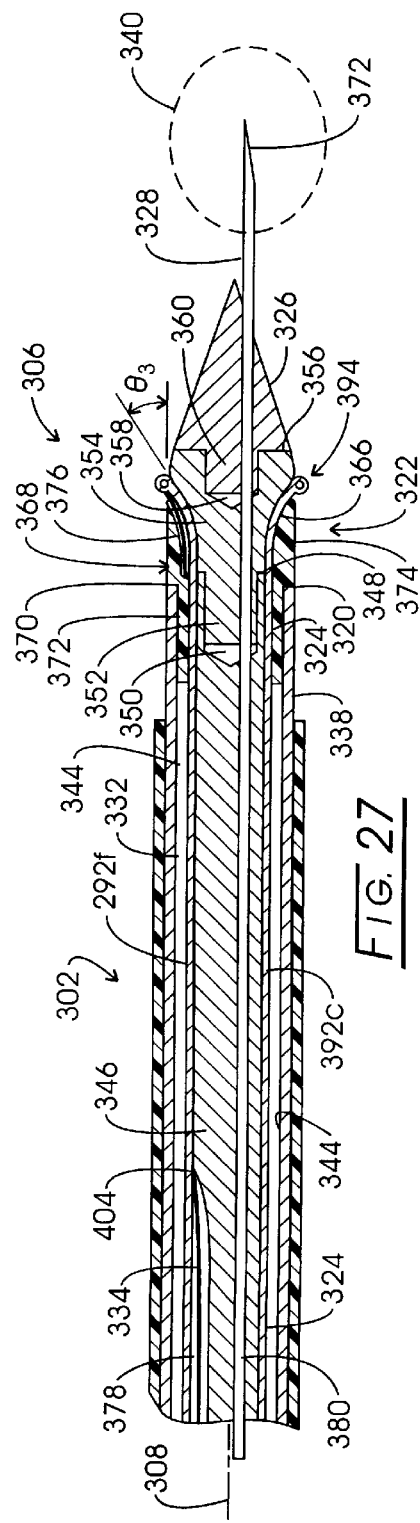
FIG. 26
FIG. 27

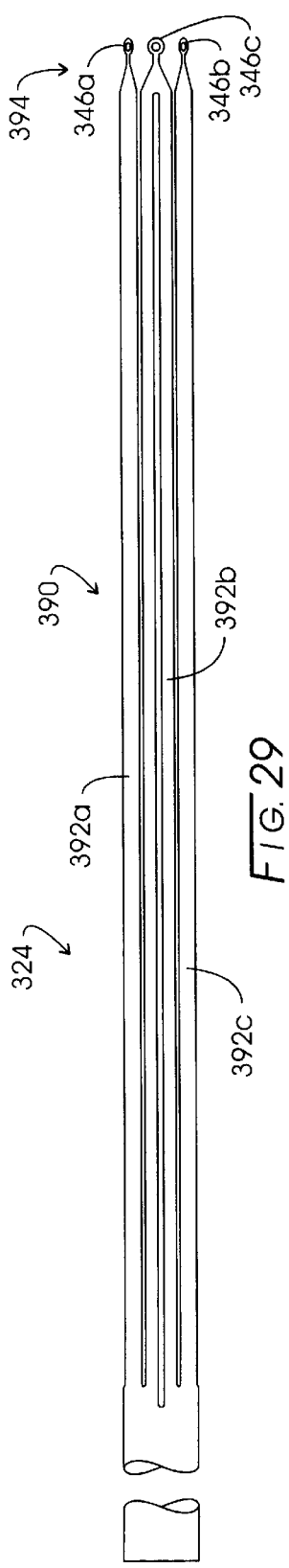
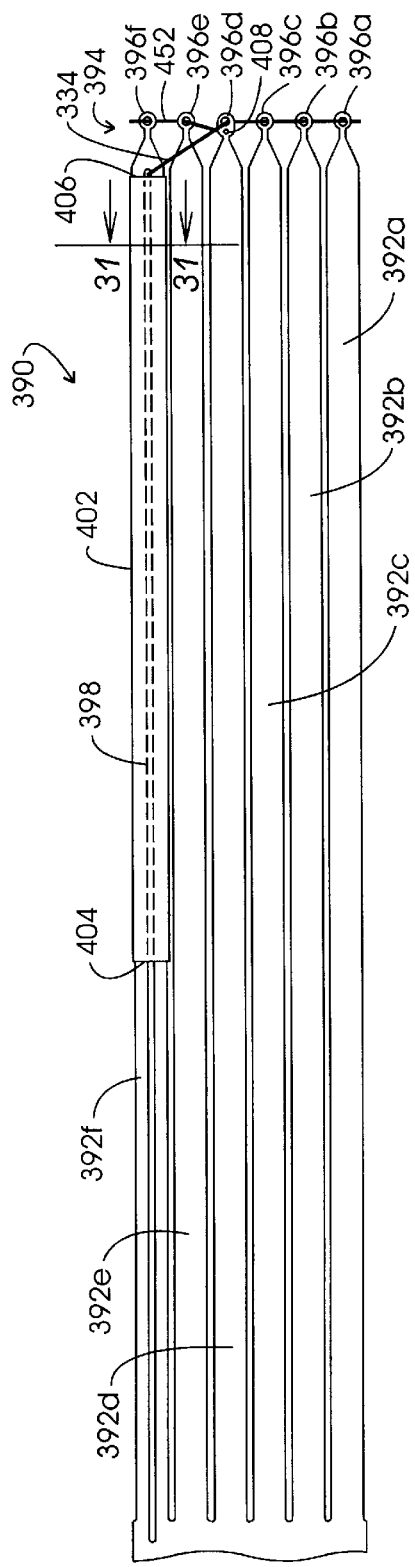
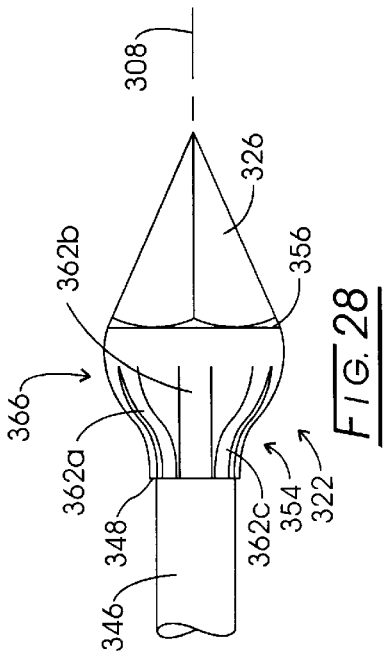
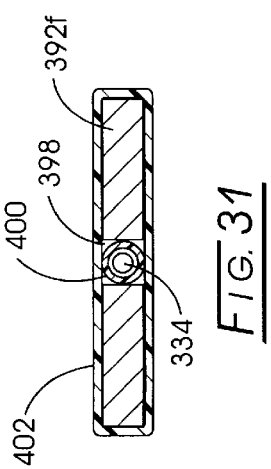
FIG. 29
FIG. 30
FIG. 28
FIG. 31

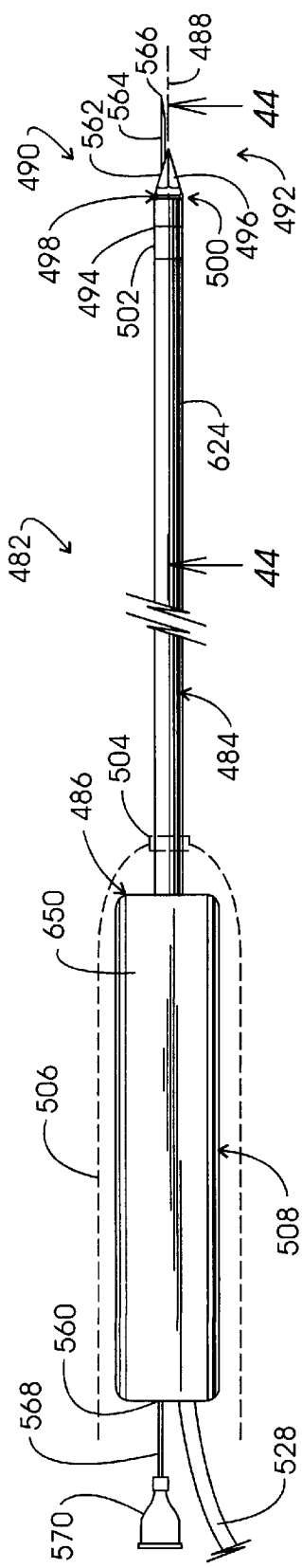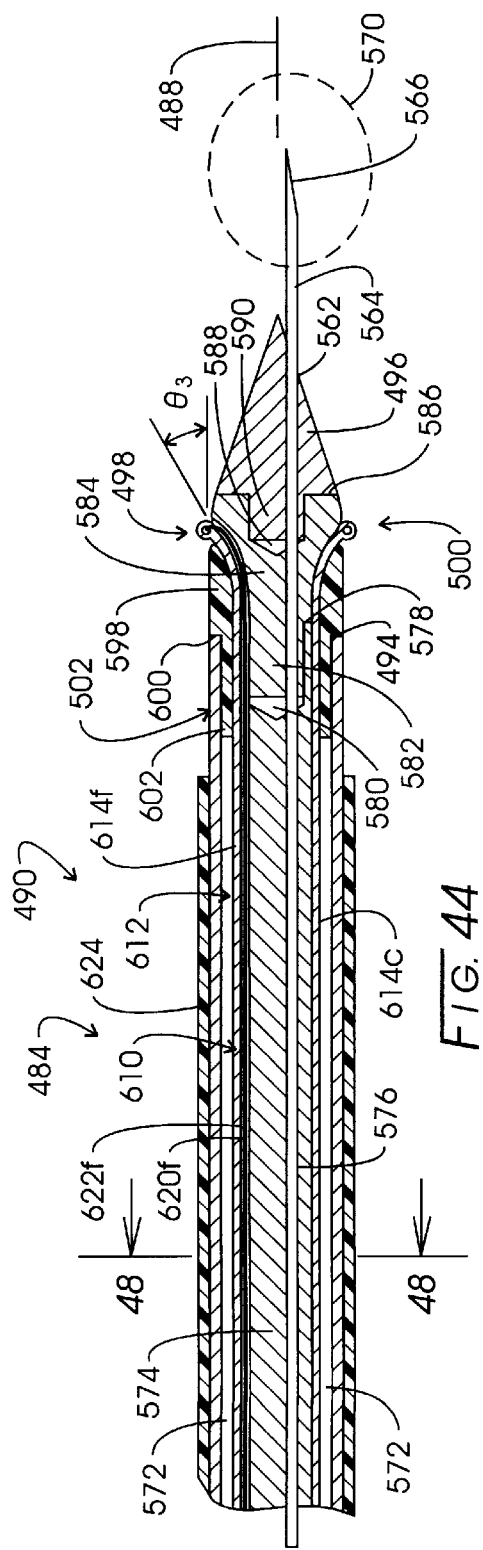

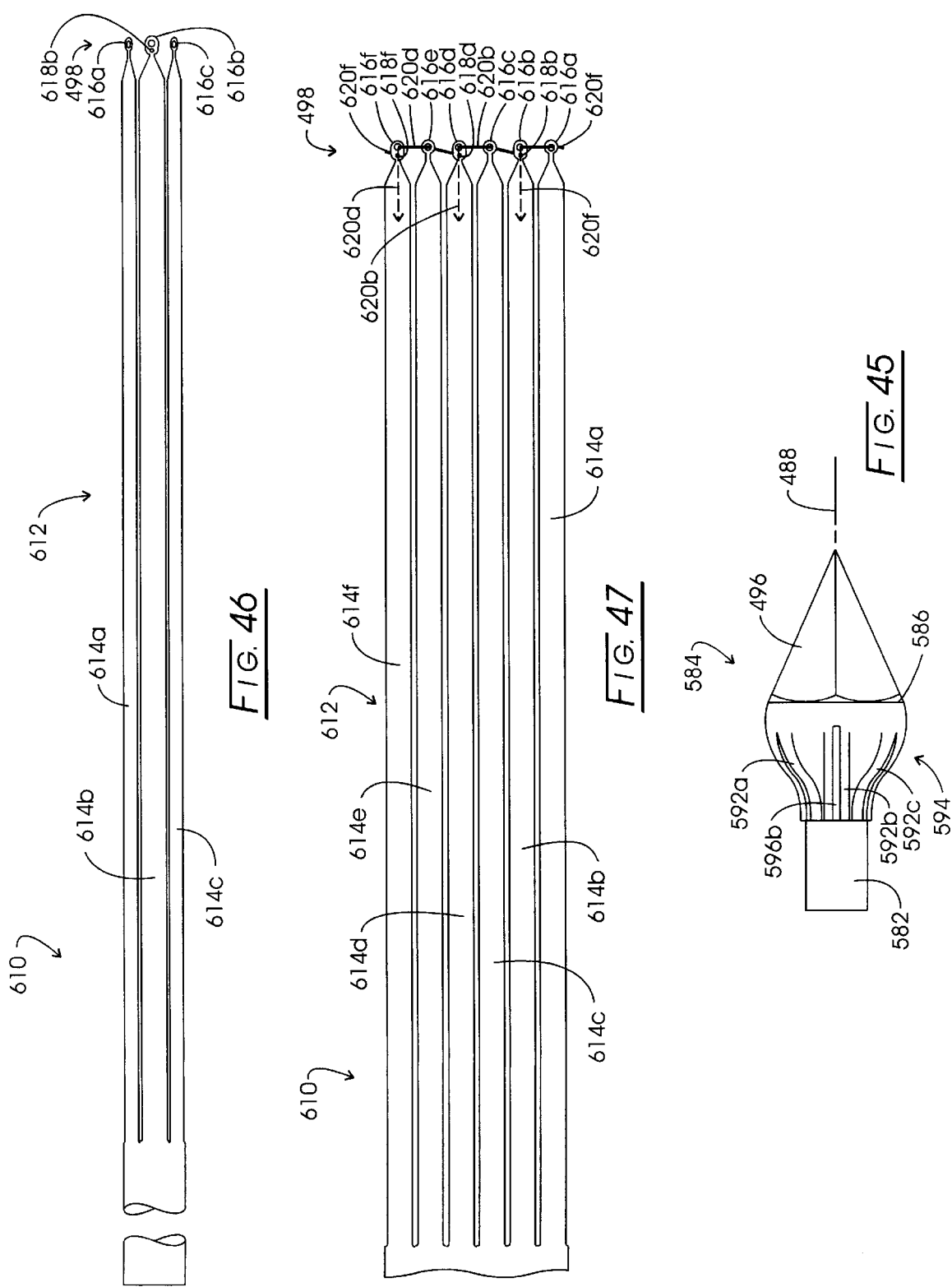

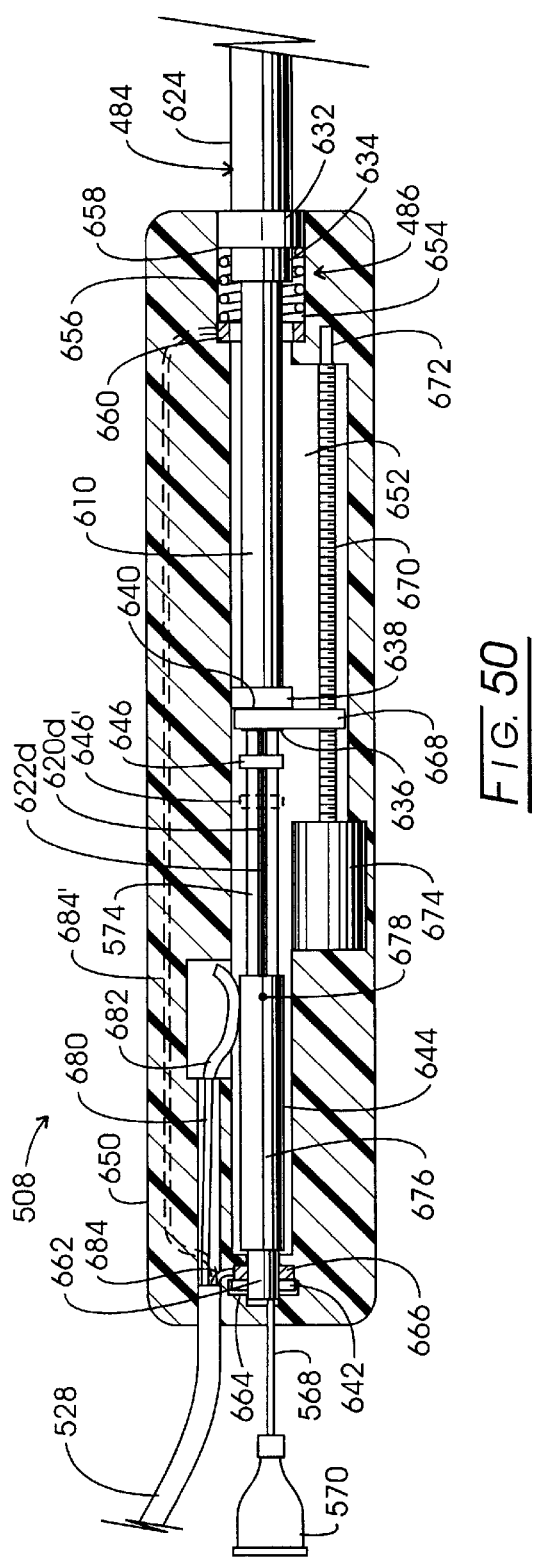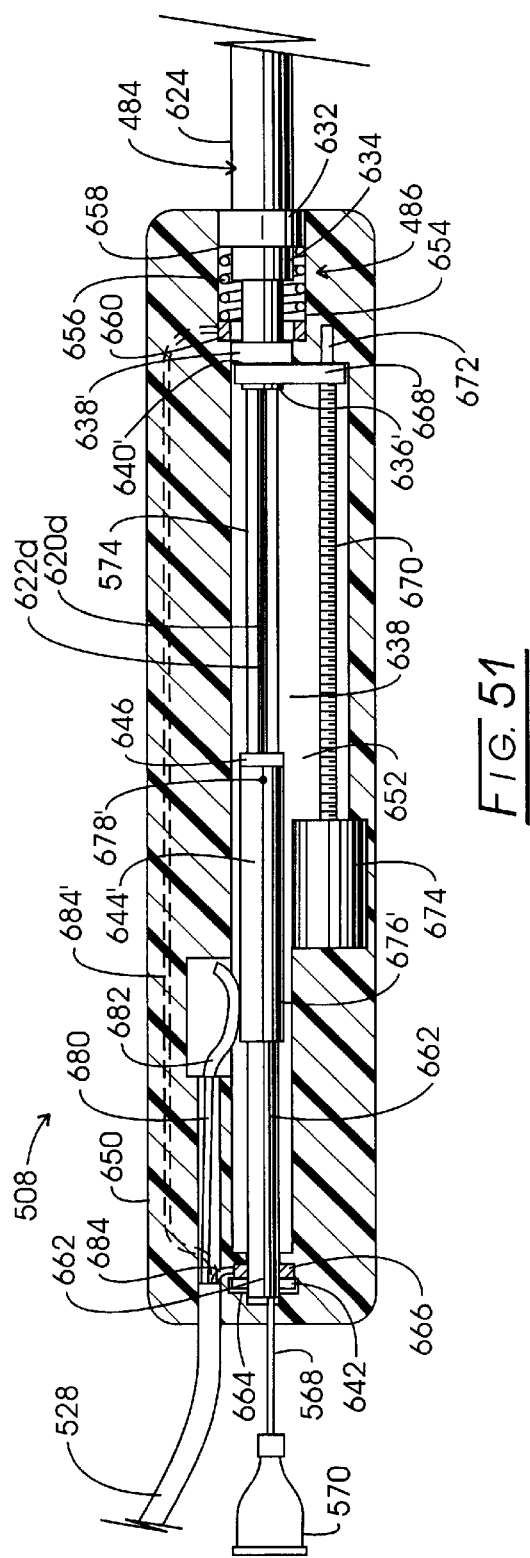

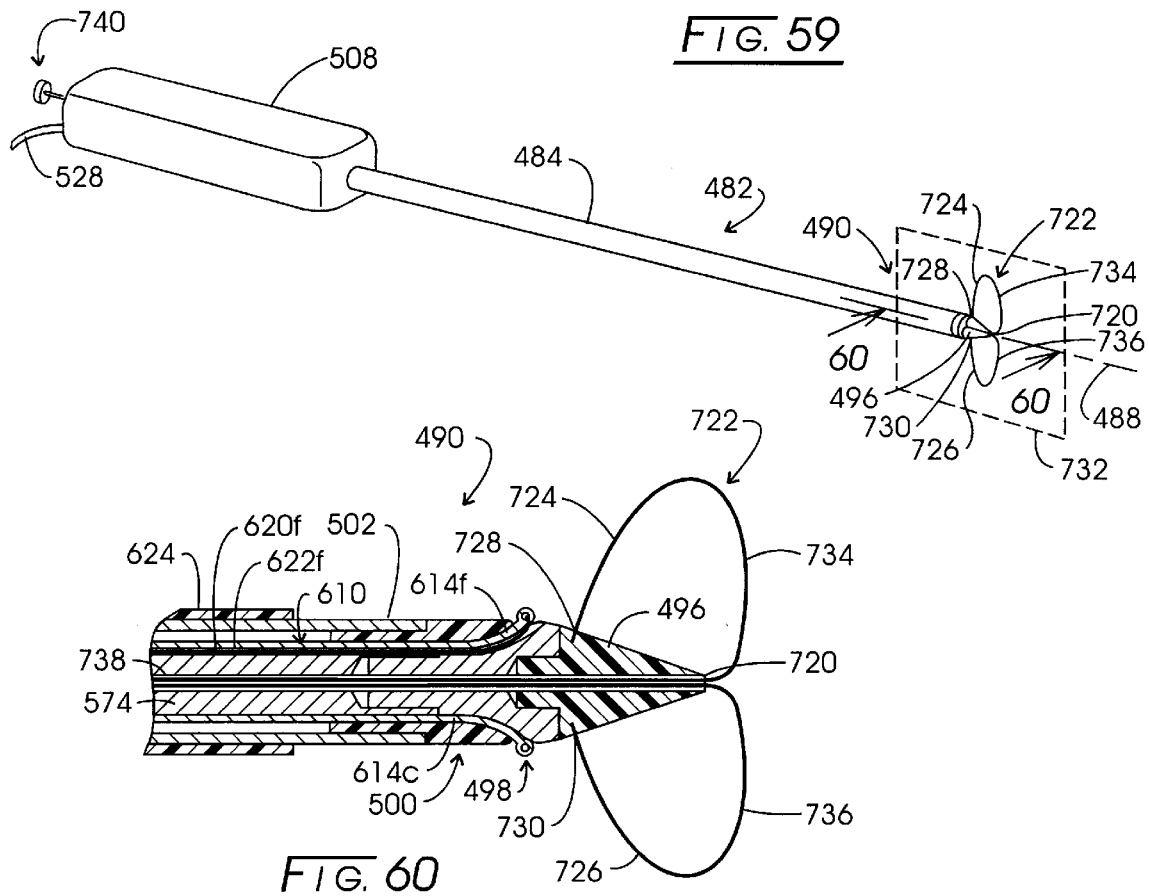
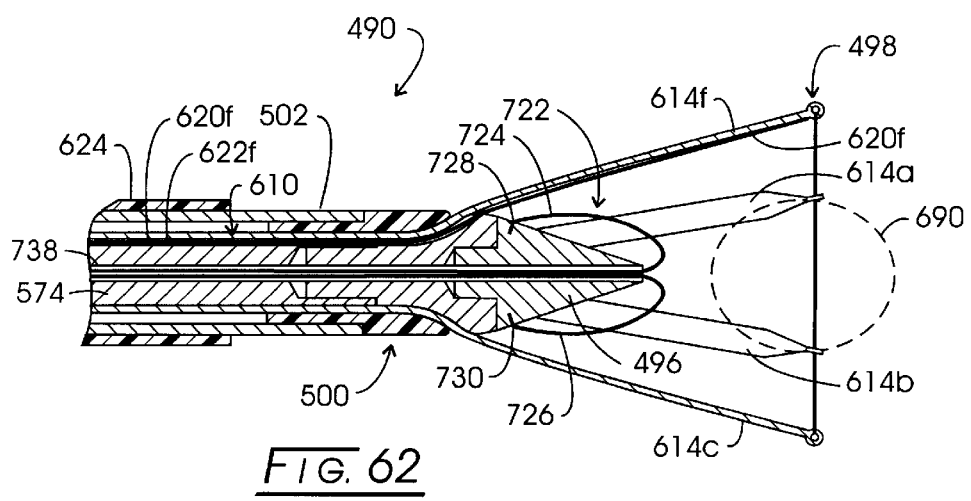

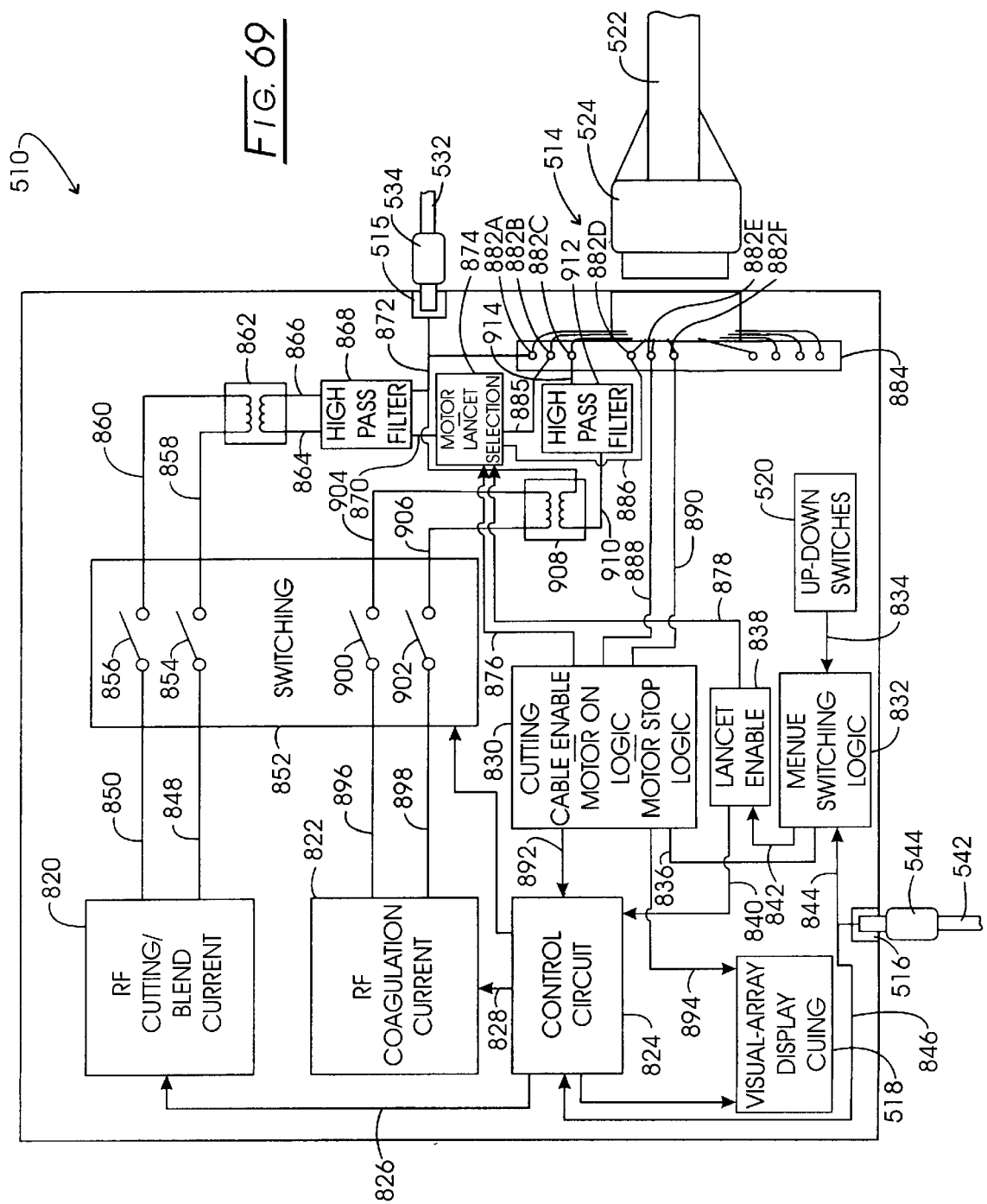

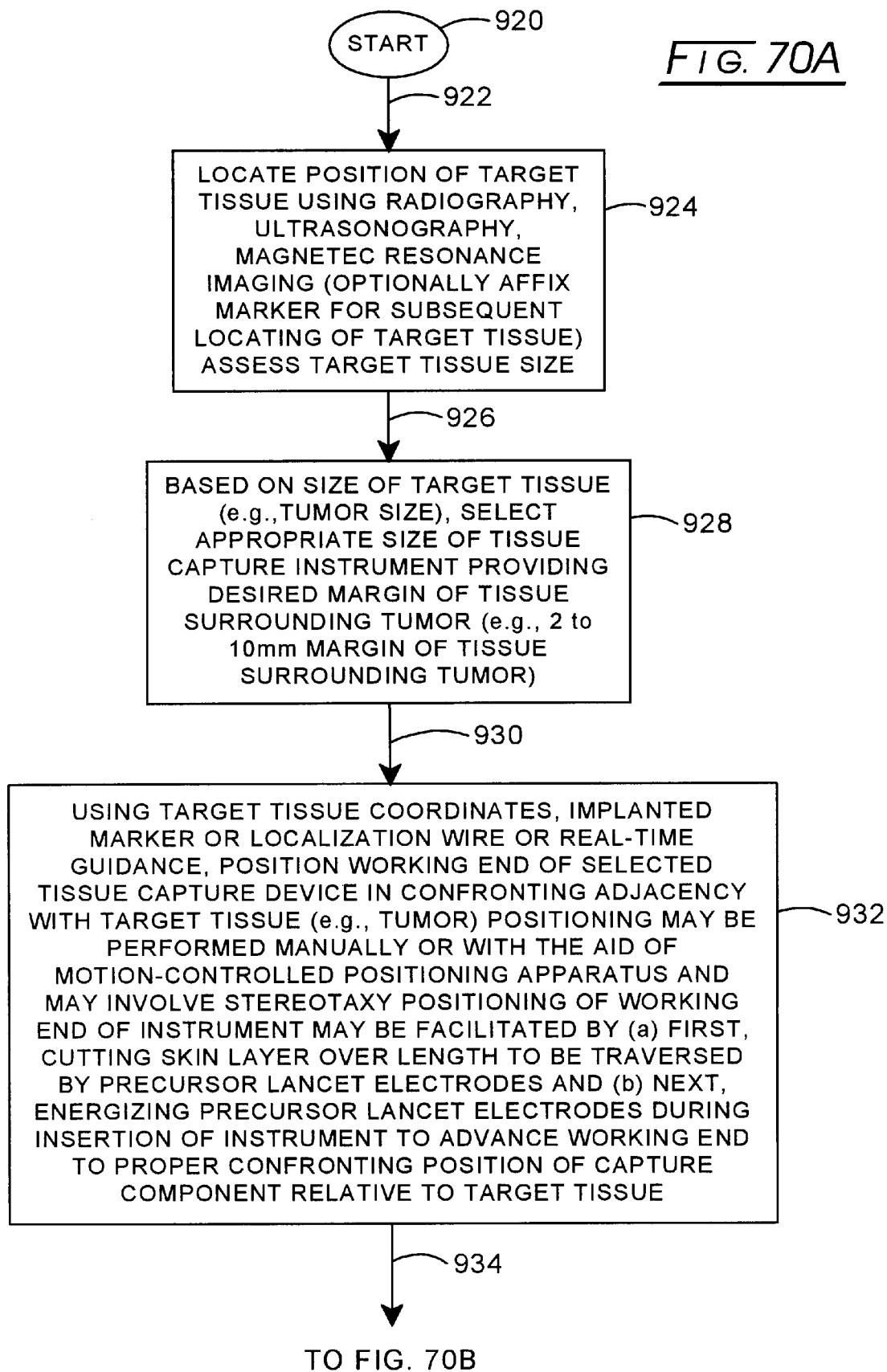

FIG. 70B

FROM FIG. 70A
─ 934

OPTIONALLY, INSERT FNA NEEDLE DOWN AUXILIARY CHANNEL PROVIDED IN INSTUMENT TO EFFECT ASPIRATION OF TISSUE/CELLS FROM TARGET TISSUE PRIOR TO EXCISION OF ENCAPSULATED TISSUE VOLUME ─ 936

─ 938

OPTIONALLY, INSERT PROXIMAL END OF LOCALIZATION WIRE INTO AUXILIARY CHANNEL OF INSTRUMENT TO CONFRONT TARGET TISSUE SITE; MEASURE DISPLACEMENT OF FOLLOWER COMPONENT TO DETERMINE WHEN PRESCRIBED DEPTH OF INSERTION INTO TISSUE HAS BEEN ACHIEVED. ─ 940

─ 942

DEPRESS FOOTPEDAL SWITCH TO ENERGIZE ONE OR MORE CUTTING WIRE ELECTRODE(S) WITH ELECTROSURGIAL CUTTING (OR BLEND) WAVEFORM WHILE MANUALLY ADVANCING TISSUE CUTTING/CAPTURE COMPONENT TO ENVELOP THE MARGIN ISOLATED TARGET TISSUE VOLUME; CONTINUE ADVANCEMENT UNTIL FULL FORWARD TRAVEL OF TISSUE CUTTING/CAPTURE COMPONENT COMPLETE; DURING FORWARD TRAVEL, ONE OR MORE PURSING CABLE(S) BECOME TAUGHT, LEADING EDGE OF TISSUE CUTTING/CAPTURE COMPONENT IS CAUSED TO CLOSE, ACHIEVING COMPLETE CLOSURE OF LEADING EDGE OF TISSUE CUTTING/CAPTURE COMPONENT EFFECTS A COMPLETE SEVERING OF THE ENCALPSULATED TISSUE VOLUME FROM SURROUNDING TISSUE AT LEADING EDGE. ─ 944

─ 946

DISCONTINUE DEPRESSING FOOTPEDAL TO STOP APPLICATION OF ELECTROSURGICAL CURRENT TO CUTTING WIRE ELECTRODE(S). ─ 948

FROM FIG. 70B

952 ↘  ↓ ⎯ 950

OPTIONALLY, DEPRESS SWITCH OF CONTROL SYSTEM WHICH FIRST ENERGIZES ONE OR MORE PURSING CABLE CUTTING WIRE ELECTRODE(S) WITH ELECTROSURGICAL CUTTING (OR BLEND) WAVEFORM WHILE UTILIZING MOTOR DRIVE TO EXTEND TISSUE CUTTING/CAPTURE COMPONENT TO AUTOMATICALLY ENVELOP THE TARGET TISSUE VOLUME: MOTORIZED EXTENTION CONTINUES UNTIL FULL FORWARD TRAVEL OF TISSUE CUTTING/CAPTURE COMPONENT COMPLETED AND ELECTROSURGICAL GENERATOR CUTTING WAVEFORM APPLICATION IS AUTOMATICALLY TERMINATED. AURAL CUE OCCURS AT PREDETERMINED POSITION DURING FORWARD TRAVEL OF TISSUE CUTTING/CAPTURE COMPONENT, PURSING CABLE(S) BECOME TAUGHT, CAUSING LEADING EDGE OF TISSUE CUTTING/CAPTURE COMPONENT TO CLOSE, THEREBY SEVERING THE ENCAPSULATED TISSUE VOLUME FROM SURROUNDING TISSUE. ALTERNATIVELY, AT PREDETERMINED POSITION IN FORWARD TRAVEL OF TISSUE CUTTING/CAPTURE COMPONENT, MOTORIZED PURSING CABLE UPTAKE REEL MAY BE ACTUATED TO WITHDRAW CABLE TO EFFECT CLOSURE OF THE LEADING EDGE OF THE TISSUE CUTTING/CAPTURE COMPONENT.

↓ ⎯ 954

OPTIONALLY, INSERT OR DEPLOY MARKER COMPONENT (e.g., SPRING, LOOP OR RING) THRU AUXILIARY CHANNEL WITHIN GUIDE WIRE TO FACILITATE SUBSEQUENT LOCATION OF REGION WHERE TISSUE WAS REMOVED. ⎯ 956

↓ ⎯ 958

REMOVE TISSUE CUTTING/CAPTURE COMPONENT FROM BODY AND SEVER PURSING CABLE TO RELEASE ENCAPSULATED TISSUE VOLUME (e.g., FOR SUBSEQUENT PATHOLOGICAL EXAMINATION) ⎯ 960

FROM FIG. 70C

┌─────────────────────────────────────┐
│ OPTIONALLY, WHILE REMOVING TISSUE   │ ─ 964
│ CUTTING/CAPTURE COMPONENT FROM THE BODY, │
│ ENERGIZE THE ONE OR MORE WIRE ELECTRODES │
│ AT ITS LEADING EDGE USING COAGULATING │
│ CURRENT WAVE FORM (e.g., WHITE COAGULATION) │
│ TO EFFECT SEALING OF ANY SEVERED BLOOD │
│ VESSELS AND/OR CAUTERIZATION OF INTERIOR │
│ SURFACES OF TISSUE CAPTURE VOLUME AND │
│ TROCAR TRACK TO MINIMIZE POSSIBILITY OF │
│ NEEDLE TRACK METASTASIS.            │
└─────────────────────────────────────┘

↓ 966

┌─────────────────────────────────────┐
│ OPTIONALLY, IF EXCESSIVE BLEEDING OCCURS │ ─ 968
│ BEFORE OR AFTER REMOVAL OF TISSUE   │
│ CUTTING/CAPTURE COMPONENT, INJECT   │
│ HEMOSTATIC AGENT (e.g., FIBRIN GLUE) INTO │
│ CAVITY OCCUPIED BY TARGET TISSUE VOLUME │
│ AND/OR INSTRUMENT ACCESS TRACK TO EFFECT │
│ HEMOSTASIS; ALTERNATIVELY, BALLOON MAY BE │
│ INSERTED INTO CAVITY FOLLOWING REMOVAL OF │
│ TISSUE CUTTING/CAPTURE COMPONENT AND │
│ INFLATED TO APPLY TAMPONADE TO EFFECT │
│ HEMOSTASIS (i.e., CESSATION OF BLEEDING FROM │
│ ANY SEVERED BLOOD VESSELS.)         │
└─────────────────────────────────────┘

↓ 970

( END ) ─ 972

MINIMALLY INVASIVE INTACT RECOVERY OF TISSUE

CROSS-REFERENCE TO RELATED APPLICATIONS

None

STATEMENT REGARDING FEDERALLY SPONSORED RESEARCH

Not applicable.

BACKGROUND OF THE INVENTION

It is estimated that one out of eight women will face breast cancer at some point during her lifetime, and for women age 40–55, breast cancer is the leading cause of death. While methods for detecting and treating breast cancer initially were crude and unsophisticated, advanced instrumentation and procedures now are available which provide more positive outcomes for patients.

In the 1800s the only treatment for breast cancer was removal of the entire breast. Given that the sole method of detection and diagnosis was palpation, treatment was only directed when the breast tumor was well advanced. Modified radical mastectomies are still performed today for patients with invasive cancer, such a procedure involving the removal of the entire breast and some or all of the axillary lymph nodes. Radical or modified radical mastectomies involve serious trauma for the patient during surgery with the severest cosmetic results after surgery.

Another surgical option upon the discovery of malignant tumor is what is referred to as breast conserving surgery, which also is referred to as lumpectomy, tumorectomy, segmental mastectomy and local excision. Meant to address the cosmetic concerns associated with removal of the breast, only the primary tumor and a margin of surrounding normal breast tissue is removed. Determining the proper amount of tissue to be removed involves balancing the need to take sufficient tissue to prevent recurrence with the desire to take as little tissue as possible to preserve the best cosmetic appearance. A more limited nodal dissection now is performed with the primary purpose being staging rather than therapy. While an improvement over radical mastectomy, breast-conserving surgery still involves the removal of large sections of breast tissue. Risks associated with such surgery include wound infection, seroma formation, mild shoulder dysfunction, loss of sensation in the distribution of the intercostobrachial nerve, and edema of the breast and arm. For more information on invasive tumor therapy, see:

(1) Harris, Jay R., et al. "Cancer of the Breast." *Cancer: Principles and Practices of Oncology, Fourth Edition.* Eds. DeVita, et al. Philadelphia: J. B. Lippincott Co., 1993. 1264–1285.

(2) Jobe, William E. "Historical Perspectives." *Percutaneous Breast Biopsy.* Eds. Parker, et al. New York: Raven Press, 1993. 1–5.

Mastectomies and breast-conserving surgeries generally are procedures utilized for invasive tumor. Advances in tumor detection, however, have radically changed the course of diagnosis and treatment for a tumor. With the advent of imaging devices, such as the mammogram, suspect tumor may be located when it is of relatively small size. Today, tumor detection generally involves both a mammogram and a physical examination, which takes into account a number of risk factors including family history and prior occurrences. Technical improvements in mammogram imaging include better visualization of the breast parenchyma with less exposure to radiation, improvements in film quality and processing, improved techniques for imaging, better guidelines for the diagnosis of cancer and greater availability of well-trained mammographers. With these advancements in imaging technology, a suspect tumor may be detected which is 1 cm or smaller. More recently substantial progress has been witnessed in the technical disciplines of magnetic resonance imaging (MRI) and ultrasound imagining. With these advances, the location of a lesion is observable as diagnostic/analytic or therapeutic procedures are carried out.

In the past, because a tumor normally was not discovered until it had reached an advanced stage, the issue of whether a tumor was malignant or benign did not need to be addressed. With the ability to locate smaller areas of suspect tumor, this issue becomes of critical importance, particularly in light of the fact that only 20% of small, non-invasive tumors are malignant. Tumors identified as being benign may be left in situ with no excision required, whereas action must be taken to excise suspect tissue confirmed to be malignant. In view of the value of classifying a tumor as malignant or benign, breast biopsy has become a much-utilized technique with over 1 million biopsies being performed annually in the United States. A biopsy procedure involves the two step process of first locating the tumor then removing pall or all of the suspect tissue for examination to establish precise diagnosis.

One biopsy option available upon detection of a suspect tumor is an open surgical biopsy or excisional biopsy. Prior to surgery, a radiologist, using mammography, inserts a wire into the breast to locate the tumor site. Later during surgery, the surgeon makes an incision in the breast and removes a large section of breast tissue, including the suspect tissue and a margin of healthy tissue surrounding the tumor. As with other similar procedures, such as those described above, open surgery may result in high levels of blood loss, scarring at the location of the incision and permanent disfigurement, due to the removal of relatively large amounts of tissue. Because of the critical prognostic significance of tumor size, the greatest advantage of the excisional biopsy is that the entire area of the suspect tumor is removed. After being removed and measured, the specimen is split by a pathologist in a plane that should bisect a tumor if present, then the margin between tumor and healthy tissue is examined. Microscopic location of carcinoma near the margin provides information for future prognosis. Thus the pathology laboratory is oriented to the morphological aspect of analysis, i.e. the forms and structures of involved tissue.

For information on pathology of breast biopsy tissue, see:

(3) Rosen, Paul Peter. *Rosen's Breast Pathology.* Philadelphia: Lippincott-Raven Publishers, 1997. 837–858.

Other less invasive options are available which avoid the disadvantages associated with open surgery. One such non-invasive option is that of needle biopsy, which may be either fine needle aspiration or large core. Fine needle aspiration (FNA) is an office procedure in which a fine needle, for example of 21 to 23 gauge, having one of a number of tip configurations, such as the Chiba, Franzeen or Turner, is inserted into the breast and guided to the tumor site by mammography or stereotactic imaging. A vacuum is created and the needle moved up and down along the tumor to assure that it collects targeted cellular material. Generally, three or more passes will be made to assure the collection of a sufficient sample. Then, the needle and the tissue sample are withdrawn from the breast.

The resulting specimen is subject to a cytologic assay, as opposed to the above-noted morphological approach. In this regard, cell structure and related aspects are studied. The resultant analysis has been used to improve or customize the selection of chemotherapeutic agents with respect to a particular patient.

While a fine needle aspiration biopsy has the advantages of being a relatively simple and inexpensive office procedure, there are some drawbacks associated with its use. With fine needle aspiration, there is a risk of false-negative results, which most often occurs in cases involving extremely fibrotic tumor. In addition, after the procedure has been performed there may be insufficient specimen material for diagnosis. Finally, with fine needle aspiration alone the entire area of suspect tissue is not removed. Rather, fragmented portions of tissue are withdrawn which do not allow for the same type of pathological investigation as the tissue removed during an open surgery biopsy.

This limitation also is observed with respect to large core needle biopsies. For a large core needle biopsy, a 14 to 18 gauge needle is inserted in the breast having an inner trocar with a sample notch at the distal end and an outer cutting cannula. Similar to a fine needle aspiration, tissue is drawn through the needle by vacuum suction. These needles have been combined with biopsy guns to provide automated insertion that makes the procedure shorter and partially eliminates location mistakes caused by human error. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples, however, they still do not provide the pathological information available with an open surgical biopsy specimen. Further, as with any mechanical cutting device, excessive bleeding may result during and following the procedure. Needle biopsy procedures are discussed in:

(4) Parker, Steve H. "Needle Selection" and "Stereotactic Large-Core Breast Biopsy." *Percutaneous Breast Biopsy*. Eds. Parker, et al. New York: Raven Press, 1993. 7–14 and 61–79.

A device which is somewhere between a needle biopsy and open surgery is referred to as the Advanced Breast Biopsy Instrumentation (ABBI). With the ABBI procedure, the practitioner, guided by stereotactic imaging, removes a core tissue sample of 5 mm to 20 mm in diameter. While the ABBI has the advantage of providing a large tissue sample, similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for the ABBI is limited by the size and location of the tumor, as well as by the presence of very dense parenchyma around the tumor. For discussion on the ABBI, see:

(5) Parker, Steve H. "The Advanced Breast Biopsy Instrumentation: Another Trojan Hourse?" Am. J. Radiology 1998; 171: 51–53.

(6) D'Angelo, Philip C., et al. "Stereotactic Excisional Breast Biopsies Utilizing the Advanced Breast Biopsy Instrumentation System." Am J Surg. 1997; 174: 297–302.

(7) Ferzli, George S., et al. "Advanced Breast Biopsy Instrumentation: A Critique." J Am Coll Surg 1997; 185: 145–151.

Another biopsy device has been referred to as the Minimally Invasive Breast Biopsy (MIBB). This carries out a vacuum-assisted core biopsy wherein fragments of suspect tissue are removed with an 8 gauge needle. While being less invasive, the MIBB yields only a fragmentary specimen for pathological study. The MIBB therefore is consistent with other breast biopsy devices in that the degree of invasiveness of the procedure necessarily is counterbalanced against the need for obtaining a tissue sample whose size and margins are commensurate with pathology requirements for diagnosis and treatment.

With all of the above diagnostic specimen collection and therapeutic removal procedures, opportunity exists for a seeding metastasis of healthy tissue with instrument borne malignant cells. Such activity typically will occur as an instrument or needle is removed from engagement with a malignant tumor.

BRIEF SUMMARY OF THE INVENTION

The present invention is addressed to apparatus, system and method for retrieving a targeted tissue volume in intact form utilizing surgical instrumentation which is minimally invasive. The instrument includes a tubular delivery cannula of minimum outer diameter, the tip or distal end of which is positioned in confronting adjacency with the tumor or tissue volume to be removed. Positioned within an interior channel of this delivery cannula is a generally tubular-shaped capture component which is configured having an expansible forward portion extending to a forwardly disposed leading edge portion. That leading edge portion carries out electrosurgical cutting. A deployment assembly, configured with the delivery channel and the capture component, functions to move the capture component forward portion toward the region of the tumor. This movement also causes that forward portion to expand as its leading edge portion electrosurgically cuts though healthy tissue adjacent the targeted tumor. Upon completion of the expansion, the forward region of the capture component will generally extend about the targeted tumor and a component of adjacent healthy tissue, whereupon the deployment assembly causes the electrosurgically cutting leading edge portion to be contracted while continuing to cut, toward a closed orientation. This effects a circumscribing isolation of the targeted and adjacent tissue. The delivery cannula then is removed with the tissue specimen containing capture component. As this removal maneuver is carried out, electrosurgical cutting excitation of the capture component leading edge portion will have been terminated. However, the leading edge portion may then be excited to carry out white coagulation during removal along adjacent tissue. This serves to necrotize healthy tissue adjacent the incision to prevent seed metastasis.

An avoidance of seed metastasis also is realized with the intact removal of the entire suspicious lesion and accompanying surrounding marginal healthy tissue.

The instrument may also be formed having an auxiliary channel extending along its entire length in a longitudinally generally centrally disposed location. In the event that the targeted tumor has been marked with a localization wire, the auxiliary channel at the forward portion of the instrument may be positioned over the outwardly extending end of the localization wire. Thus, guidance of the instrument toward the noted position wherein the forward end of the delivery cannula confronts the tissue volume is facilitated. The utility channel also may be employed to receive the elongate needle employed in conjunction with fine needle aspiration procedures. Such a procedure preferably is carried out when the delivery cannula initially is positioned in confronting relationship with the target tumor and adjacent tissue and before electrosurgical cutting and deployment of the capture component commences. Such a procedure serves to avoid seed metastasis in consequence of the subsequent white coagulation activity carried out during instrument removal. The utility channel further may be employed to express a necrotizing and/or hemostasis effecting fluid into the surgical incision developed in the above-described capturing maneuver.

In a preferred embodiment, the capture component forward portion is configured having a plurality of discrete, elongate cage defining leafs integrally formed within its generally tubular structure having sides extending in parallel with the longitudinal axis of the delivery cannula to leaf tip portions. Attached to these leaf tip portions is a flexible metal wire which is electrosurgically excited to carry out the cutting and white coagulation functions and further serves as a component of a pursing cable. The deployment assembly employed with this capture component includes a guidance assembly which is fixed to the delivery cannula adjacent its distal end and is configured for guiding the cage defining leafs annularly, outwardly at a predetermined attack angle to extend over the targeted tumor and adjacent healthy tissue in a manner somewhat defining a cage. Contraction of the forward tips of the leafs is carried out with the noted metal wire and associated pursing cable assembly.

In a second embodiment, the cylindrical capture component is compressibly constrained within the internal channel of the delivery cannula. This capture component is configured with a mesh type of geometry and of a metal having an elastic capability for springing outwardly towards formation of an enlarged cylindrical periphery when extruded from the delivery cannula distal end as it is in confronting orientation before the targeted tumor. As this gradual extrusion occurs, the leading edge portion of the capture component is electrically excited for energy assisted electrosurgical cutting through tissue along a path which initially is conical and subsequently assumes a generally cylindrical shape which extends over the targeted tumor and adjacent tissue for the purpose of isolating it in a circumscriptive manner. At a controlled extent of this extrusion, pursing cables attached to the leading edge portion of the capture component are tensioned to draw the cutting leading edge into itself to essentially encapsulate the target tissue volume while excising it from the viable tissue which surrounds it. As before, the instrument, with captured tissue, then is withdrawn for pathological study. For both embodiments, the target tissue volume advantageously remains intact to support such studies. In general, for the second embodiment, the capture component is rotated during the electrosurgical cutting procedure inasmuch as electrosurgical cutting is carried out with minute spaced apart blades at its leading edge.

Another aspect of the second embodiment of the invention resides in the configuring of a forward region of the delivery cannula such that it will elastically expand into a cone-shape when released from confinement. To retain this forward region in a cylindrical shape during an insertion mode wherein the delivery cannula is positioned in the noted confronting orientation, a confinement sleeve is slidably positioned over it. Following insertion of the instrument delivery cannula tip into the noted confronting orientation, the sleeve is retracted to release the forward end region for cone formation. As this release occurs, adjacent tissue is displaced to, in effect, form a void. As the leading edge of the capture component is extruded, the now cone-shaped delivery cannula tip region functions as a conical guide for the somewhat delicate capture component. Following isolation and capture of the specimen tissue, the opposite or exterior surface of the cone-shaped forward end region performs as a tissue dilatory to facilitate withdrawal.

Insertion of the forward region of instruments of the invention through the epidermis and into a confronting attitude with respect to a targeted lesion is facilitated by the provision of an electrosurgical precursor lancet electrode. This cutting electrode is deployable to extend both forwardly and outwardly from the distal tip of the instrument. Such deployment creates two, coplanar, arch-defining loops, the forwardly positioned leading edges of which, quite readily surgically part and pass through tissue without disrupting displacement. The extent of arch deployment is predicated upon the effective diameter of the target lesion and captured surrounding tissue margin. When the instrument is properly positioned, the deployed lancet electrodes are retracted.

Another feature of the invention is to provide a method for isolating and retrieving a targeted volume of tissue situated within a volume of adjacent tissue, comprising the steps of:

(a) providing an electrosurgical generator controllable to derive an electrosurgical cutting output of predetermined cutting voltage level and an associated electrical return;

(b) providing a tissue isolation and retrieval instrument having a delivery cannula with an outer surface and an internal channel and extending from a proximal end portion along a longitudinal axis to a forward region extending inwardly from a distal end. The instrument is provided having a capture component positioned within the delivery cannula interior channel, having an expansible forward portion extending to a forwardly disposed, electrically conducting electrosurgical cutting leading edge portion and being expandable toward an outer peripheral dimension selected to correspond at least with the dimension of the targeted tissue peripheral extent. The instrument further is provided having a deployment mechanism drivably coupled with the capture component for effecting the movement of the capture component along the instrument longitudinal axis and for effecting a contraction of the leading edge portion toward the longitudinal axis;

(c) positioning the delivery cannula within the adjacent tissue with the distal end in confronting relationship with one side of the targeted tissue peripheral extent;

(d) slidably expressing the capture component forward portion from the delivery cannula forward region to effect expansion of the leading edge portion outwardly toward the outer peripheral dimension;

(e) when the leading edge portion approaches a side of the targeted tissue opposite the one side, effecting a contraction of the leading edge portion;

(f) simultaneously with steps (d) and (e), controlling the electrosurgical generator to apply the electrosurgical cutting output thereof to the electrically conductive leading edge portion to create an incision within the adjacent tissue extending around, substantially enveloping, isolating and capturing the targeted volume of tissue;

(g) controlling the electrosurgical generator to terminate the electrosurgical cutting output and;

(h) removing the delivery cannula and capture component with the captured tissue from adjacency with the adjacent tissue.

Other objects of the invention will, in part, be obvious and will, in part, appear hereinafter. The invention, accordingly, comprises the method, system and apparatus possessing the construction, combination of elements, arrangement of parts and steps which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 2 is a side view of an instrument according to the invention;

FIG. 3 is a sectional view taken through the plane 3—3 in FIG. 2;

FIG. 4 is an enlarged view showing a portion of a delivery cannula illustrated in FIGS. 2 and 3.;

FIG. 6 is a plan view of a capture component prior to its being formed into a cylindrical shape;

FIG. 13 is a side view of the instrument of FIG. 2 with a retracted confinement sleeve;

FIG. 14 is a sectional view taken through the plane 14—14 in FIG. 13;

FIG. 17 is a side view of the instrument of FIG. 2 showing the commencement of deployment of a capture component;

FIG. 18 is a sectional view taken through the plane 18—18 in FIG. 17;

FIG. 23 is a front view of a semi-automatic instrument according to the invention;

FIG. 24 is a partial sectional view taken through the plane 24—24 of FIG. 23;

FIGS. 25A–25C combine as labeled thereon to provide a flowchart illustrating a methodology of the invention;

FIG. 26 is a side view of an instrument according to the invention;

FIG. 27 is a partial sectional view taken through the plane 27—27 in FIG. 26;

FIG. 28 is a partial side view showing an internal guide member employed with the instrument of FIG. 26;

FIG. 29 is a partial side view of a capture component employed with the instrument of FIG. 26;

FIG. 30 is a developed view of the capture component of FIG. 29;

FIG. 31 is a sectional view taken through the plane 31—31 shown in FIG. 30;

FIG. 43 is a side view of an instrument according to the invention;

FIG. 44 is a sectional view taken through the plane 44—44 in FIG. 43;

FIG. 45 is a partial side view showing an internal guide member employed with the instrument of FIG. 43;

FIG. 46 is a partial side view of a capture component employed with the instrument of FIG. 43;

FIG. 47 is a developed view of the capture component of FIG. 46;

FIG. 50 is a partial sectional view of the control and support assembly of the instrument of FIG. 43;

FIG. 51 is a sectional view of the assembly of FIG. 50 showing the orientation of components following an energization of a contained electric motor;

FIG. 59 is perspective view of the instrument of FIG. 43 showing an adaptation thereof wherein an electrosurgical precursor lancet electrode is deployed from its forward region;

FIG. 60 is a partial sectional view of the instrument of FIG. 59 taken through the plane 60—60 therein;

FIG. 62 is a sectional view of the forward region shown in FIG. 60 with a retracted orientation for an electrosurgical precursor lancet electrode;

FIG. 69 is a block diagrammatic circuit drawing showing a dedicated electrosurgical generator which may be employed with the instrument embodiments of FIGS. 43–62; and FIGS. 70A–70D combine as labeled thereon to illustrate a procedure which may be employed with the instrument embodiments of FIGS. 43–62.

DETAILED DESCRIPTION OF THE INVENTION

Figure 1A:
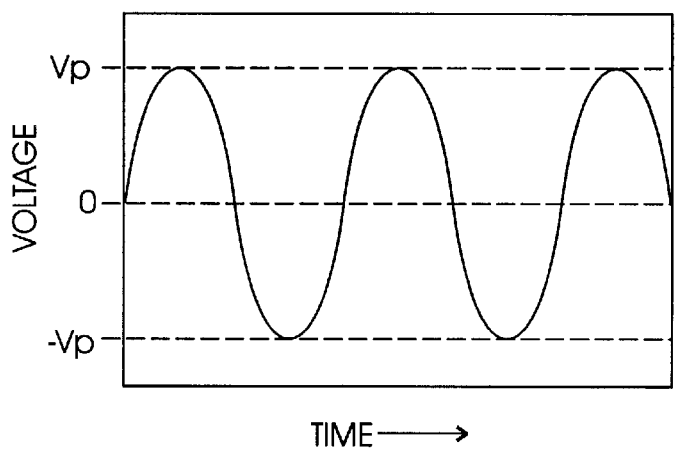
FIGS. 1A through 1E illustrate electrosurgical waveforms.
Figure 1B:
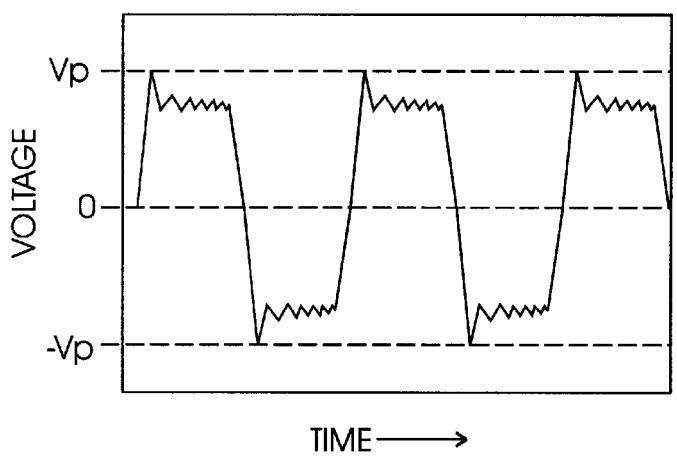
Figure 1C:
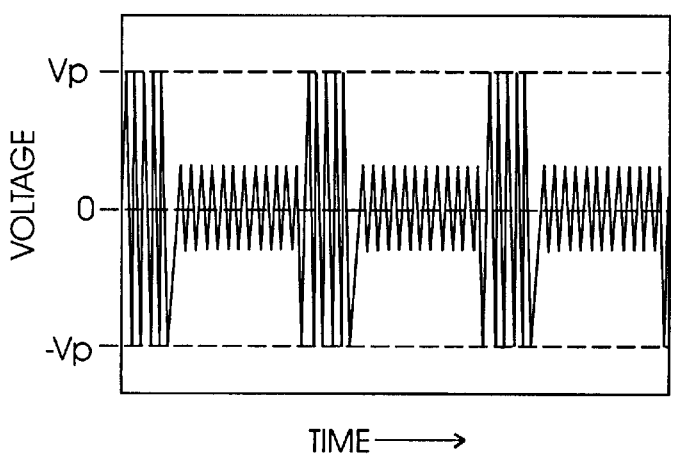

A predominate characteristic of the invention resides in the employment of a capture component in conjunction with a delivery cannula. The capture component is configured with an expansible forward portion which extends to a forwardly disposed cutting leading edge portion which is electrosurgically excited to form an incision. Targeted tumor or tissue along with adjacent healthy tissue is circumscribed by this capture component through the utilization of a pursing assembly which constricts the leading edge portion to, in effect, encapsulate the incised tissue volume. In the discourse to follow, an initial embodiment is described employing a capture component which is configured having a compressibly stressed initial state. The electrosurgically cutting leading edge portion is configured with discrete cutting members which are excited while being both rotated and advanced toward the involved tissue volume. In the second, preferred embodiment, a steel pursing cable is electrosurgically excited to carry out the cutting procedure with no rotational requirement being involved. The term "cannula" as used herein is intended to refer to any elongate surgical delivery structure, rigid or flexible, having a capability for deploying electrosurgical components.

Referring to FIG. 1, an initial system for retrieving a targeted tissue volume in accordance with the invention is represented generally at 10. System 10 includes a tissue isolation and retrieval instrument or apparatus represented generally at 12. Instrument 12 is seen to have a relatively thin elongate cylindrical forward portion represented generally at 14 which includes the point or tip 16 of a trocar. Forward portion 14 is connected to a control and support assembly represented generally at 18. The assembly 18 incorporates deployment assembly mechanisms and, for the instant embodiment, is formed with a hand grip portion 20 and a finger loop-type hand actuator 22 which is configured to pivot about a pin connection at 24. Forwardly of the assembly 18 is a component of the deployment mechanism of the device present as a cylindrical knob 26. On the opposite side of the assembly 18 is a trocar retracting knob 28, and seen extending from the top surface of assembly 18 is a pursing cable latch assembly represented generally at 30. The instrument 12 is depicted in its initial or insertion mode wherein the forward cylindrical surface of the forward portion 14 is that of a confinement sleeve 32. In the configuration shown, the trocar tip or point 16 is employed for maneuvering the front of the instrument into a confronting attitude with respect to a targeted tissue volume. Generally, a small incision through the patient's skin is made to commence this insertion and positioning activity. Instrument 12 carries out an electrosurgical or energy assisted form of cutting and coagulation in the course of its use. Accordingly, its control system includes an electrosurgical generator represented generally at 34. Generator 34 incorporates a front panel 36 at the lower level of which are provided three connector receiving receptacles 38–40. Visual cueing is provided by two light emitting diodes (LED). The first of these diodes 42 is a power-on indicator which is energized upon power-up with a switch 44. A second LED, 46 is energized when the generator 34 is activated to provide an output to the instrument 12. Generally, during the provision of such an output, an aural cue is provided from a speaker behind a grill seen at the top of the device at 48.

A control assembly cable is shown at 50 extending from the instrument 12 assembly 18 to a connector 52 electrically coupled with the connector 40. Instrument 12 may perform in a monopolar fashion while carrying out electrosurgical cutting. One approach to developing a return for this form of cutting, a conventional remote patient return electrode, is provided as shown at 54. Electrode 54, having an extended surface area, is applied to a surface of the patient's body and is seen connected to generator 34 by a cable 56 extending to a connector 58 electrically attached to the connector 39.

It is advantageous for the system 10 to be utilized in conjunction with a local anesthetic. However, because remote monopolar based return electrodes as at 54 involve the passage of current essentially through the patients body, muscle stimulation typically is encountered. Where that stimulation hinders the procedure at hand, then electrosurgical cutting is carried out in conjunction with the administration of a paralyzing agent. Such agents typically utilize curare. A form of that substance extracted from chondodendron tomentosum, is used to avoid muscle spasms in conjunction with resort to general anesthesia including a respirator. A coupling the electrosurgical return to an electrically conductive trocar point 16 or a position forwardly upon the instrument 12 adjacent that tip will provide a confinement of current flow to within a very small region of tissue and permit utilization of a local anesthetic.

Upon power-up, the generator 34 will provide an output at cable 50 to the instrument 12 by depressing an appropriate foot pedal 60 or foot pedal 62 of a switch assembly 64. In this regard, switch 64 includes a cable 66, extending to a connector 68 electrically connected to corresponding connector 38. Generators as at 34 may be adjusted or configured to provide several forms of output, two of which may be selected in conjunction with the depression of either foot pedal 60 or 62. For the present system, these foot pedals elect either a an electrosurgical cutting output or an electrosurgical coagulating output. When high-frequency currents are used for cutting and coagulating, the tissue at the surgical site experiences controlled damage due either to disruptive mechanical forces or distributed thermal damage.

Electrosurgical cutting is caused by disrupting or ablating the tissue in immediate apposition to the cutting electrode, i.e., the electrode is slightly spaced from the tissue. In general, continuous sinusoids are employed for cutting purposes. In contrast, coagulation is accomplished by denaturation of tissue proteins due to thermal damage. Both interrupted and continuous waveforms are employed for various forms of coagulation. In this regard, coagulation techniques include:

(1) Fulguration, which also is referred to as "spray coagulation" or 'black coagulation", the process causing a carbonization of tissue by arc strikes;
(2) Desiccation, in which the tissue cells are dehydrated, resulting in shrinking; and
(3) White coagulation, in which the tissue is more slowly cooked to a coagulum.

White coagulation, which is employed with the present system, elevates tissue temperatures to 55° C. or greater and the heating profile is determined by the electrical properties of the tissue and by the total current used. With the technique, the electrosurgical electrode is in intimate contact with the tissue and no arcs strike so that electrode voltage is quite low. The total electrode current may be high, but the tissue current density (current per unit area) at all points on the electrode is quite low and the duration of the activation is therefore relatively long.

Referring momentarily to FIG. 1A, a sinusoidal electrosurgical waveform is depicted. This waveform evolves in a voltage range of about 500 to 2000 volts, peak-to-peak, a frequency range from about 20 kHz to about 20 MHz and will exhibit a crest factor from about 1.0 to about 1.4. Looking to FIG. 1B another cutting waveform is represented. This waveform will exhibit the same voltage and frequency range as described in connection with FIG. 1A and will exhibit a crest factor from about 1.5 to about 2.0. Looking to FIG. 1C, a blend waveform is represented. This type of waveform combines a waveform employed for fulguration with a cutting sinusoid to both cut and evoke a hemostasis or bleeding control. The blend waveform represents a slower cutting modality, having a voltage which is ranging from about 1000 to 4000 volts peak-to-peak, the same frequency ranges as with sinusoidal cutting waveforms and will exhibit a crest factor value from about 2.5 to 10.0.

Figure 1D:
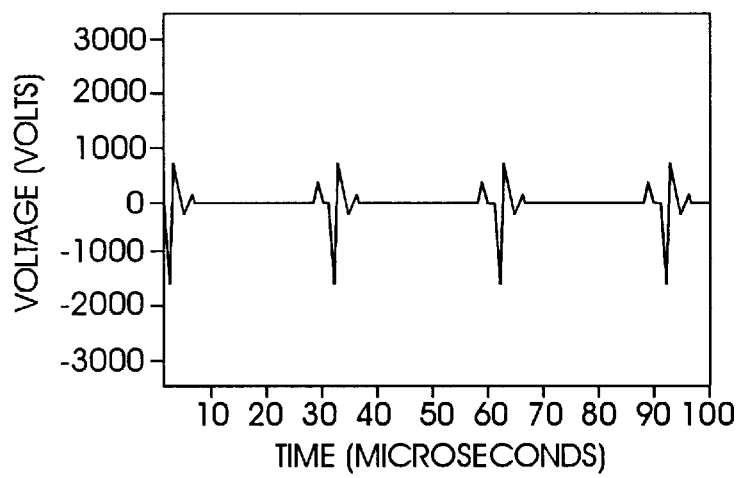

Looking to FIG. 1D, a conventional fulguration form of coagulation waveform is represented. Interruptedness and low duty cycle are key defining features of the arc generating coagulation approach. The interrupted waveform will exhibit a relatively low current level and a voltage range from about 1500 to 9000 volts peak-to-peak.

Figure 1E:
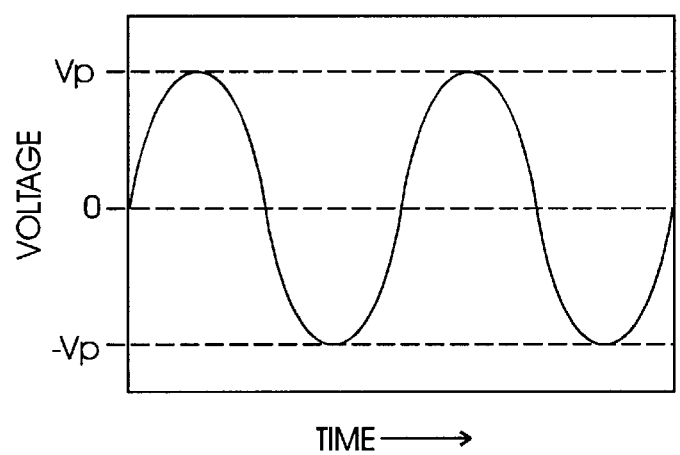
Figure 1F:
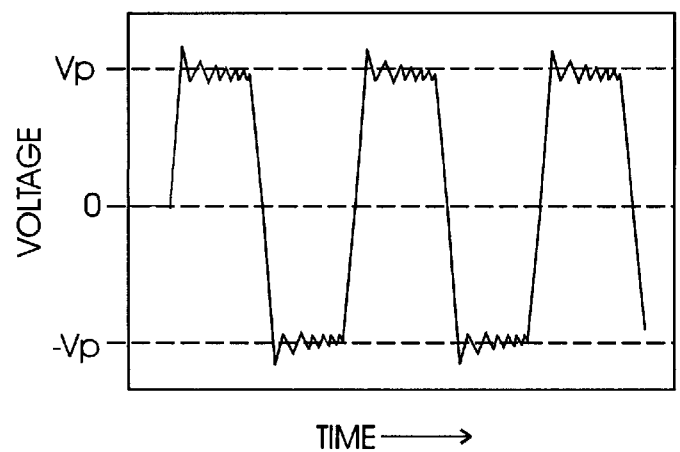
FIG. 1 is a perspective view of one embodiment of the system of the invention.

Referring to FIGS. 1E and 1F, the waveforms employed with white coagulation techniques are portrayed. Note that in FIG. 1E, the waveform is a continuous sinusoid. However, this form of coagulation is carried out within a voltage range of about 20 to about 500 volts peak-to-peak and in a frequency range of about 20 kHz to about 20 MHz. The crest factor exhibited by the waveform falls in a range of about 1.0 to 1.4. In FIG. 1F, the white cauterization waveform approach is a squarewave and exhibits the same voltage range and frequency range as the sinusoidal waveform of FIG. 1E. The crest factor exhibited by the waveform of FIG. 1F will fall within a range of about 1.5 to about 2.0. See generally:

(8) "*Electrosurgery*" by J. A. Pearce, John Wilely & Sons, New York, N.Y., 1986.

While a variety of conventional electrosurgical generators may be employed with the system 12, it is a desirable feature that the generator selected be a dedicated one with an assured proper output. In general, procedures such as fulguration require high voltages to initiate arcs, but not large currents. Consequently a generator of high output impedance may be employed. Spray coagulation uses higher currents at high voltages, the difference between spray coagulation and the fulguration being one of degree rather than principle. White coagulation calls for relatively high current at low voltage, no arc being formed at the electrode. Where the above described instrument borne return electrodes are employed which are situated adjacent tissue locations which will be relatively close, a bipolar or quasi-bipolar circuit arrangement is evoked. In this arrangement, the current field is confined to the forward region of the instrument. For white coagulation under these circumstances, the current may be moderate to high, for example, hundreds to thousands of milliamps (R.M.S.) and the voltage will be very low as above discussed. Generators suited for use with the system 10 will include, for example, an electrosurgery generator marketed under the trade designation "Model Force 2" by Valleylab, Inc., of Boulder, Colo., or marketed under the trade designation "Model ICC350" by ERBE of Tuebingen, Germany.

Referring to FIG. 2, the instrument 12 is more clearly illustrated. In the figure, instrument 12 is represented in its initial or insertion mode configuration. In this regard, the trocar retraction knob 28 is at a forward position such that the trocar point 16 protrudes forwardly. Cylindrical knob 26 also is in a forward initial state orientation. Knob 26 is attached to the confinement sleeve 32 which, in turn, is slidably positioned upon an elongate tubular delivery cannula 80 which is rotatably mounted upon the control or deployment assembly 18 at its forward region 82. Delivery cannula 80 extends forwardly to a distal end 84 located adjacent the trocar point 16. Finally, it may be observed that in this initial state, the hand actuator 22 is oriented forwardly toward the tip of the instrument.

Figure 5:
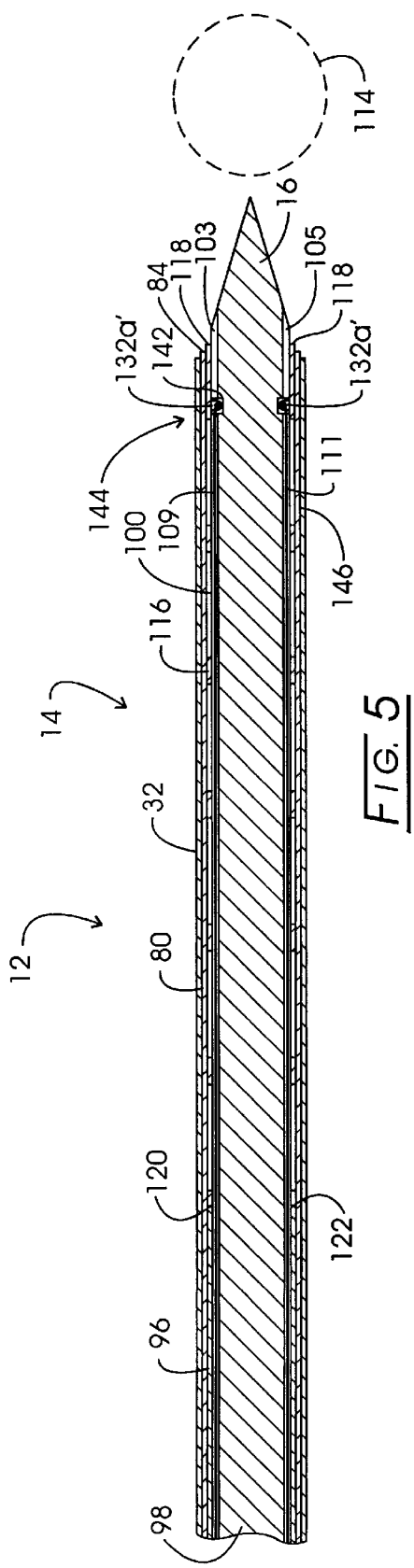
FIG. 5 is a sectional view taken through the plane 5—5 in FIG. 2.

In addition to being fixed to and moveable with the confinement sleeve 32, the knob 26 is configured having a pin and slot connection with the delivery cannula 80. Referring additionally to FIGS. 3 and 4, the delivery cannula 80 is revealed to have an "L" shaped slot formed therein which is represented generally at 86. Positioned immediately forwardly of forward region 82 of control assembly 18, the slot includes a transverse leg 88 and a longitudinal leg 90. FIG. 3 reveals that a pin 92 extends through the cylindrical knob 26 in radial fashion and is inserted within the slot 86. For the initial orientation shown, the pin 92 will be positioned within the transverse leg 88 of slot 86. Delivery cannula 80 extends along a longitudinal axis seen in FIG. 2 at 94 and is formed having a cylindrical inner channel extending along that axis. FIG. 3 reveals that within this inner channel there are located components of a deployment mechanism including an elongate drive tube 96 and within that cylindrical tube 96 there is slidably positioned an elongate cylindrical trocar 98 which extends from its tip 16 as seen in FIG. 2 to the trocar retraction knob 28, also seen in FIG. 2. The outer surface 100 of trocar 98 further has four elongate slots formed therein and positioned in quadrature as seen at 102–105 in FIG. 3. The cross-section of slots 102–105 is seen to be rectangular and each additionally is seen to retain one of four pursing cables represented respectively at 108–111. Returning momentarily to FIG. 2, these pursing cables 108–111 are seen to extend from latch assembly 30. Cables 108–111 are formed of an electrically insulative material such as nylon, or an electrical insulation covered metal wire, e.g. polymide covered stainless steel cable. Referring to FIG. 5, a cross-sectional view is provided of forward portion 14 in the vicinity of its tip. In the figure, the tip or point 16 of trocar 98 is seen in a confronting relationship with respect to a targeted tissue volume symbolically represented by dashed circle 114. Confinement sleeve 32 is shown extending forwardly into adjacency with the distal end 84 of delivery cannula 80. Trocar 98 is seen to extend within the interior channel of delivery cannula 80. The figure shows two of the elongate slots, 103 and 105 formed within trocar 98 and two of the pursing cables within those slots as shown respectively at 109 and 111. Between the outer surface 100 of the trocar 98 and the internal surface of delivery cannula 84 there is a compressibly stressed and retained cylindrically shaped metal capture component 116. The leading edge of capture component 116 is shown at 118 extending slightly forwardly from the distal end 84 of delivery cannula 80. In this compressibly stressed initial state, the capture component 116 extends rearwardly within the interior channel of delivery cannula 80 to a driving edge 120, the cylindrical shape of which is abuttably engaged with and in electrically conducting association with the annular forward surface 122 of drive tube 96. FIG. 5 further reveals that pursing cables 109 and 111 extend rearwardly within respective slots 103 and 105 from a location adjacent the leading edge 118 of capture component 116.

Capture component 116, when released from compressive retention present in an initial state or insertion mode, is formed from an open metal mesh structure. Referring to FIG. 6, this open metal mesh structure is revealed following its formation and prior to its being welded into a cylindrical preliminary shape. The mesh structure may be formed by laser cutting or chemical milling, e.g. photoetching processes to define a pattern of metal struts, certain of which are revealed at 124 which are integrally formed within a metal sheet with elastic memory such as type 301 stainless steel having a thickness of between about 0.001 and 0.030 inch. The figure reveals that the struts 124 are mutually spaced and interconnected to define parallelogramic voids, certain of which are shown at 126. To promote rapid expansion of the capture component 116 upon its gradual release during deployment commencing with leading edge 118, the locations of apex tangency or ligaments by which the strut 124-defined parallelograms are mutually coupled together are formed with a widthwise dimension which is diminished in extent. Certain of these locations of apex tangency or ligaments are shown in the figure at 128. Looking momentarily to FIG. 7, this location of apex tangency or ligament 128 is shown in enlarged scale. In general, the widthwise extent of ligament 128, $W_3$, will be from about 0.002 to 0.030 inch, a width preferably less than that of the struts 124. Struts 124 generally will have a widthwise extent, $W_2$, of about 0.003 to 0.030 inch.

Returning to FIG. 6, the leading edge 118 of the capture component 116 is seen to be configured having forwardly extending cutting members fashioned as small blades. These cutting members are identified in four groupings, 130a–130d, 131a–131d, 132a–132d, and 133a–133d. The cutting members or blades extend outwardly from every other metal strut-defined forward apex at the leading edge 118. For the manufacturing stage shown, the cutting members also are provided at their bases with integrally formed coplanar eyelet structures identified with the cutting member numeration but in primed fashion. In the figure, the entire structure 116 is flat. During its fabrication, the edge or side generally identified at 134 is welded to the edge or side generally identified at 136 to form a right cylinder. Additionally, the eyelets are bent inwardly and the entire structure 116, with the exception of the blade shaped cutting members and driving edges 120 is coated with a medically compatible insulation layer. A suitable electrically insulating material is a vapor-phase-polymerized conformal coating marketed under the designation "Parylene". Parylene is the generic name for members of a polymer series. The basic member of the series, called Parylene C, is poly-para-xylene, a completely linear, highly crystalline material. Such coatings are available from Parylene coating service companies such as Specialty Coating Systems, of Indianapolis Ind. These coatings will have a thickness from about 0.0002 inch to 0.020 inch and preferably in a range of about 0.0005 inch to 0.003 inch.

Figure 8:
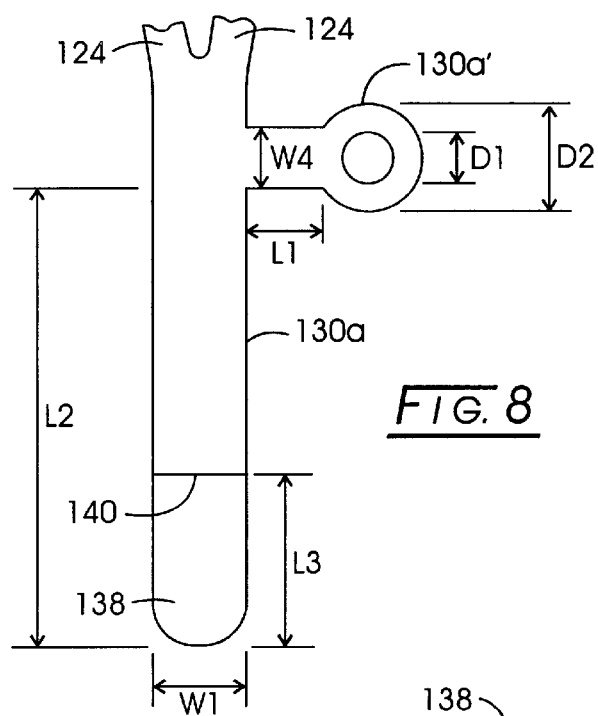
FIG. 8 is a partial plan view of a cutting component illustrated in FIG. 6.
Figure 9:
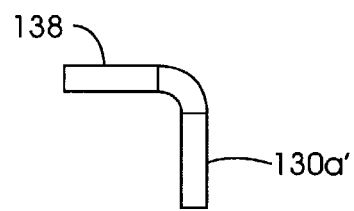
FIG. 9 is a top view of the cutting component of FIG. 8 subsequent to the bending of an eyelet thereof.

Looking to FIG. 8, the cutting member 130a is revealed in magnified fashion in a state prior to the bending of eyelet 130a'. The figure shows an electrosurgical blade tip 138 extending from a boundary 140 representing the distal edge of electrically insulative coating. The figure additionally shows dimensioning symbols. When the eyelets are bent inwardly, the cutting member 130a will have the configuration shown in FIGS. 9 and 10.

Figure 11:
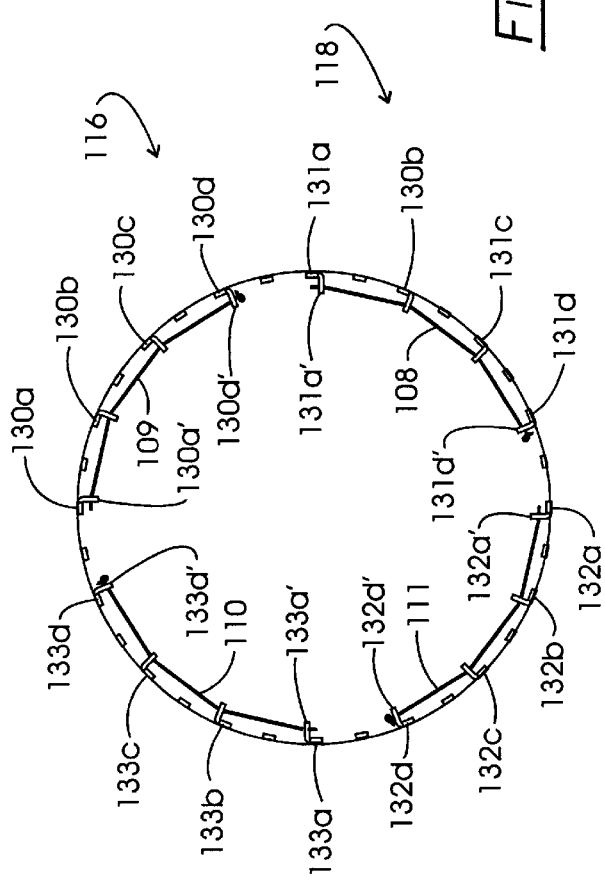
FIG. 11 is a top view of a capture component employed with the instrument of FIG. 2.

When formation of the capture component 116 is completed and it is in its uncompressed state, it will appear as shown in FIG. 11. Note that pursing cable 108 is fastened to eyelet 131d' and is threaded through that grouping of eyelets terminating at eyelet 131a'. Pursing cable 109 is fastened to eyelet 130d' and is threaded through that grouping of eyelets terminating at eyelet 130a'. Similarly, pursing cable 110 is fastened to eyelet 133d' and is threaded through the corresponding grouping to extend from eyelet 133a'. Pursing cable 111 is coupled to eyelet 132d' and extends through the associated eyelets to extend rearwardly from eyelet 132a'.

Returning to FIG. 5, the trocar 98 is seen to be configured having an annular transverse groove 142 formed therein rearwardly of the tip 16. The eyelets described in connection with FIG. 11 extend within this groove when the capture component 116 is in its compressed state and the noted pursing cables 108–111 extend along the four elongate slots 102–105 (FIG. 3) to the latch arrangement 30 (FIG. 2). Shown additionally in FIG. 5 is a forward region of the delivery cannula 80 identified generally at 144 and extending from its distal end 84 to the location identified at 146. Within this forward region 144, the delivery cannula is configured having a plurality of thin slits extending in parallel with the longitudinal axis 94 from end 84 to location 146. Region 144, duling its fabrication, is expanded to normally assume a conical shape. That conical shape, however, during the insertion mode represented at FIG. 5 is restrained to a cylindrical shape by the forward end of the confinement sleeve 32.

Figure 12:
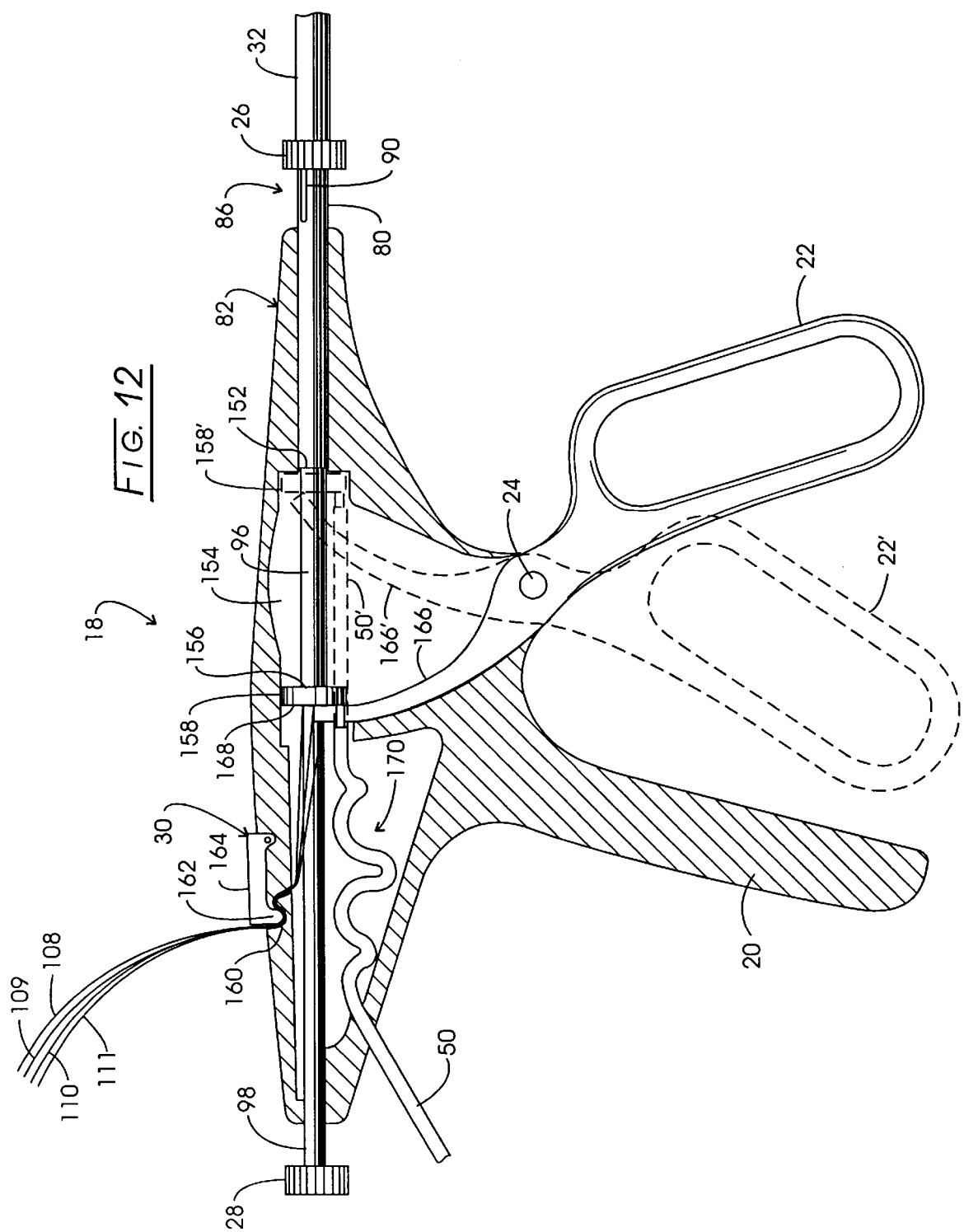
FIG. 12 is a partial sectional view of the deployment assembly of the instrument of FIG. 2.

Referring to FIG. 12, the control or deployment assembly 18 is illustrated at an enhanced level of detail. In the figure, the drive tube 96 (FIG. 3) is shown extending slidably from the proximal end 152 of delivery cannula 80 into an internal cavity 154. The rearward end 156 of drive tube 96 is fixed to a cylindrical drive cam 158. Slidably extending from the rearward end 156 of drive tube 96 is the trocar 98 which protrudes outwardly to be coupled to retracting knob 28. Extending from the elongate slots 102–105 within the trocar 98, as before, are the pursing cables 108–111 which are engaged within a notch 160 by the dog component 162 of the pivoted lever arm 164 of pursing cable latch assembly 30.

Hand actuator 22 extends from its pivoted connection 24 into the cavity 154 with a bifurcate drive lever 166, the two spaced apart tips of which freely abuttably engage the rearward face 168 of drive cam 158. Cam 158 is made of electrically conductive metal as is the drive tube 96 and thus, the drive tube may be electrically excited from cable 50 extending from generator 34 (FIG. 1). This excitation current is conducted to the capture component 116 by virtue of the abutting contact of the forward end 122 of drive tube 96 with its driving edge 120. Such abutting connection is discussed above in connection with FIG. 5. With the arrangement shown, when the actuator handle 22 is drawn rearwardly towards grip 20 as represented, in phantom, at 22', the drive lever 166 serves to push the cylindrical drive cam 158, and thus drive tube 96, forwardly as represented at 166' and 158'. Cable 50 also is drawn forwardly as represented at 50'. To accommodate for this movement, an amount of slack is provided with the cable within the cavity 154 as represented generally at 170.

FIGS. 3 and 12 further reveal that knob 26 may be rotated to move pin 92 from transverse leg 88 of slot 86 (FIG. 4) to longitudinal leg 90. When so oriented, knob 26 and the confinement sleeve 32 attached to it may be drawn rearwardly. Additionally, when the knob 26 is so drawn rearwardly within slot leg 90, it may be utilized to rotate the delivery cannula 80 as well as the confinement sleeve 32.

The exterior surfaces of confinement sleeve 32, delivery cannula 80, where it is exposed behind knob 26 and trocar 98, where exposed forwardly of knob 28 are coated with an electrically insulative layer, such as the earlier described Parylene.

Following the positioning of the tip 16 of trocar 98 and the distal end 84 of delivery cannula 80 in confronting adjacency with targeted tissue volume 114, as discussed in connection with FIG. 5, knob 26 is rotated such that pin 92 (FIG. 3) enters slot 86 longitudinal leg 90 (FIG. 4). Referring to FIG. 13, the orientation status of the instrument components with this retraction of knob 26 is revealed. It may be observed that the knob 26 is adjacent forward region 82 and that the confinement sleeve 32 has been retracted rearwardly to release forward region 144 of delivery cannula 80 from restraint. As a consequence, forward region 144 springs outwardly by virtue of its elastic memory into a cone-shaped configuration through which the point 16 of trocar 98 protrudes. Looking additionally to FIG. 14, it may be observed that releasing forward region 144 from its elastic restraint also has released the leading edge 118 of capture component 116 for movement outwardly in a similar conical formation. It may be recalled from the discourse in connection with FIG. 7, that the widthwise extent of the apex tangency or ligament 128 of the metal struts 124 is selected to enhance the rapidity and extent of this outward movement to conical form. Region 144 of delivery cannula 80 enhances this movement by carrying out a blocking or tissue dilation function and acts as a guide for the capture component 80, providing a well defined conical half-angle represented in the drawing at $\phi_2$. Movement of the region 144 into this conical shape also creates a void within the tissue which further assists the leading edge 118 of capture component 116 in retaining a proper attack angle into the tissue which it confronts.

Figure 15:
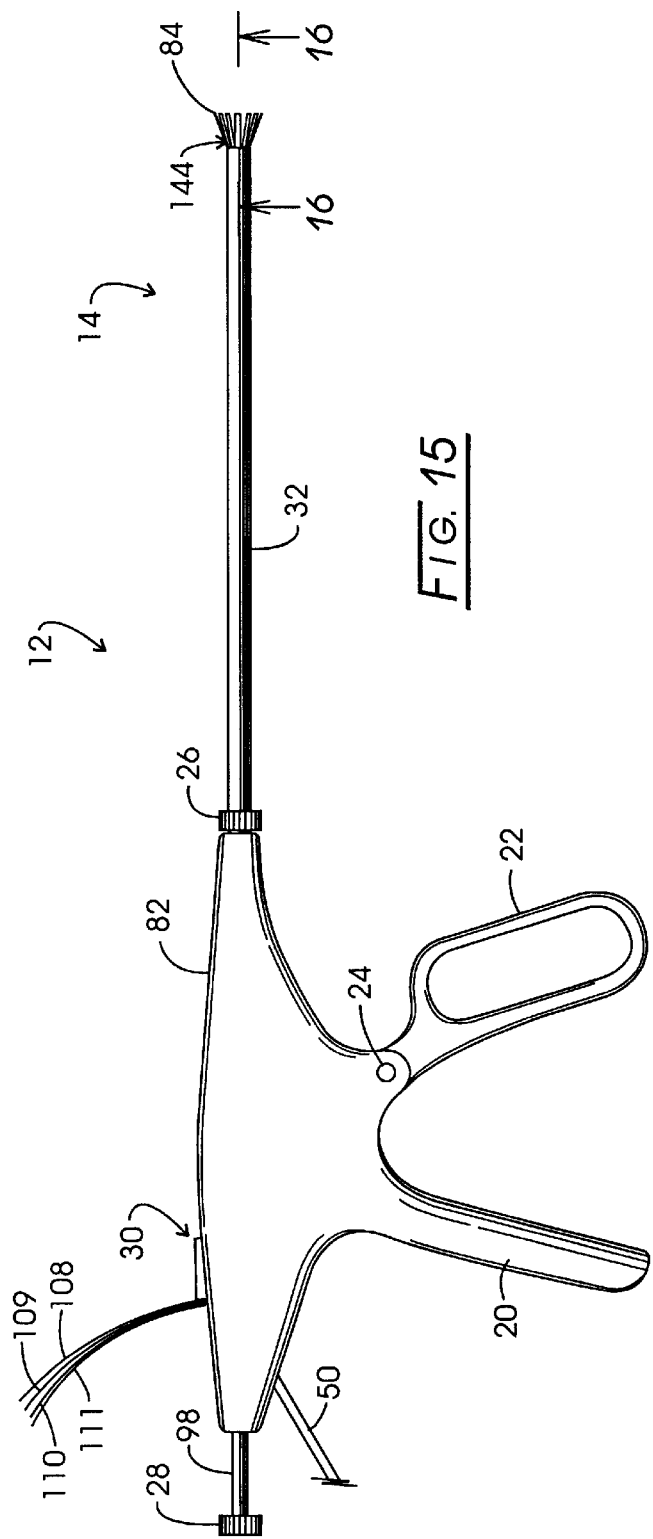
FIG. 15 is a side view of the instrument of FIG. 2 showing the retraction of a trocar.
Figure 16:
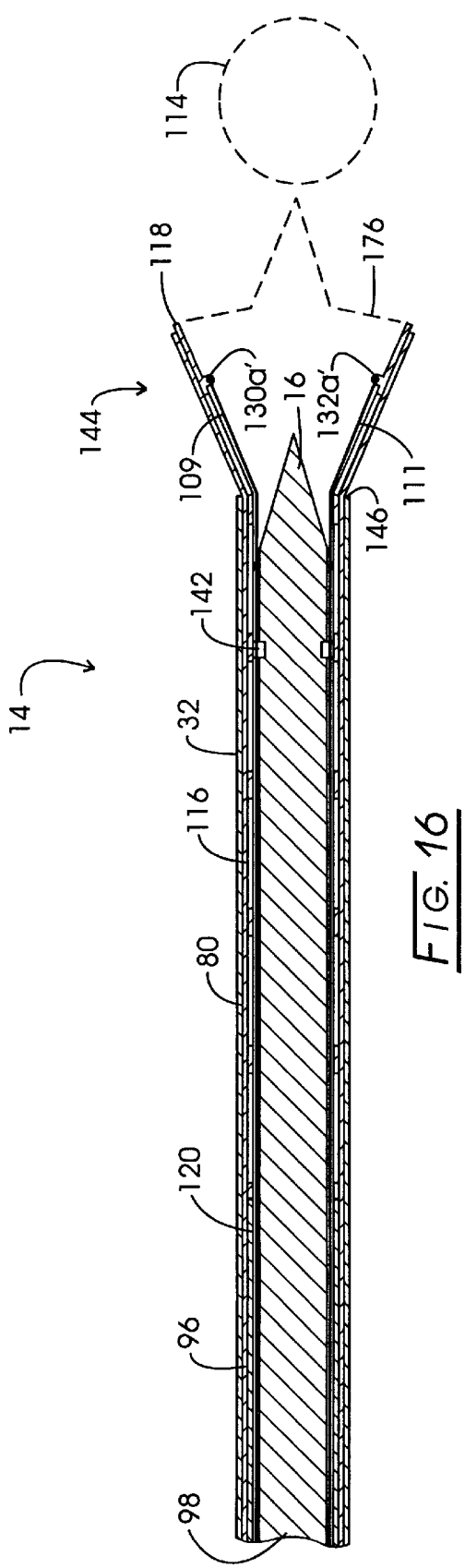
FIG. 16 is a sectional view taken through the plane 16—16 in FIG. 15.

FIGS. 15 and 16 illustrate the next step in the procedure. FIG. 15 reveals that handle 22 has been maintained in position, knob 26 has been retracted and knob 28 has been retracted to, in turn, retract trocar 98. FIG. 16 illustrates the retraction of the point 16 of trocar 98. The figure further shows that with this retraction, as well as the expansion of region 144 to conical form, will create a void in the tissue encountered, as represented by the dashed outline 176. As trocar 98 is retracted, no other components move and the elongate slots 102–105 slidably move along the respective pursing cables 108–111 (FIG. 3).

Following the retraction of trocar 98, the procedure continues with the electrical excitation of cutting components 130a–130d, 131a–131d, 132a–132d, and 133a–133d. This is carried out by actuating one foot pedal 60 or 62 of the foot switch 64 as described in connection with FIG. 1. As discussed in connection with FIG. 8, because of the electrically insulative coating applied to the capture component 116, only the blade tips 138 are actively energized to cause the electrosurgical cutting of tissue. Selection of one or the other of the foot pedals 60 or 62 is dependent upon whether a cut modality or a blend modality is elected by the surgeon. Utilization of the blend modality affords a greater degree of hemostasis driving the incision of tissue by the cutting components 130a–130d, 131a–131d, 132a–132d and 133a–133d. As shown in FIG. 17, as the blade tips are so excited to effect cutting of tissue, the actuator handle 22 is drawn inwardly towards the grip 20 to, in turn, urge drive tube 96 (FIG. 12) forwardly to cause the continued elastic expansion of capture component 116. In this regard, as revealed in FIG. 17, this expansion initially is in a conical form which continues until the outer peripheral dimension or diameter initially established, as discussed in connection with FIG. 11, is developed. As the electrosurgical cutting activity ensues, the practitioner rotates knob 26 back and forth through an angle of about 15° to accommodate for the spacing between adjacent cutting members at leading edge 18 of the capture component 116. Alternately, the practitioner may rotate the entire handle 18 back and forth through a small angle of about 15° to carry out this function.

Figure 19:
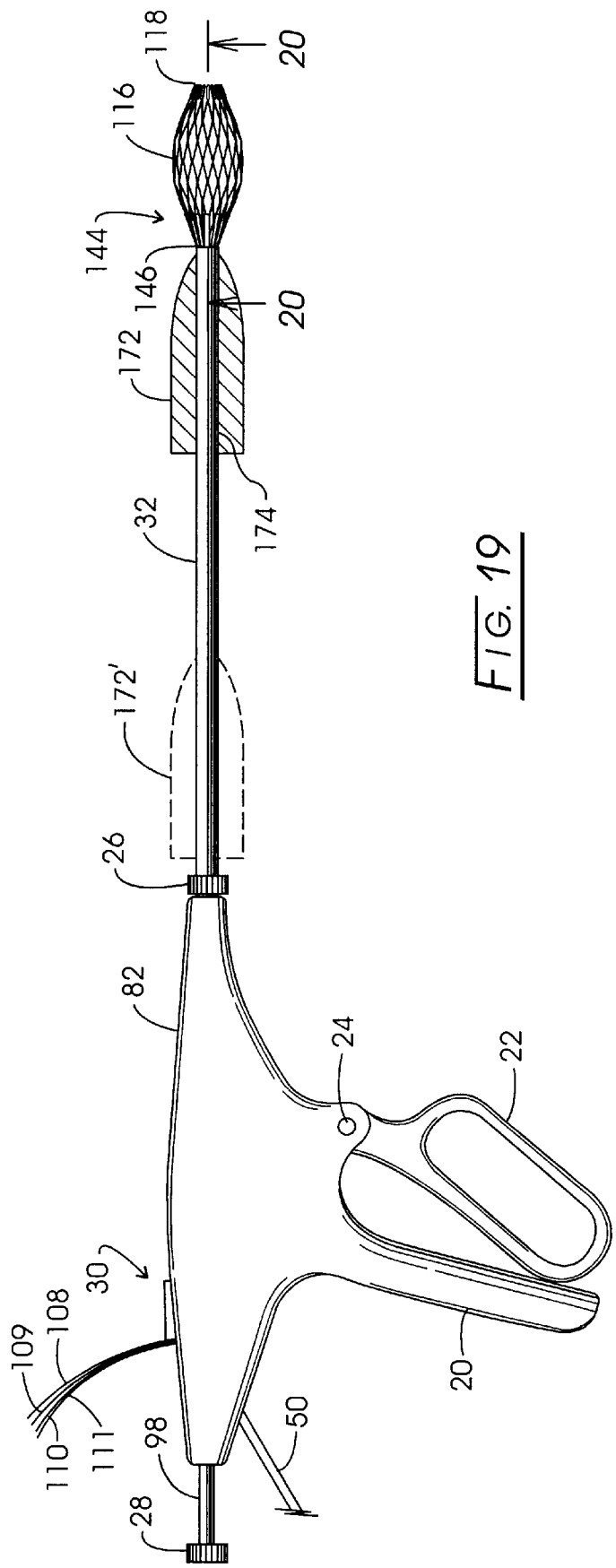
FIG. 19 is a side view of the instrument of FIG. 2 illustrating the completion of a capture component maneuver.
Figure 20:
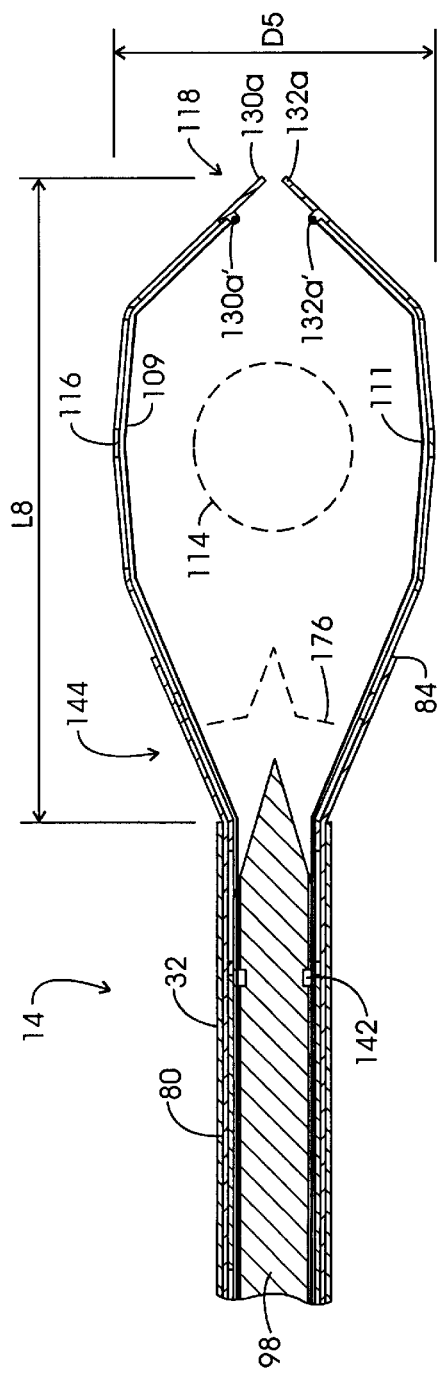
FIG. 20 is a sectional view taken through the plane 20—20 in FIG. 19.
Figure 21:
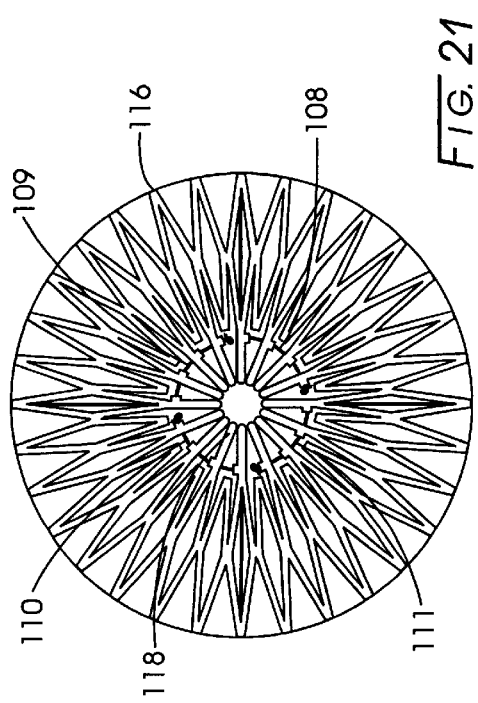
FIG. 21 is a side view of the capture component shown in FIG. 20.

As revealed in connection with FIG. 18, the leading edge 118 will move to a location adjacent or beyond the side of the targeted tissue volume 114 within adjacent tissue, a portion 178 of which will be encapsulated with the tissue volume 114. As this approach takes place, tension commences to occur at the pursing cables 108–111. As the leading edge 118 moves forward, now under the constraint of the pursing cables 108–111, the leading edge 118 is drawn inwardly toward the longitudinal axis 94 (FIG. 2) until the cutting members, as described at 138 in connection with FIG. 8, are converged into mutual adjacency as represented in FIGS. 20 and 21 to envelop the targeted tissue volume 114. FIG. 20 reveals that the targeted tissue volume 114 has been captured. The functioning of the pursing cable latch assembly 30 as described in connection with FIG. 12 now becomes apparent. By adjusting the length of the pursing cables 108–111 extending from the latch forwardly to capture component 116, the relative position at which capture component 116 closure commences and is completed, as described in conjunction with FIGS. 19, 20 and 21, can be controlled by the practitioner. Upon completion of capture, the output of generator 34 is terminated and the forward region 14 of the instrument 12 commences to be withdrawn from the tissue within which it is invested. In the course of this withdrawal, the cone-shaped forward region 144 functions, in effect, as a tissue dilator along the insertion puncture to enhance the progressive movement of the capture component 116 and the encapsulated tissue shown generally at 178 which surrounds and incorporates targeted tissue volume 114. As the region 144 approaches the region of the epidermis from within, the surgeon may cut the skin surface slightly to permit the final removal. Upon such removal, the pathologist may access the captured tissue volume 114 simply by cutting the pursing cables, whereupon the capture component 116 will release to the orientation described in connection with FIG. 18.

Practitioners may find it beneficial to incorporate an additional form of dilator with the instrument 12 for the purpose of facilitating the removal of capture component 116 following its envelopment of the tissue specimen. Such a dilator component particularly will facilitate removal of the capture component 116 where it is sized to remove relatively larger tumor or targeted tissue. FIG. 19 illustrates such a dilator device at 172. In general, device 172 is bullet-shaped and includes a central bore or channel 174 which slides over the outer surface of confinement sleeve 32. The device 172 is retained in a retracted orientation shown in phantom at 172' until such time as capture component 116 is removed. The component 172 preferably is formed of a medical grade plastic.

Figure 22A:
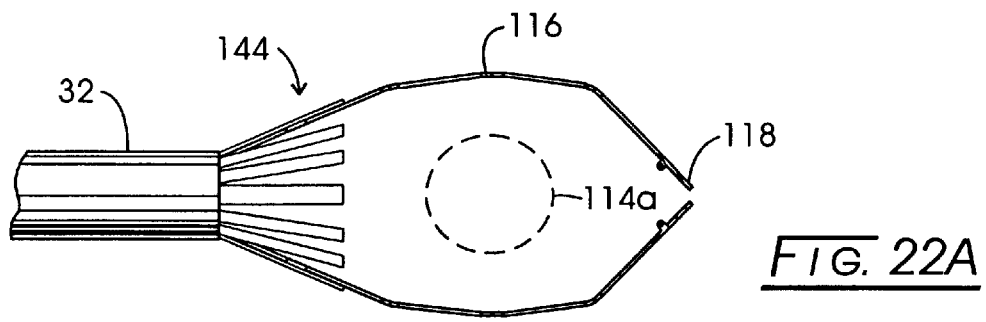
FIGS. 22A–22E illustrate the proportioning of a variety of sizes of instruments according to the invention.
Figure 22B:
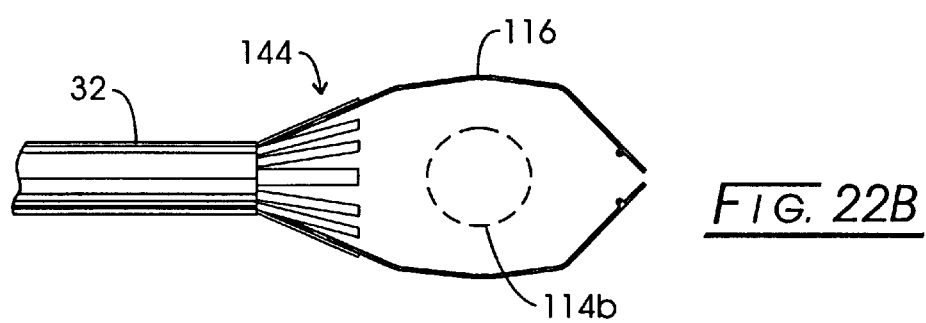
Figure 22C:
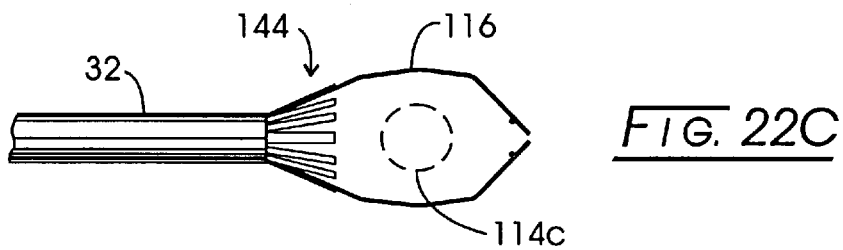
Figure 22D:
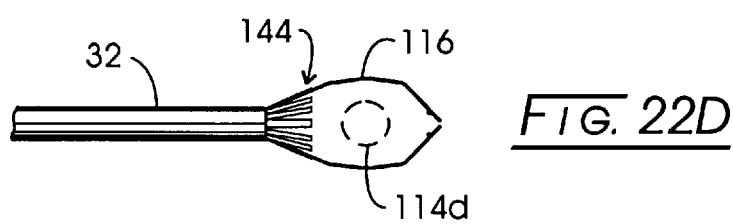
Figure 22E:
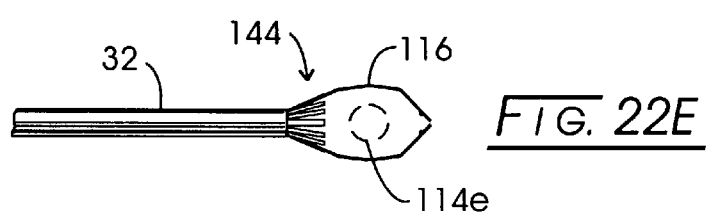

In the course of carrying out a biopsy procedure isolating and retrieving the targeted volume of tissue, the practitioner initially will access the size of the tumor or targeted tissue involved. Then, the least invasive instrument size is selected to carry out capture as described above. Accordingly, the instruments 12 are fabricated in a sequence of sizes related to the diameter of the outer periphery of an expanded capture component 116 and the corresponding outer diameter of the confinement sleeve. The former diameter is identified as $D_5$ in FIG. 20 and the latter is identified at $D_3$ in FIG. 14. The size of the tumor or targeted tissue also will determine the extruded length of the capture component 116 as identified at $L_8$ in FIG. 20. A representation of the relative proportioning of these components of the instrument 12 with respect to tumor size is represented in FIGS. 22A–22E. Differently sized tumors or target tissue again identified with the number 114 but with an alphabetical suffix corresponding with the figure identification. FIGS. 22A is representative of instrument 12 with an outer peripheral dimension or diameter of 40 millimeters. FIG. 22B illustrates the proportioning for an instrument 12 having a capture component released outer diameter of 30 millimeters. FIG. 22C is representative of an instrument having a capture component 116 outer periphery or diameter of 20 millimeters. FIG. 22D illustrates the relative proportioning of instrument 12 having a capture component 116 outer diameter of 15 millimeters. FIG. 22E illustrates the proportioning of an instrument 12 having a capture component 116 with an expanded outer periphery or diameter of 10 millimeters.

Figure 10:
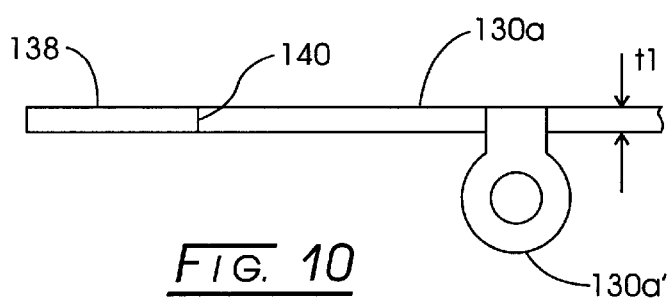
FIG. 10 is a side view of the cutting component of FIG. 9.
Figure 7:
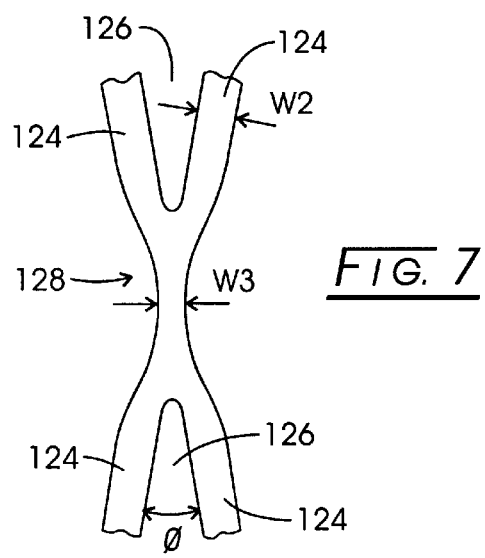
FIG. 7 is a partial plan view of the inter connection of struts within the captured component of FIG. 6.

Dimensions and angles have been symbolically represented in various of the figures. Preferred ranges for the dimensions and angles are set forth in the following tabulation. All dimensions shown in the tabulation are in inches. The parameter $t_1$, is represented at FIG. 10. The parameter $\phi_1$ is shown at FIG. 7. The parameter $\phi_2$ is shown at FIG. 14. The diameters $D_1$ and $D_2$ are shown in FIG. 8. The diameters $D_3$ and $D_4$ are shown in FIG. 14. The diameter $D_5$ is shown in FIG. 20. The width $W_1$ is shown in FIG. 8. The widths $W_2$ and $W_3$ are shown in FIG. 4. The width $W_4$ is shown in FIG. 8. The lengths $L_1$–$L_3$ are shown in FIG. 8. The lengths $L_4$–$L_6$ are shown in FIG. 6. The length $L_7$ is shown in FIG. 14, and the length $L_8$ is depicted in FIG. 20.

| Parameter | Range | Preferred Range |
| --- | --- | --- |
| $t_1$ | 0.001 to 0.030 | 0.005 to 0.020 |
| $\phi_1$ | 5° to 45° | 10° to 35° |
| $\phi_2$ | 10° to 75° | 15° to 60° |
| $D_1$ | 0.003 to 0.030 | 0.005 to 0.020 |
| $D_2$ | 0.013 to 0.060 | 0.015 to 0.040 |
| $D_3$ | 0.060 to 0.750 | 0.100 to 0.500 |
| $D_4$ | 0.050 to 0.700 | 0.090 to 0.480 |
| $D_5$ | 0.150 to 3.8 | 0.250 to 3.2 |
| $W_1$ | 0.005 to 0.050 | 0.010 to 0.030 |
| $W_2$ | 0.003 to 0.030 | 0.004 to 0.030 |
| $W_3$ | 0.002 to 0.030 | 0.003 to 0.020 |
| $W_4$ | 0.003 to 0.030 | 0.004 to 0.020 |
| $L_1$ | 0.004 to 0.030 | 0.006 to 0.020 |
| $L_2$ | 0.020 to 0.300 | 0.040 to 0.200 |
| $L_3$ | 0.010 to 0.150 | 0.015 to 0.060 |
| $L_4$ | 0.050 to 3.00 | 0.100 to 01.0 |
| $L_5$ | 0.40 to 15.0 | 0.500 to 10.0 |
| $L_6$ | 0.47 to 12.0 | 0.80 to 10.00 |
| $L_7$ | 0.100 to 2.0 | 0.150 to 1.50 |
| $L_8$ | .30 to 10. | 0.40 to 6.0 |

The instrument 12, as described above is a hand actuated one. However, typically, it is utilized in conjunction with imaging and guidance implements. While its insertion may be by direct visual placement, positioning through the use of stereotaxy, positioning based on previous imaging or upon real-time imaging are contemplated. In the latter regard, ultrasound, magnetic resonance imaging (MRI) or fluoroscopy may be employed. Imaging and positioning devices and approaches are described, for example, in the following publications:

(9) Jellins, J. "Current Concepts in Breast Ultrasound: Developments in Technology and Quality Assurance." *Mastology—Breast Diseases.* eds. A.S.S. Figueira Fo, et al. Amsterdam: Elsevier, 1995. 79–83.

(10) Stavros, A T and Dennis, M A. "An Introduction to Breast Ultrasound." *Percutaneous Breast Biopsy*. eds. Parker, S H et al. New York: Raven Press, 1993. 95–109.

(11) Daniel B L, et al. "Breast Lesion Localization: A Freehand, Interactive MR Imaging-guided Technique." *Radiology*. 1998; 207(2): 455–463.

(12) Gorczyca, D P, et al. "Wire Localization of Breast Lesions Before Biopsy: Use of an MR-Compatible Device in Phantoms and Cadavers." *Am. J. of Radiolocy* 1995; 165: 835–838.

The implementation of the invention represented by instrument 12 is one wherein the components of the instrument are entirely hand actuated. The instrument may also be implemented either fully or partially utilizing electromotive drives, gear systems and the like. A semiautomatic rendition of an instrument depicted generally at 180 is set forth in FIGS. 23 and 24. Reediting to FIG. 23, the forward portion of instrument 180, represented generally at 182, remains identical to the forward portion 14 of instrument 12. In this regard, a tubular confinement sleeve 184 is attached at its rearward end to a cylindrical knob 186. Knob 186 and its pin relationship with the delivery cannula 188 is identical to the arrangement shown in FIG. 3 in connection with knob 26, pin 92 and delivery cannula 80. FIG. 24 shows the longitudinal leg 190 of a slot represented generally at 192. Leg 190 corresponds with leg 90 as described in conjunction with FIG. 4. FIG. 23 shows a trocar 194 extending from a point 196 to rearward connection with a trocar retraction knob 198. Delivery cannula 188 is seen to extend into a housing 200 which may function as a handle. Knob 198 serves the same function as knob 28, providing for the step of manually retracting the trocar point 196. Not shown in the instant figures are the pursing cables as described earlier at 108–111 and their latched attachment to the housing 200 as described, for example, in connection with FIG. 12 at 30.

FIG. 24 reveals that the drive cannula 188 is journalled for rotation within a cylindrical bore 202 extending through the forward wall 204 of housing 200 and into an internal cavity 206. A driven gear 208 is fixed to cannula 188 within the cavity 206 and is shown meshed with a drive gear 210, in turn, mounted upon the shaft 212 of a stepper-type motor 214. Motor 214 is controlled to rotationally reciprocate the driven gear 208 to, in turn, rotate the cannula 188 in correspondingly reciprocal fashion through the earlier described angle of about 15°. Alternately, motor 214 may be controlled to rotate the driven gear 208 in a continuous clockwise or counterclockwise motion. The tubular cannula 188 terminates at an end 216 within cavity 206. Seen slidably extending from the end 216 is a drive tube 218 which corresponds to drive tube 96 as described in connection with FIG. 12. A collar or drive block 220 is attached to drive tube 218. Collar 220 includes a rack 222 which is driven forwardly by a pinion 224 mounted upon the shaft 226 of a stepper-motor 228. Extending from the end at 230 of drive tube 218 is the trocar shaft 194. The shaft 194 is seen to be slidably extending through a bore 232 within rear wall 234 of housing 200. As before, the rearward regions of both the trocar 194 and the drive tube 218 are coated with an electrically insulative layer such as the earlier-described Parylene.

Figure 25A:
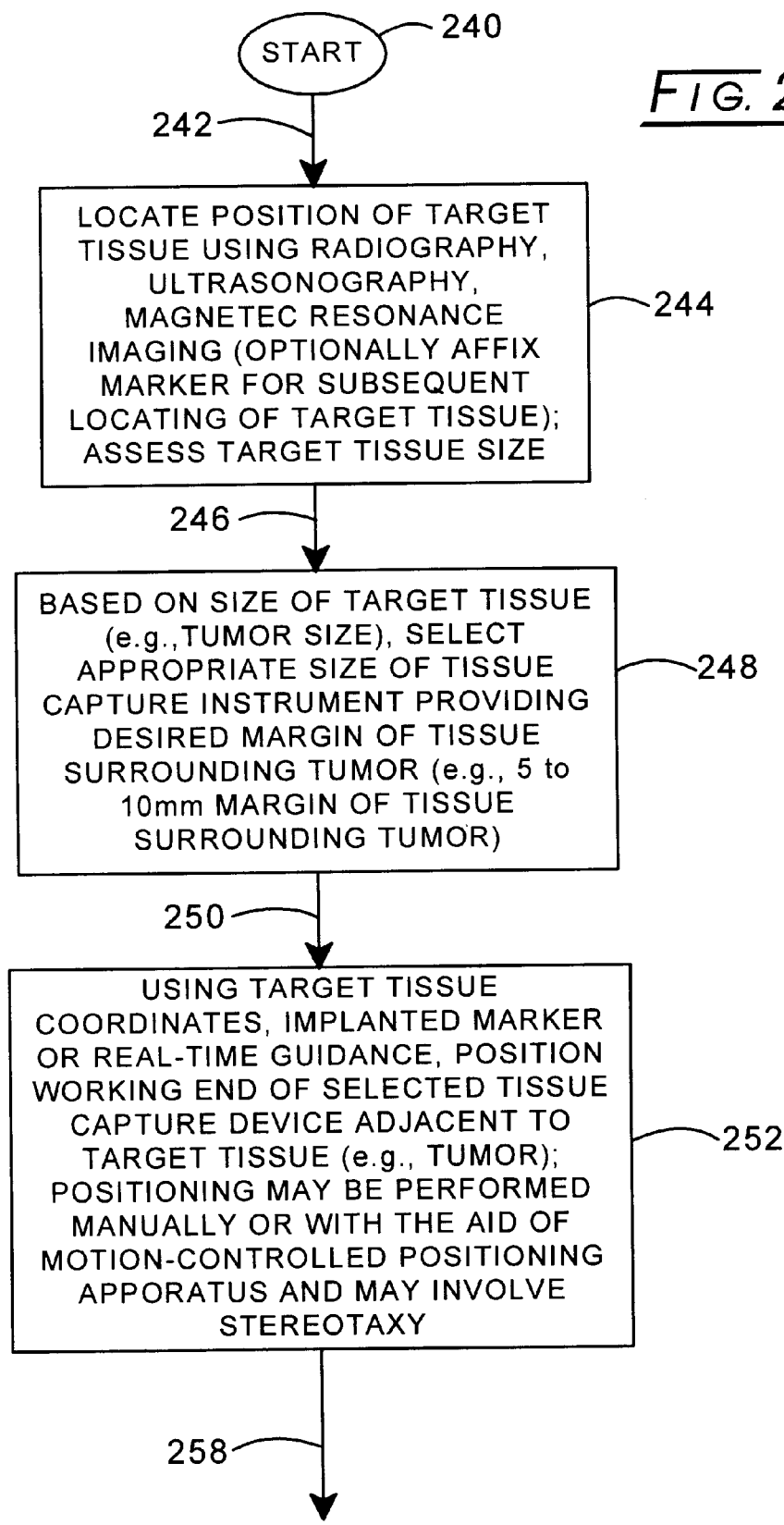

FIGS. 25A–25C combine as labeled thereon to provide a flowchart describing the method utilizing the system and apparatus of the invention. Referring to FIG. 25A, the method commences with start node 240 and, as represented at arrow 242 and block 244, the practitioner initially locates the position of the target tissue using radiography, ultrasonography, magnetic resonance imaging or the like. Optionally, the practitioner may affix a marker for subsequent location of the target tissue. During this procedure, the size of the target tissue is assessed or evaluated. The method then continues as represented at arrow 246 and block 248. At this step, based upon the size of the target tissue, the appropriate size of capture component 116 required is selected. In the course of the selection, the practitioner will provide a desired margin of viable or non-tumorous tissue about the targeted tissue to serve as a margin and assure that the total volume of targeted tissue is removed. For example, a 5 to 10 millimeter margin of tissue surrounding the targeted tissue volume may be removed. This encapsulated tissue has been identified generally at 178.

The method then continues as represented at arrow 250 and block 252. Using target tissue coordinates, and implanted marker or real-time guidance, the practitioner positions the working end of the instrument 12 in confronting adjacency with the target tissue. Such positioning may be performed manually or with the aid of motion-control positioning devices. The positioning also may involve stereotaxy. Then, as represented at arrow 254 and block 256 the confinement sleeve is retracted and secured, for example, employing knob 26 and slot 86. This permits the forward region of the delivery cannula as well as the leading edge of the capture component to expand into a funnel or cone shape. As represented at arrow 258 and block 260, the trocar is retracted, for example, employing knob 28 and the procedure continues. Then, as represented at arrow 262 and block 264, a foot pedal switch or the like is actuated to energize the cutting members or tip electrodes with an electrosurgical cutting or blend waveform while the tissue capture component is advanced and rotated to envelop the target tissue volume. Energy assisted cutting continues until the entire tissue volume is enveloped. This portion of the procedure includes the use of the pursing cables which commence to tension when the leading edge of the capture component is adjacent or beyond the side of the targeted tissue volume opposite that side which initially is confronted. Following such envelopment, as represented at arrow 266 and block 268, the foot pedal switch is released to stop application of the cutting or blend waveform. The method then continues as shown at arrow 270 which extends to dashed block 272 representing an alternate step in the procedure. For this procedure, with the depression of the switch of a control system, the cutting members or distal tip electrodes of the capture component are electrosurgically excited with either a cutting or blend waveform. As this occurs, an electromotive device or motion-control motors are activated to extend the tissue capture component following the retraction of the confinement sleeve. Automatic envelopment of the target tissue volume then is carried out until full envelopment is achieved, whereupon, the electrosurgical excitation of the cutting elements is terminated automatically. Another optional step may be carried out as represented at arrow 274 and dashed block 276. With this step, the earlier-described dilator may be slid forwardly to radially expand the tissue which spans the pathway between the capture tissue volume and the surface of the tissue, i.e., the skin surface. In general, this dilator is configured with a diameter corresponding with the anticipated diameter of the capture component following targeted tissue volume envelopment. Then, as represented at arrow 278 and block 280, the tissue capture component is removed from the body and the pursing cables at its leading edge are severed. The capture component then automatically springs open and the captured tissue volume is available for pathological examination. As represented at arrow 282 and node 284, the procedure then is ended.

A next embodiment of the invention utilizes a capture component which is configured such that the pursing cable itself functions as a wire type cutting electrode. Referring to FIG. 26, this instrument or apparatus is represented generally at 300. As before, the instrument 300 is configured with a delivery cannula represented generally at 302 which extends from a proximal end 304 (see additionally FIG. 32) to a forward region represented generally at 306. The cannula 302 is configured having an interior channel and is symmetrically disposed about a longitudinal axis 308. Delivery cannula 302 is secured at its proximal end 304 to a control and support assembly represented generally at 310. Assembly 310 includes a hand grip portion 312 and a finger loop-type hand actuator 314 which is configured to pivot about a pin connection at 316. An electrical cable 318 extends rearwardly from the assembly 310 and corresponds in function, for example, with cable 50 described in connection with FIG. 1.

Delivery cannula 302 extends forwardly to a distal end at 320 within forward region 306. That distal end 320 is positioned adjacent an electrically insulative guide assembly represented generally at 322 which functions to guide a capture component represented generally at 324, as well as to support a pointed trocar tip 326. Shown extending through the trocar tip 326 is the sharpened forward portion of an elongate hollow sampling needle 328 which may be utilized for carrying out a preliminary fine needle aspiration (FNA). The elongate needle 328 extends rearwardly through an elongate sampling channel within the assembly 310, the rearward portion of the needle being shown at 330 in connection with a component 332 of an aspiration assembly. For the instant embodiment, the apparatus 300 is configured having a capture component employing a singular pursing cable 334. The rearward portion of cable 334 is seen extending from assembly 310 and to be retained in position by a pivoting latch assembly represented generally at 336.

Instrument 300 may utilize a remote return electrode as described in connection with FIG. 1 at 54. Alternately, however, it may employ an electrosurgical return located within the forward region 306. Such a forwardly disposed return, representing an uninsulated surface of delivery cannula 302 is shown at 338.

Referring to FIG. 27, the interior channel of the delivery cannula 302 containing a capture component forward portion and components of a deployment assembly is revealed. In the figure, the trocar tip 326 is shown in confronting adjacency with targeted tissue such as a tumor or lesion symbolically represented within dashed boundary 340. Note that the sampling needle 328 has been advanced to a location where its point 342 is within the targeted tissue volume 340 for purposes of performing a preliminary fine needle aspiration prior to the electrosurgical deployment of the capture component 324. Following the carrying out of fine needle aspiration with the FNA needle 328, it is withdrawn.

The cylindrical inner channel 344 of the delivery cannula 302 is revealed in FIG. 27 as it extends into the forward region 306. Extending within this channel 344 and symmetrically disposed about the axis 308 is a cylindrical support component 346. Component 346 may be implemented for the instant embodiment as a polymeric rod or a metal rod, the surface of which is electrically insulated. The support component 346 also may be provided in tubular form. Support component 346 extends forwardly from assembly 310 to an annular shaped end surface 348 into which there is formed a cylindrical bore or receiving cavity 350. Mounted within the bore 350 is the cylindrical rearwardly depending post 352 of the generally cylindrically shaped internal guide member 354 of guide assembly 322. Internal guide member 354 extends to an annular forward surface 356 into which a rearwardly depending bore or trocar receiving cavity 358 is formed. Bore 358 receives the rearwardly depending cylindrical post 360 of trocar tip 326.

Looking momentarily to FIG. 28, the internal guide member 354 of guide assembly 322 is revealed as it is mounted upon the support component 346. Note that the cylindrical component 346 is configured having a sequence of six guide slots, three of which are revealed at 362a–362c. These six guide slots are arranged symmetrically about axis 308 upon 60° centers. Note that these guide slots 362a–362c extend within a curved guide portion or region represented generally at 366 which will be seen to promote the establishment of an angle of attack for the capture component. That angle of attack $\theta_3$ (FIG. 27) may, for example, be within a range of about 10° to 60° with respect to longitudinal axis 308. Preferably the angle of attack will be within a range of about 20° to 40° with respect to axis 308. The internal guide member may be formed of a polymeric material or of metal, the surface of which is selectively electrically insulated.

Returning to FIG. 27, extending around the internal guide member 354 is a generally cylindrically shaped outer guide member 368. Member 368 is configured having an annular shoulder 370 which abuttably rests upon the annular distal end surface 320 of delivery cannula 302. Extending inwardly from the shoulder 370 is a cylindrical support portion 372 which nests against the surface of the internal channel 344 of delivery cannula 302 and is attached thereto. Forwardly of the shoulder 370, the outer guide member 368 is configured having an angle of attack defining capture component guide region 374 which cooperates with the slots as at 362a–362c (FIG. 28) to define guideways functioning to cause the capture component to move outwardly at the noted angle of attack, $\theta_3$. A longitudinally disposed slot 376 is formed within outer guide member 368 to slideably receive pursing cable 334. That pursing cable 334 is shown extending along a longitudinal slot 378 performed within the outer surface of support component 346. Note, additionally, that the component 346 incorporates an elongate sampling channel 380 for slidably receiving the sampling needle 328. The delivery cannula 302 generally is formed of stainless steel, particularly when the instrument is configured to provide the return 338 at forward region 306. To define that return 338, the stainless steel delivery cannula is covered with an electrically insulative polymeric shrink wrap represented at 332.

Looking additionally to FIG. 29, the capture component 324 is seen to be configured as an elongate, stainless steel tube which is electrically insulated, for example, with the earlier noted Parylene. FIG. 27 reveals that capture component 324 is slidably positioned upon support component 346. The forward region 390 of capture component 324 is configured having a plurality of discrete, elongate cage defining leafs which are formed within the stainless steel tube, for example, by laser cutting. FIG. 29 reveals three of these leafs 392a–392c. The leading edge portion 394 of capture component 324 is configured as a series of eyelets 396a–396f which are twisted 90° with respect to the surface of their associated leafs. A developed view of the capture component 324 is revealed in FIG. 30. This view illustrates that one of the leafs, identified at 396f is configured having a centrally disposed longitudinally oriented slot 398. Slot 398 is part of a configuration provided for the purpose of supporting the pursing cable 334. Looking to FIG. 31, leaf 392f is revealed in sectional detail showing elongate slot 398 retaining a polymeric, electrically insulative tube 400 within which pursing cable 334 is slidably located. The slot 398 along with tube 400 is enclosed by a thin, electrically insulative shrink wrap 402. Note in FIG. 30 that the shrink wrap 402 extends from a proximal location 404 corresponding with the forward end of slot 378 (FIG. 27) to a distal location 406 just behind the terminus of the forward end of slot 398. Pursing cable 334 exits from this forward portion of slot 398, whereupon it is threaded through eyelet 396d. Upon being threaded through eyelet 396d, it is then threaded through the remaining eyelets and finally tied off within a tying aperture 408.

Returning to FIG. 27, it may be observed that leafs at the leading edge portion 394 of capture component 324 are engaged within slots certain of which were described at 362a–362c in FIG. 28 and each leaf 392a–392f is caused by the geometry of the slots to curve outwardly at the attack angle, $\theta_3$. To improve this transverse guidance, support component 346 and the associated internal guide member 354 are spring biased rearwardly along longitudinal axis 308.

The trocar tip 326 optionally may be utilized as a return electrode for the purpose of confining current flow to the region about the encapsulating tissue volume being captured. For such an arrangement, the support component 346, internal guide member 354 and trocar tip 326 are formed of an electrically conductive material such as stainless steel. It may be recalled that the capture component is coated with an electrically insulated Parylene such that it is immune from electrical contact with support member 346.

For the instant embodiment, electrical cutting and coagulating current is supplied to the pursing cable 334 from the electrically insulated leafs 392a–392f by virtue of a circuit completing contact with these leafs at the eyelets 396a–396f. Accordingly, the pursing cable is not insulated at that forward region.

Figure 32:
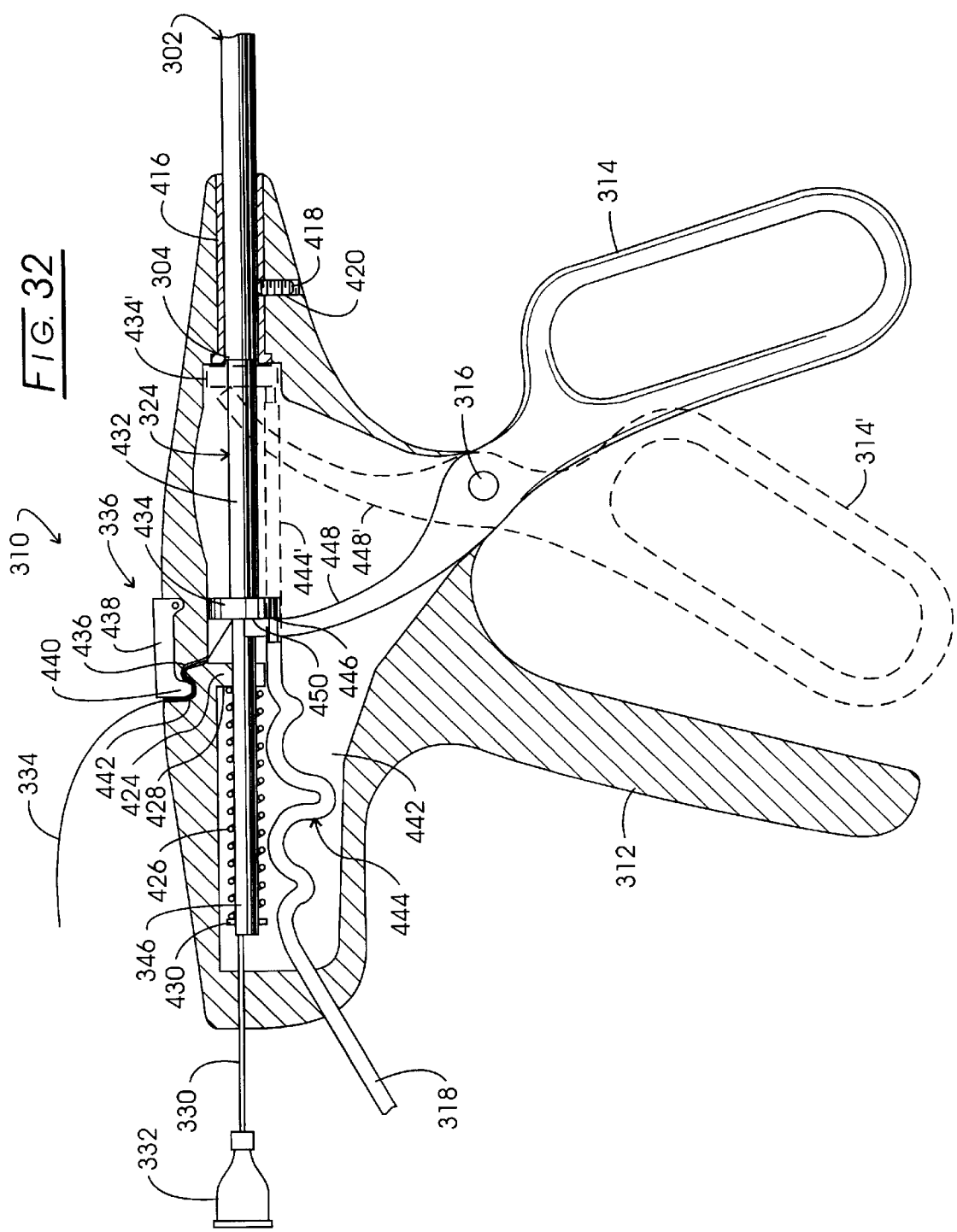
FIG. 32 is a partial sectional view of the control and support assembly of the instrument of FIG. 26.

Referring to FIG. 32 the control and support assembly 310 along with certain deployment assembly components are revealed in sectional detail. In FIG. 32, delivery cannula 302 is seen inserted within the open cylindrical interior of a support bushing 416. A set screw 418 within a threaded bore 420 functions to lock the delivery cannula 302 into engagement with control and support assembly 310. Extending from the inner channel 344 of delivery cannula 302 is the earlier-described elongate support component 346. The cylindrically shaped component 346 is seen to extend within a cavity 422 and is slidably supported by a downwardly depending protrusion 424 integrally formed with the assembly 310. As noted above, the support component 346 is rearwardly biased along longitudinal axis 308. That bias is imposed by a helical spring 426 disposed about the outer surface of component 346 and restrained between one face 428 of protrusion 424 and a transverse stop rod 430 extending through support component 346 adjacent its rearward end.

Slidably positioned over support component 346 is the rearward tubular portion 432 of capture component 324. The end of tubular portion 432 is fixed to and in electrical communication with a cylindrical drive cam 434. Extending from the elongate slot 378 (FIG. 27) is the pursing cable 334 which is seen to be threaded through a slot 436 forming a portion of the latch assembly 336. Cable 334 is retained in position by a lever arm 438 having a dog component 440 engaging a notch 442 within the assembly 336.

In the present embodiment, electrical cutting and coagulating current is supplied to the capture component 324 at its rearward region 432 from cable 318. The lead carrying these currents is provided slack for movement at 444 and is attached to the cam component 434 at attachment terminal 430.

Hand actuator 314 extends from its pivoted connection 316 into the cavity 422 with a bifurcate drive lever 448, the two spaced apart tips of which freely abuttably engage the rearward face 450 of drive cam 434. With the arrangement shown, when the actuator handle 314 is drawn rearwardly toward grip 312 as represented in phantom at 314', the drive lever 448 serves to push the cylindrical drive cam 434, and thus capture component 324, forwardly as represented at 448' and 434'. Cable slack portion 444 also is drawn forwardly as represented at 444'.

For the electrical connections shown in FIG. 32, the apparatus 300 is configured for monopolar electrical excitation utilizing a remote electrode as shown at 54 in FIG. 1. However, where the forward region 306 (FIG. 26) of delivery cannula 302 as at 338 is employed as an electrical return, then return connection is made within the control and support assembly 310 between a return lead and delivery cannula 302. Correspondingly, when the trocar tip component 326 (FIG. 27) is employed as the local return, then a return lead is coupled to support member 346, it being recalled that essentially all surfaces of the capture component 324 are electrically insulated, for example, with Parylene.

As the hand actuator 314 is pulled toward grip portion 312, electrosurgical cutting current is applied to the capture component 324. This cutting current is electrically conveyed to the bare (uninsulated) portion of pursing cable 334 from the eyelets 396a–396f.

Figure 33:
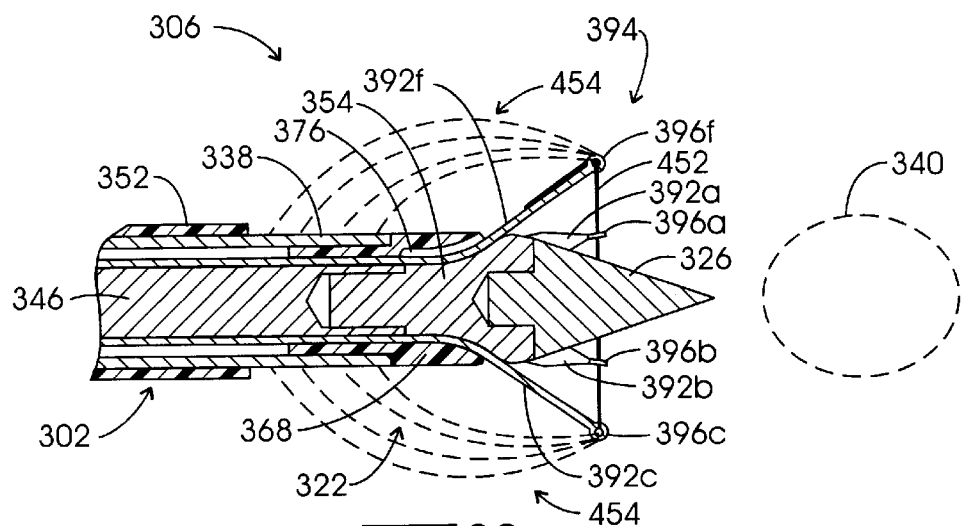
FIG. 33 is a partial sectional view of the forward region of the instrument of FIG. 26 arranged in a confronting orientation with respect to a symbolic targeted tissue, the figure further showing current path lines to a delivery cannula borne electrosurgical return.

Looking to FIG. 33, the commencement of this deployment of the capture component leafs through the guidance slots defined between mutually biased together internal guide member 354 and outer guide member 368 of guide assembly 322, is illustrated. In the figure, leafs 392f and 392c, in particular, are seen extending into an encapsulating tissue volume at the predetermined attack angles, $\theta_3$. The trocar tip 326 will have been positioned within such tissue in confronting relationship with the targeted tissue 340. For the instant illustration, the sampling needle 328 and associated channel 380 are not illustrated and the wire type cutting electrode portion of pursing cable 334 is shown at 452. Further illustrated are the current paths represented by dotted line array 454 which will be generated for the embodiment wherein a return electrode is developed at region 338 of delivery cannula 302. Note that the current path represented at array 454 is substantially confined to the region of tissue adjacent forward region 306. As the electrosurgical cutting activity with cable portion 452 ensues, the practitioner releases pursing cable 334 from its latched engagement at latch assembly 366. This existing friction between cable 334 and the surfaces adjacent to its path from control and support assembly 310 to the forward end during the play-out of the cable permits the electrode defining portion 452 thereof to remain sufficiently tensioned for carrying out appropriate tissue cutting. FIG. 33 shows that the cutting cable portion 452 is approaching one side of targeted tissue 340 but is within the surrounding encapsulating tissue to provide a margin of severed healthy tissue about targeted tissue 340 which ultimately is captured (encapsulated) and removed.

Figure 34:
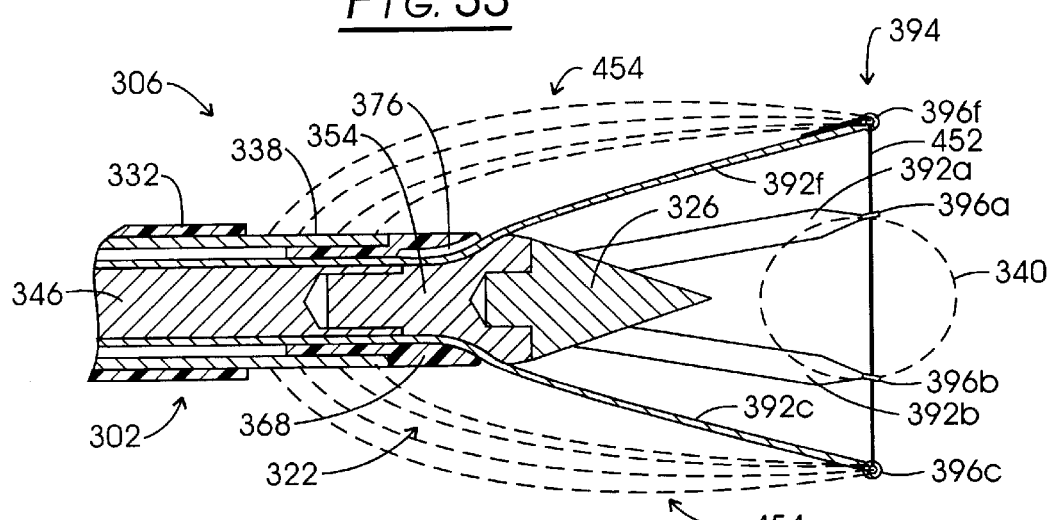
FIG. 34 is a partial sectional view of the instrument of FIG. 33 showing a next later stage in the capture of encapsulating tissue and showing current path lines to a delivery cannula borne electrosurgical return.

Referring to FIG. 34, leafs 392a–392c and 392f, as well as the remaining leafs are further deployed and the cutting cable 452 is seen to cut within the encapsulating tissue and is commencing to approach the opposite side of targeted tissue 340. Typically, at this orientation, the pursing cable 334 is held stationary as forward region 390 continues to move forwardly.

Figure 36:
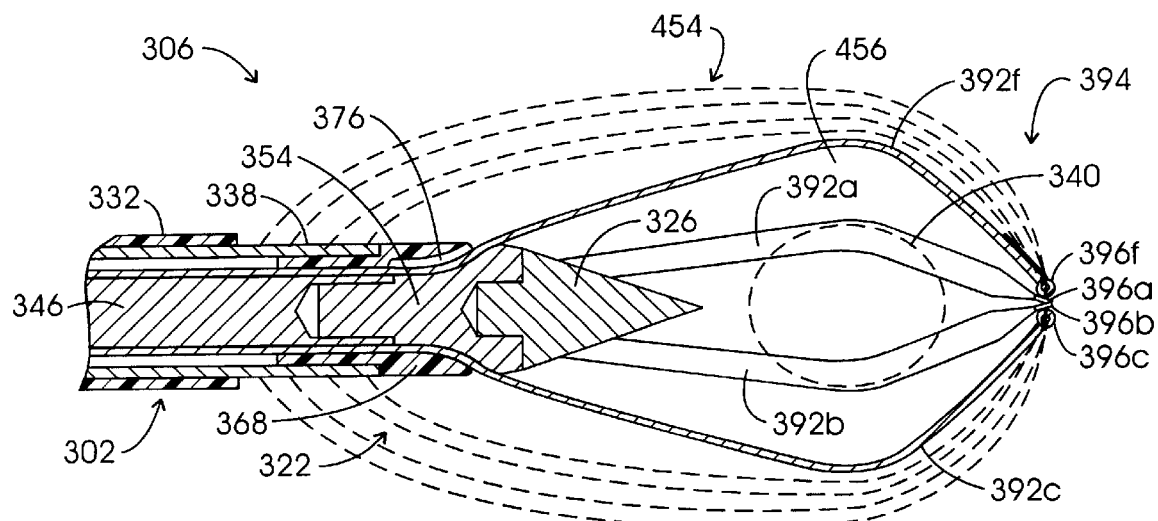
FIG. 36 is a partial sectional side view of the instrument of FIG. 34 showing the capture and isolation of an encapsulating tissue volume.
Figure 37:
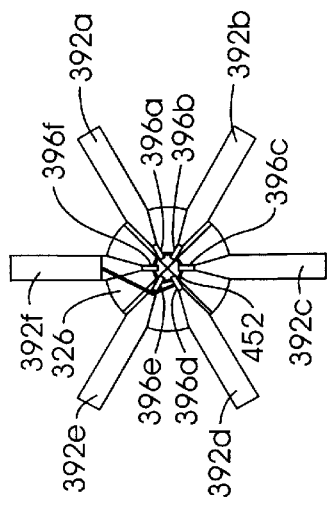
FIG. 37 is a front view of the capture component shown in FIG. 36.
Figure 35:
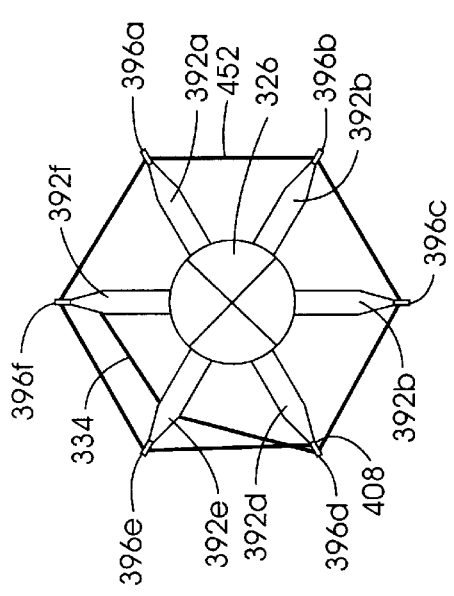
FIG. 35 is a front view of the capture component shown in FIG. 34.

Looking momentarily to FIG. 35, the cutting shape of the tensioned cable portion 452 is revealed at this maximum deployment configuration. At this point in the procedure, pursing cable 334 extending from the latch assembly 336 is either held stationary or slightly retracted by the practitioner to an extent effecting a pursing or contraction of the leading edge portion 394 of the capture component. Preferably, the pursing cable 334 is held stationary by the practitioner when it is approaching the opposite side of the targeted tissue 340 (FIG. 34). In a next embodiment this contraction maneuver is automatically carried out. However, where withdrawal (here, manual) of the cable 334 from the latch assembly 336 is available, the leading edge portion 394 can be maneuvered past the opposite side of the targeted tissue 340 and then abruptly contracted by pulling on the pursing cable 334. A preferred form of maneuver of the leading edge 394 is represented in FIG. 36 where contraction commences and is gradually carried out from the orientation of FIG. 34. Note in FIG. 36 that an encapsulated tissue volume 456 has been enveloped, isolated and captured. Note additionally, that the current paths represented by dashed line array 454 are outside of that encapsulated tissue volume 456 as they extend to the local return electrodes 338. The figuration of capture component leafs 392a–392f upon the contraction represented at FIG. 36 is shown in FIG. 37. Note that the eyelets 396a–396f at the leading edge 394 are drawn into close adjacency to the extent that the encapsulated tissue 456 will be completely severed away or isolated. At this point in time in the procedure, cutting current delivery to the cable portion 452 is terminated and withdrawal of the now isolated encapsulated tissue volume 456 with the targeted tissue 340 is commenced.

Figure 38:
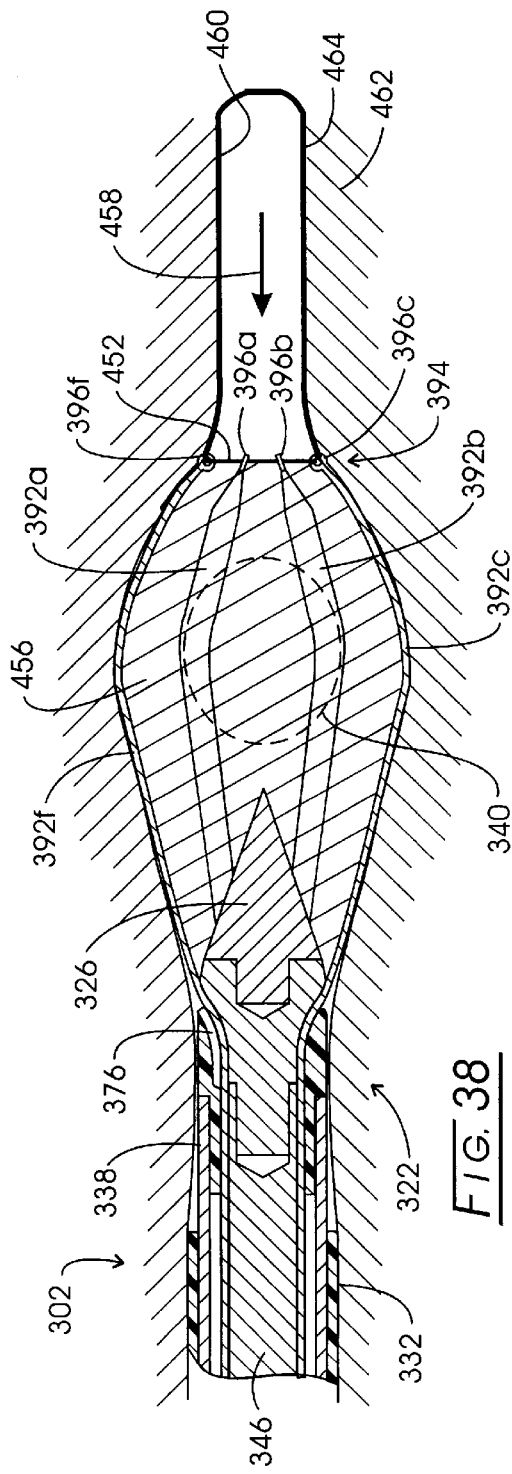
FIG. 38 is a partial sectional view of the instrument of FIG. 33 showing its removal from tissue while applying white coagulation current and voltage to the cutting cable associated therewith.

With the instant system, the practitioner is provided an optional procedure for carrying out white coagulation at the cutting cable portion 452 during the withdrawal activity. This will cause a cell necrosis along the tissue pathway of removal to provide a control over any possible seed metastasis. The latter phenomena, for example, may be occasioned with the utilization of the sampling needle 328 as a preliminary step in the procedure. FIG. 38 illustrates this withdrawal approach. In the figure, pursing cable 334 will have been released slightly to, in turn, slightly enlarge the otherwise constricted opening at leading edge portion 394. In the figure, the direction of withdrawal is represented at arrow 458 and along the pathway of withdrawal 460 within tissue 462 there is evolved a thickness of cell necrosis represented at 464 which is established by the selection of white coagulation current as well as the rate of removal of the instrument from tissue.

Figure 39:
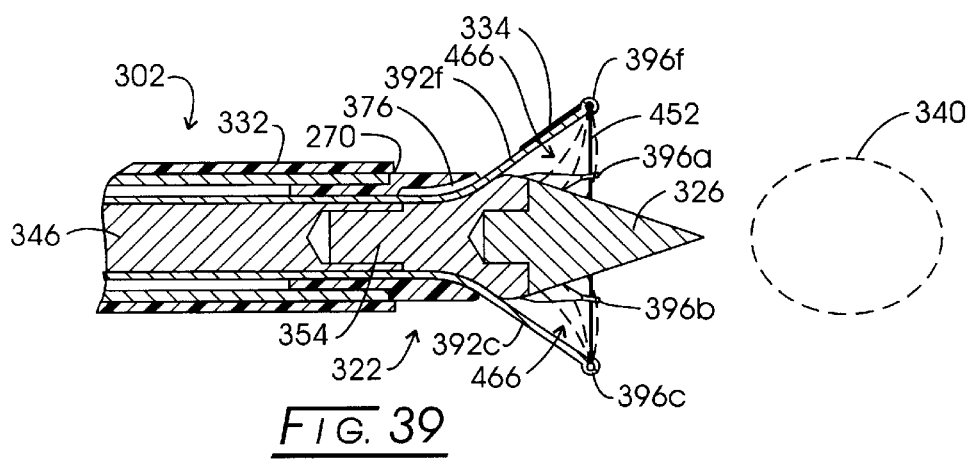
FIG. 39 is a partial sectional view of the forward region of an instrument according to the invention showing an implementation wherein a forward trocar is employed as an electrosurgical return and showing resultant current paths from a cutting electrode to the return.
Figure 40:
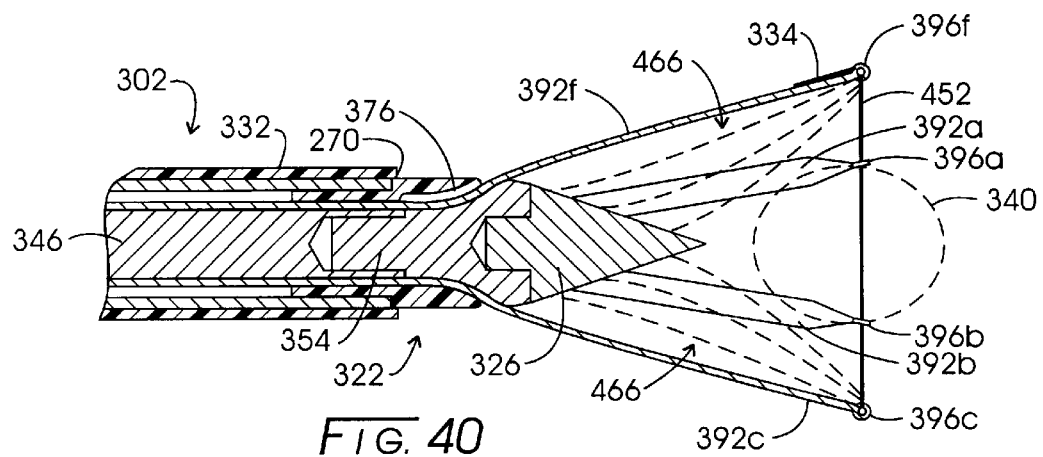
FIG. 40 is a partial sectional view of the instrument of FIG. 39 showing a next stage in the procedure of electrosurgically cutting and isolating an encapsulating tissue volume and showing developed current paths.
Figure 41:
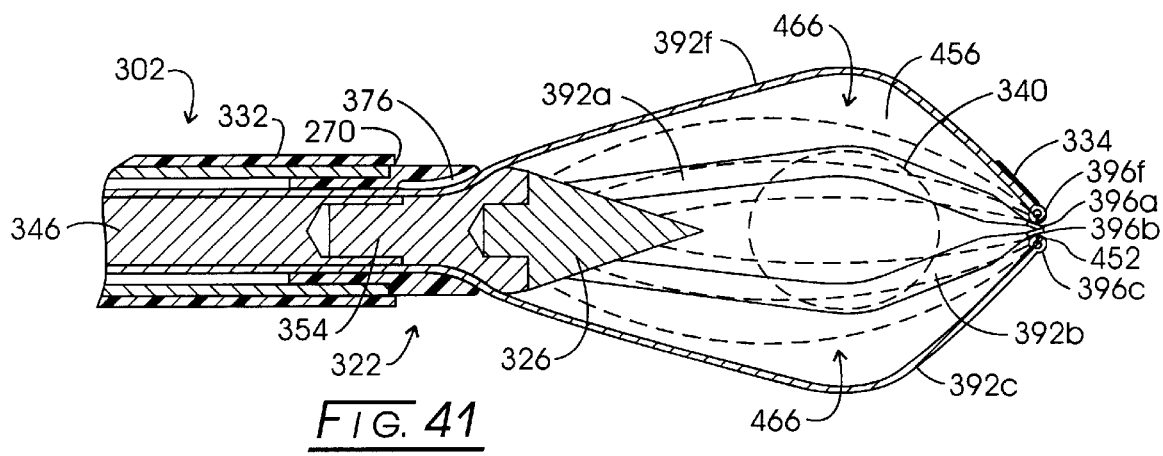
FIG. 41 is a partial sectional view of the instrument of FIG. 39 showing a completion of the isolation of an encapsulating tissue volume and further showing current flow paths at final contraction of a capture component.

In instrument configurations wherein the trocar tip 326 is provided as the electrosurgical return, current paths between the cutting electrode cable portion 452 and the electrosurgical return become shorter. As noted above, the trocar tip 326 can be coupled as a return by forming the trocar tip 326, internal guide component 354 and support component 346 of metal. A return input to the electrosurgical generator then is coupled to the latter support component. FIGS. 39 through 41 illustrate the same capture and isolation procedure as discussed above in connection with FIGS. 33, 34 and 36. However, the desirably shortened current paths between the cable provided cutting electrode 452 and the return trocar tip 326 electrode now are illustrated as dashed line arrays 466.

In the embodiment set forth in connection with FIGS. 26–41, a singular, manually controlled pursing cable has been described as being employed in connection with a capture component. To accommodate for electrosurgical current, the pursing cable was excited from the tips of the capture component leafs. In the embodiments to follow, added pursing cables are employed with an arrangement for the automatic tensioning of them at the appropriate procedural point in time to cause the contraction of the capture component leading edge. Through the use of additional pursing cables, the length of cable required for this contracting activity is reduced proportionately. Because of the added cross section represented by the additional cables, they can be excited from the rearward portion of the assembly with electrosurgical cutting and coagulation current.

Figure 42:
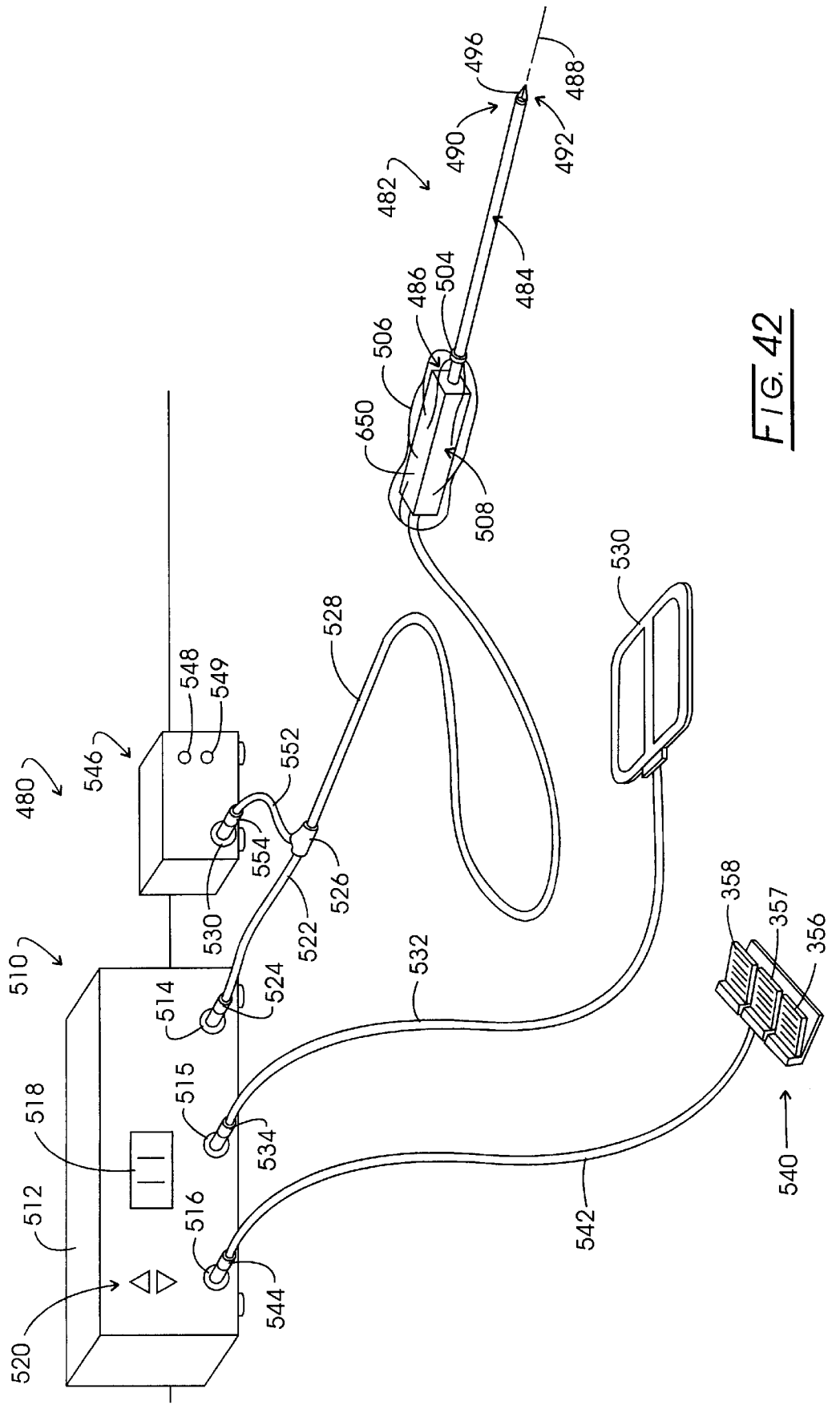
FIG. 42 is a perspective view of another embodiment of the system of the invention.

Referring to FIG. 42, a system according to the invention incorporating a motorized deployment feature is represented generally at 480. System 480 includes a tissue isolation and retrieval instrument or apparatus represented generally at 482. Looking additionally to FIG. 43, the instrument 482 is seen to be configured with a delivery cannula represented generally at 484 which extends from a proximal end portion 486 along a longitudinal axis 488 to a forward region 490. The distal end of the delivery cannula 484 is shown at 492 being implemented, for the instant embodiment, with a trocar tip 496. FIG. 43 reveals the leading edge portion 498 of a capture component and immediately rearwardly thereof is a capture component guidance assembly represented generally at 500. Next in rearward adjacency with the assembly 500 and within the forward region 490, is a return electrode 502 which is provided as the outer cylindrical surface of delivery cannula 484. Positioned forwardly of the proximal end portion 486 of delivery cannula 484 is a shroud collar 504 to which is attached a protective sterile shroud 506 formed of a polymeric sheet material. Collar 504 and shroud 506 are shown in phantom outline in FIG. 43. Delivery cannula 484 is supported physically and functionally by a control and support assembly represented generally at 508. Shroud collar 504 and sterile shroud 506 function as a feature of the instrument 482 wherein the delivery cannula 484 and components attached to it are disposable and interconnect with the assembly 508, which is reusable. The shroud 506 permits sterile field use of the re-usable assembly 508.

As in the earlier embodiments, the leading edge portion 498 of a capture component carries out electrosurgical cutting, isolation, capture and coagulation functions. Accordingly, the system 480 includes an electrosurgical generator represented generally at 510 in FIG. 42. Generator 510 incorporates a front panel 512 at the lower level of which are provided three connector receiving receptacles 514–516. A menu driven display is provided at 518 which performs in conjunction with an up-down switch button assembly represented generally at 520. A communications and power branch cable 522 having a connector 524 is electrically coupled with connector 514 and is seen to extend to a cable combiner 526 and thence through a main cable 528 to connection with control and support assembly 508. Instrument 482 may perform in a quasi-bipolar fashion employing a return electrode at forward region 490 or in a conventional monopolar fashion while carrying out electrosurgical cutting and coagulation. An approach to developing a return for the latter form of cutting and coagulation involves the utilization of a remote patient return electrode as represented at 530 in phantom. Such a return is employed when utilizing an electrosurgical precursor lancet electrode in accordance with one embodiment of the invention. Return electrode 530, having an extended surface area is applied to a surface of the patient's body and is seen connected to the electrosurgical generator 510 by a cable represented in phantom at 532 extending to a connector represented in phantom at 534. Connector 534 is coupled to connector 515 of the generator 510.

Upon power-up, the generator 510 will provide an output at branch cable 522 and main cable 528 by depressing an appropriate footpedal at 536–538 of a switch assembly represented generally at 540. Assembly 540 includes a cable 542 having a connector 544 shown in electrical communication with generator 510 connector 516. In general, the actuation of footpedal switches 536 and 537 will provide an electrosurgical cutting output, while actuation of switching foot pedal 538 will develop a white coagulation output from the generator 510. Of course, this triple switching function may be provided as a switch assembly mounted upon generator 510 or upon the control and support assembly 508 of instrument 482. Shown additionally in FIG. 42 is a motor control console represented generally at 546 having on and off switches at 548–549 and an electrical connector 550. Connector 550 is shown coupled with a branch cable 552 to a branch cable connector 554. Branch cable 552 extends through cable combiner 526 to main cable 528 and thence to assembly 508. In one arrangement of the invention, actuation of a captive component drive motor within housing 508 along with conveyance of cutting current takes place in conjunction with the depression of footpedal switch 536, while actuation of footpedal switch 537 applies cutting current to a lancet electrode. Returning to FIG. 43, as in the earlier embodiments, the apparatus 482 includes an auxiliary channel extending therethrough in generally parallel relationship with the axis 488 from an access port located at 560 to an exit opening located at 562. A sampling needle 564 having a point 566 is seen to be slidably extending through the auxiliary channel, the rearward terminus 568 of which is seen coupled with a component 570 of an aspiration assembly.

Referring to FIG. 44, the interior channel of the delivery cannula 484 containing a capture component forward portion and components of a deployment mechanism assembly is revealed. In the figure, the trocar tip 496 is shown in confronting adjacency with targeted tissue such as a tumor or lesion symbolically represented within dashed boundary 570. Note that the sampling needle 564 has been advanced to a location where its point 566 is within the targeted tissue 570 for purposes of performing a preliminary fine needle aspiration (FNA) prior to the electrosurgical deployment of the capture component now nested within the instrument 482. Following the carrying out of fine needle aspiration with the FNA needle 564, it is withdrawn.

The cylindrical inner channel 572 of the delivery cannula 484 is revealed in FIG. 44 as it extends into the forward region 490. Extending within this channel 572 and symmetrically disposed about axis 488 is a cylindrical support component 574. Component 574 incorporates a portion of the auxiliary channel 576 which is employed, for the instant embodiment, to slidably receive the sampling needle 564. As before, it may be configured as a tube. Component 574 extends forwardly from support assembly 508 to an annular shaped end surface 578 into which there is formed a cylindrical bore or receiving cavity 580. Mounted within the cavity 580 is the cylindrical rearwardly depending post 582 of the generally cylindrically shaped internal guide member 584 of guide assembly 500. Internal guide member 584 extends to an annular forward surface 586 into which a rearwardly depending bore or trocar receiving cavity 588 is formed. Cavity 588 receives the rearwardly depending cylindrical post 590 of trocar tip 496. Looking momentarily to FIG. 45, the internal guide member 584 of guide assembly 500 is revealed as it is mounted upon the support component 574. Note that the cylindrical component 584 is configured having a sequence of six guide slots, three of which are revealed at 592a–592c in FIG. 45. These six guide slots are arranged symmetrically about axis 488 on 60° centers. Note that these guide slots 592a–502c extend within a curved guide portion or region represented generally at 594 which will be seen to promote the establishment of an angle of attack for the capture component leafs, such angle having been earlier described as, $\theta_3$. Of interest for the present embodiment, however, is the presence of three cable guide slots centered within three symmetrically disposed ones of the leaf guide slots. In this regard, note that a cable guide slot 596b is formed within the center of guide slot 592b and extends in parallel with longitudinal axis 488 within guide support 574. Three such cable guides slots are provided symmetrically disposed upon 120° centers. Internal guide member 584 may be formed of a polymeric material or metal depending upon whether the trocar tip 496 is utilized as a return electrode. Where the tip 496 is used as a return electrode, then the member 584 is formed of a metal with surfaces selectively electrically insulated. The same conductivity criteria applies with respect to support component 574.

Returning to FIG. 44, extending around the internal guide member 584 is a generally cylindrically shaped outer guide member 598. Member 598 is configured having an annular shoulder 600 which abuts against the annular distal end surface 494 of delivery cannula 484. Extending inwardly from the shoulder 600 is a cylindrical support portion 602 which nests against the surface of the internal channel 572 of delivery cannula 484 and is attached thereto.

Figure 48:
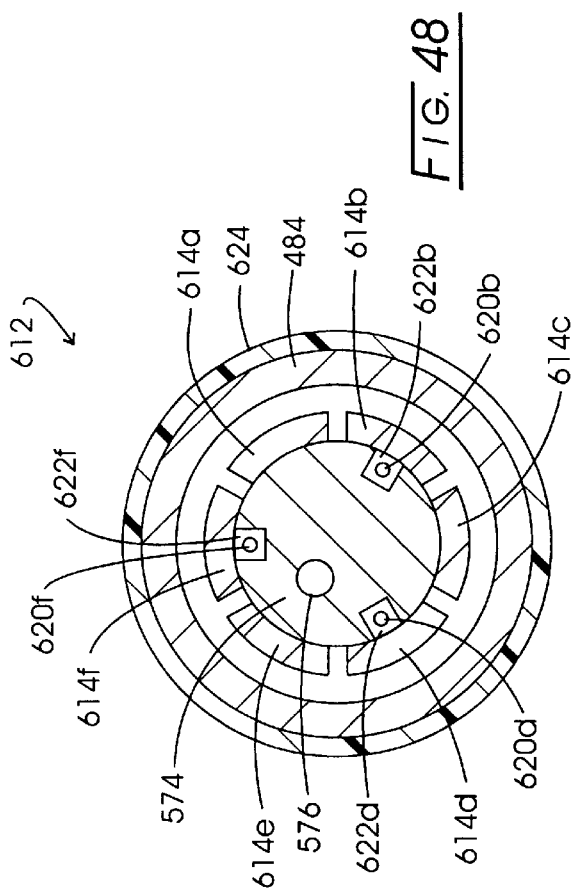
FIG. 48 is a sectional view taken through the plane 48—48 in FIG. 44.

The capture component of the instrument is represented generally at 610 and, as in the previous embodiment, is tubular in shape, being slidably mountable over support component 574 and extending to the earlier described leading edge portion 498. The forward portion 612 of the capture component 610, as before, is configured as having a plurality of discrete, elongate, cage defining leafs which are formed within the tubular structure, for example, by laser cutting or chemical milling. Referring additionally to FIG. 46, the tubular structure of the component 610 along with three of the six cage defining leafs 614a–616c are illustrated. A generally cylindrical configuration of the forward portion 612 is made evident in this figure. Looking additionally to FIG. 47, a developed view of the capture component 610 is represented. This figure shows a total of six deployable leafs 614a–614f which establish the forward portion in tubular fashion as represented in FIG. 46 at 612. Note that the forward tip of each of the leafs 614a–614f is configured having a respective eyelet 616a–616f. Leafs 616b, 616d and 616f additionally are configured having respective tie-off apertures 618b, 618d and 618f. These tie-off apertures function to secure one end of each of three pursing cables 620b, 620d and 620f. Note in this regard, that pursing cable 620b is attached to tie-off aperture 618b, passes through eyelets 616c and 616d and then extends rearwardly beneath leaf 614d to the control and support assembly 508. Looking additionally to FIG. 48, it may be observed that, as pursing cable 620d extends rearwardly, it is slidably positioned within a pursing cable receiving slot 622d formed within the cylindrical external surface of support component 574. Returning to FIG. 47, pursing cable 620d is seen to be attached to tie-off aperture 618d, whereupon it passes through eyelets 616e and 616f and extends rearwardly beneath leaf 614f. FIGS. 44 and 48 reveal that pursing cable 620d is slidably retained within pursing cable receiving slot 622d extending to the assembly 508. Looking additionally to FIG. 47, pursing cable 620f is seen to be attached to tie-off aperture 618f, whereupon, it passes through eyelets 616a and 616b and then extends beneath leaf 614b to support assembly 502. FIG. 48 reveals that this rearward extension of the pursing cable 620f is within pursing cable receiving slot 622f formed within support member 574 and extending to support assembly 508.

While in the general structuring of the forward portion of the capture component, the leafs are arranged symmetrically, their number and the number of cables also is selected in consonance with the geometric shape of the ultimately isolated captured encapsulated tissue. Where six leafs are employed as described above, one, two, three or six cables may be employed. The latter, six cable selection is one wherein the pursing cable is attached to one leaf, extends to the eyelet of the next and returns to pursing cable receiving slot, whereupon, it is directed rearwardly along the support member. The latter arrangement provides for a desirably hemispheric encapsulation geometry. Where five leafs are employed with the capture component then one to five cables may be employed. However, notwithstanding the number of cables, it has been found empirically that a maximum of six cables should be employed for any configuration, the use of more than six cables appearing to evoke a capturing enclosure which may be too rapid. When one cable is utilized, the capturing geometry tends to emulate a nosecone which, for some applications may reach too deep into tissue to achieve an encapsulated removal. Where four, eight or sixteen leafs are employed, then four cables generally are elected. The experimental derived preference for the instrument, however, provides six cables for six leafs and five cables for a five leaf capture component forward portion configuration.

FIGS. 44 and 48 additionally reveal that the delivery cannula 484 metal tubular structure is covered with an electrically insulative shrinkwrap 624 which extends to the return electrode region 502 (FIG. 44) for that embodiment wherein such region is used as the return, as opposed to a remote return or the utilization of the trocar tip 496 for that purpose. In general, the internal guide member 584 and outer guide member 598 of guide assembly 500 are mechanically biased together. For the instant embodiment, it will be seen that outer guide member 598 is biased forwardly by virtue of its connection with the metal tubular component of delivery cannula 484, support component 574 and associated internal guide member 584 being retained in relatively stationary fashion.

Figure 49:
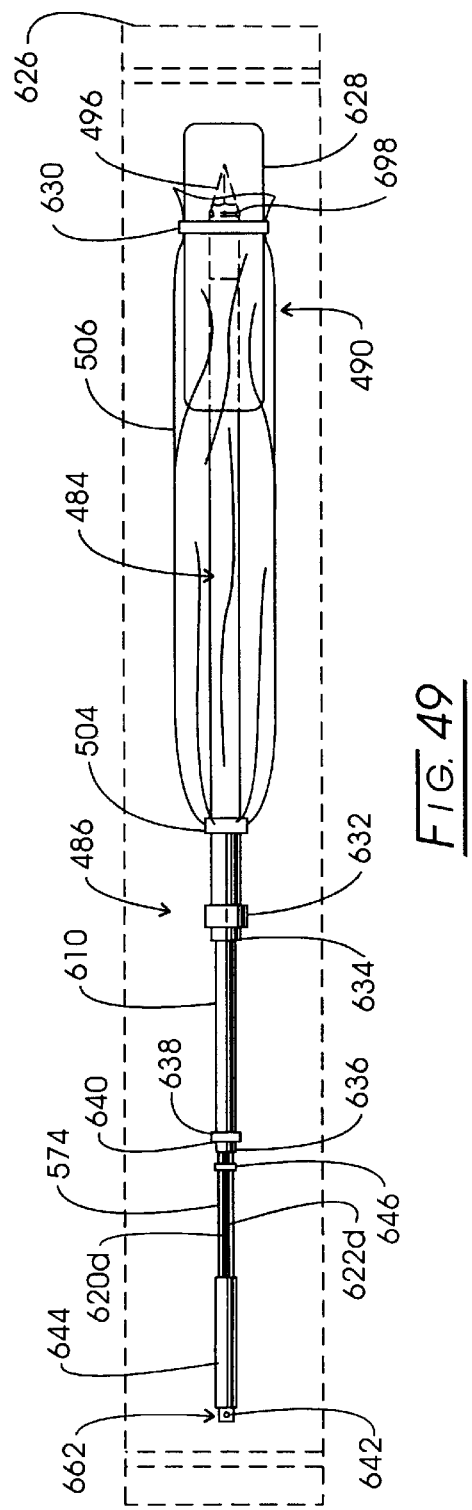
FIG. 49 is a top view of the disposable components of the instrument of FIG. 43 along with a view in phantom of their packaging components.

Referring to FIG. 49, the disposable sub-assembly components of the instrument 482 are revealed as they may be positioned within a sterile packaging arrangement represented in phantom at 626. In the figure, the forward region 490 of the delivery cannula 484 is enclosed within a polymeric sterile capsule 628 which is removable by the practitioner. The sterile shroud 506 is seen to be packaged such that it covers the delivery cannula structure 484 and is attached by a sterile retainer ring 630 against the outer surface of capsule 628. Ring 630 initially is removable to release the shroud 506 at an appropriate point of time following positioning of the disposable components within the control and support assembly 508 (FIG. 42). The proximal end 486 the of delivery cannula 484 and is seen to be coupled with a cylindrical bushing 632 which serves a support function. Bushing 632 is positioned in adjacency with a cylindrical, electrically conductive brushing 634. Bushing 634 is coupled with the delivery cannula 484 and is in electrical communication therewith. Capture component 610 which is coated with an electrically insulative material such as the earlier noted Parylene, is seen to extend from the proximal end portion 486 of cannula 484 to a proximal end 636. Just forwardly of proximal end 636, a cylindrical drive follower 638 having a follower surface 640 is fixed to capture component 610. Extending outwardly from the proximal end 636 of capture component 610 is the cylindrical support component 574 which further extends to a keeper post 642 which forms a component of bayonet-type locking assembly. Slidably positioned over the support component 574 is an electrically conductive tubular or cylindrical comutator sleeve 644. Spaced forwardly from sleeve 644 is a stop ring 646 which is fixed to the support component 574 but provides for the pursing cable receiving slots 622b, 622d, and 622f to extend therethrough along with the pursing cables associated therewith. In this regard, slot 622d is represented in the figure which will contain pursing cable 620d. The position of stop ring 646 establishes the relative retraction leaflet or distance for the pursing cables.

Referring to FIG. 50, the union of the disposable components of the instrument 482, as described in connection with FIG. 49, with the control and support assembly 508 is revealed. In the figure, those components extending rearwardly of the proximal end portion 486 of the delivery cannula 484 are seen inserted within a polymeric housing 650 having an internal cavity represented generally at 652. The mounting of the delivery cannula 484 and associated sterile components is carried out with a bayonet coupling approach. The figure illustrates that the bushing 632 has been inserted within a cylindrical alignment cavity 654. With this insertion, the cylindrical brush bushing 634 is inserted within and slidably engaged with the internal surfaces of a helical biasing spring 656, a forward surface of which engages the annular rearwardly disposed surface 658 of bushing 632. The opposite side of spring 656 is in abutment against electrically conductive contact ring 660 which is fixed to the housing 650. Where an electrosurgical return such as described at 502 (FIG. 44) is employed, the contact ring 660, spring 656 and the proximal region 486 electrically engage, thereby forming a portion of the return circuit. Spring 656 provides a mechanical forward bias asserted upon the delivery cannula 484 which is employed to evoke the bayonet joint type attachment, as well as to develop the above-identified rearward mechanical bias asserted at outer guide member 598 as described in connection with FIG. 44. This bias additionally, is asserted against the internal guide member 584 and, thus, against the elongate support member 574. That member 574 is seen in FIG. 50 to extend to a proximal end 662 through which keeper post 642 is seen to extend. In the mounted orientation shown, that keeper post 642 is seen to have been inserted through a slot entrance to a bayonet engagement chamber 664. Positioned just forwardly of this chamber 664 is a slotted electrically conductive contact ring 666 against which the keeper post 642 now is mechanically biased to complete the bayonet joint form of retention. Accordingly, attachment of the delivery cannula and rearwardly extending components is made by inserting those components within the chamber 652 to an orientation where the spring 656 is compressed and the post 642 is engaged against the rearward surface of ring 666 and is located within the engagement chamber 664. Accordingly, a locking assembly is provided wherein the delivery cannula 484 and components supported thereby may be removed for disposal by pushing it inwardly against the housing 640, twisting it and removing it.

Prior to utilization of the instrument 482, drive follower 638, which is attached to the rearward end of capture component 610, will be positioned rearwardly within the housing cavity 652 such that its rear face 640 is in adjacency with the forward face of a U-shaped saddle cam 668. Cam 668, in turn, is drivably threadably engaged with an elongate screw 670 having a forward end 672 rotatably engaged within a forward cavity formed within housing 640. The screw 670 represents an extension of the shaft of an electric motor 674 mounted within cavity 652. Energization of motor 674 in an appropriate rotational direction, will cause the rotation of screw 670 and the driving of saddle cam 668 forwardly to engage the rearward face 640 of drive follower 638 and push or urge the capture component 610 forwardly. At the instant just prior to the energization of motor 674, electrosurgical cutting energy is applied to pursing cables 620*b*, 620*d* and 620*f*.

As described in conjunction with FIGS. 47 and 48, these electrically conductive pursing cables 620*b*, 620*d* and 620*f* extend from connection with the capture component leading edge 498 along respective receiving slots 622*b*, 622*d* and 622*f*. Cable 620*d* and slot 622*d* are seen in FIG. 50, as extending rearwardly through the cam 668 and stop ring 646 to a tubular comutator sleeve 676. Attachment of each of the three pursing cables to the comutator sleeve 676 is by welding so as to provide a mechanical attachment of sufficient strength for pursing contraction and to provide an electrical conducting connection. A weld spot or nugget corresponding with the attachment of cable 620*d* as shown at 678. The initial assembly of comutator sleeve 676 over the support component 574 may include provision of a breakable retainer seal assuring its rearward positioning during initial insertion of the disposable components. Upon energization of motor 674 at the commencement of capture component deployment, that seal will be broken and the pursing cables 620*b*, 620*d* and 620*f* will be drawn in tension as the saddle cam 668 is driven forwardly by screw 670 to, in turn, urge the drive follower 638 and capture component 610 forwardly. Comutator sleeve 676, accordingly, moves forwardly in correspondence with such movement. As this forward movement ensues, electrosurgical cutting current and voltage is applied to the outer surface of sleeve 676 and, thus, to the pursing cables from cable 528, lead 680 and the resilient brush 682. Brush 682 is seen to be in slidable electrically conducting contact with the sleeve 676. Where the trocar tip 496 is utilized as the electrosurgical return, then a return lead 684 is connected to contact ring 666 so as to constitute the support component 574 as a return conduit which leads ultimately to the noted trocar tip 496. Where the return is at region 502 (FIGS. 43, 44), then an alternate arrangement is provided wherein the lead 684 extends, as represented in phantom at 684' to electrical contact with the contact ring 660 and, thus, with the spring 656.

To achieve a capturing manipulation of the capture component leading edge 498, the pursing cables 620*b*, 620*d* and 620*f* (FIG. 48) are permitted to move forwardly with the capture component 610 in a longitudinal direction along the axis 488 to a predetermined extent, whereupon the cable forward movement is terminated to cause a contractile pursing effect wherein the leading edge 498 is drawn inwardly by the cables toward the axis 488 to complete an isolation and capture of the encapsulated tissue volume. The mechanical orientation of the components within housing 640 at the termination of this maneuver are revealed in FIG. 51. Looking to that figure, note that saddle cam 668 has been moved to position 668' and, in consequence, has driven the capture component forwardly as represented by the location 636' of the proximal end of the capture component, as well as the location 638' of drive follower 638 and its confronting surface as revealed at 640'. During the forward movement of the capture component 610, pursing cables 620*b*, 620*d* and 620*f* have drawn the comutator sleeve forwardly to a location 644' in abutting engagement with stop ring 646. Further movement of the saddle cam 668 causes a tensioning of the pursing cables and contraction of the leading edge 498 of capture component 610. the position of stop ring 646 establishes the length of pursing draw. Thus, its position will vary with capture component size. An alternate location, for example, is shown in phantom at 646' in FIG. 50.

Among the advantages associated with the utilization more than one pursing cable, for example, three as described in connection with FIGS. 42–51, is a capability for rapidly carrying out a pursing maneuver, drawing the leading edges of the capture component leafs into mutual adjacency. This feature obtains inasmuch as the length of pursing cable required for the maneuver is reduced generally in proportion to the number of such cables utilized. Further, when the number of cables is increased, the cumulative cross-section of the cable function increases to an extent permitting their use as a conveyance of electrosurgical cutting and coagulation current. Additionally, a simple stopping action of cable movement is all that is required to carry out the pursing function, for example, as typified by the stop member 646 and corresponding sleeve 644 motion described in connection with FIGS. 50 and 51.

Figure 52:
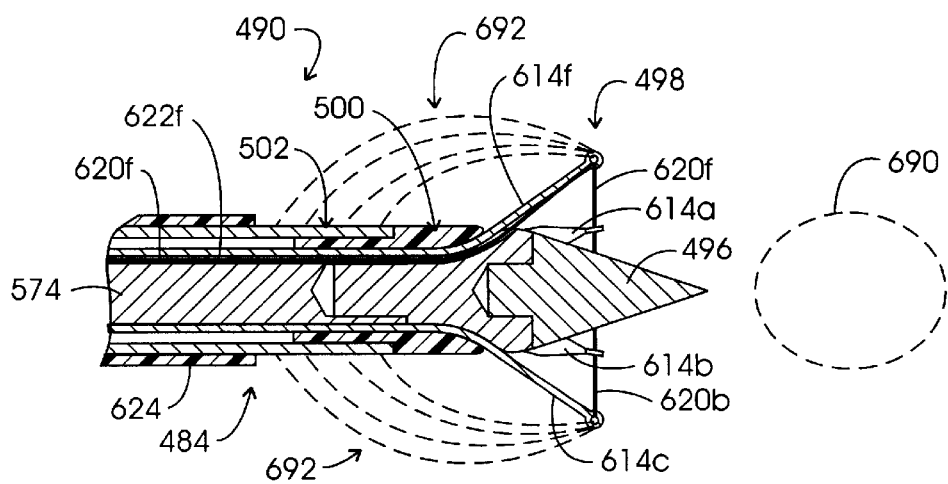
FIG. 52 is a partial sectional view of the forward region of the instrument of FIG. 43 arranged in a confronting orientation with respect to a symbolic targeted tissue, the figure further showing current path lines to a delivery cannula borne electrosurgical return.

During the capture maneuver of the instrument 482, the positioning of the pursing cables with respect to the encapsulated tissue volume differs with respect to the embodiment described in connection with FIGS. 33, 34, 36 and 39–41. This alteration is revealed in connection with FIGS. 52–57 to follow. Looking to FIG. 52, the commencement of deployment of the capture component leafs through the guidance slot employing the pursing cable and leaf embodiment of FIGS. 44–48 is depicted. In the figure, the angle of attack, $\theta_3$, may be observed in conjunction with leafs 614*f* and 614*c* which are commencing to extend into the outer, marginal portion of an encapsulating tissue volume 690. Trocar tip 496 will have been positioned within such tissue in confronting relationship with the targeted tissue represented symbolically at 690. As the three cables 620*b*, 620*d* and 620*f* are excited with electrosurgical cutting or blend current and voltages, a current return path will be developed, as represented by current flux line array 692. The electrosurgical return employed is that earlier described at 502 at forward region 490. Note that the current paths as depicted at current path flux line array 692 extend outwardly from the capture component leafs. Additionally, it may be observed that the pursing cables, one of which is revealed at 620*f*, are located inwardly of these capture component leafs as they extend to and return from engagement at leading edge 498. In general, during this deployment, the cables are retained in a taught or tensioned condition due to the inherent friction exhibited by the pursing cables within receiving slots 622*b*, 622*d* and 622*f*. Additionally, the cables are tensioned by the inherent sliding friction exhibited by the comutator sleeve 676.

Figure 53:
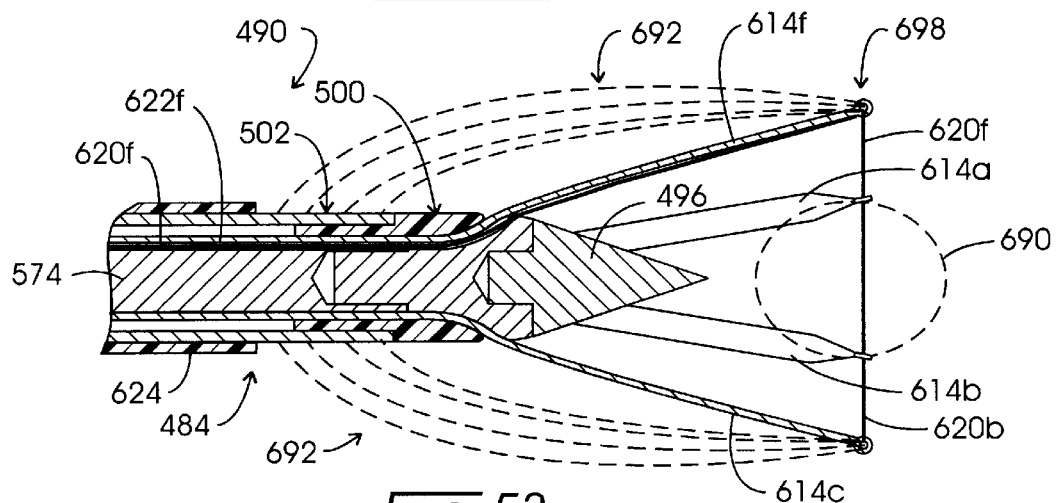
FIG. 53 is a partial sectional view of the instrument of FIG. 52 showing a next later stage in the capture of encapsulating tissue and showing current path lines to a delivery cannula borne electrosurgical return.

As the motor 674 continues to drive the capture component forward, as represented in FIG. 53, the three cutting cables at leading edge 498 commence to approach one side of the targeted tissue 690 within encapsulated tissue surrounding that targeted tissue to an extent providing a margin of severed healthy tissue which ultimately is captured and removed. The orientation of leading edge 498 in FIG. 53 is developed by virtue of sliding cable movement and represents the orientation of the cable as the forward edge of comutator sleeve 644 engages stop ring 646 (FIG. 50).

Figure 54:
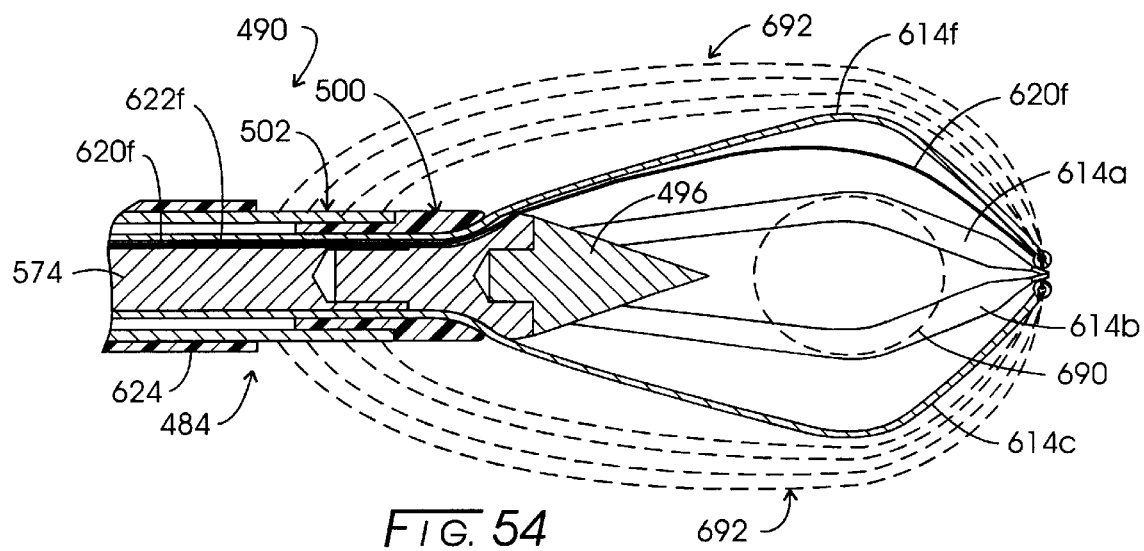
FIG. 54 is a partial sectional view of the instrument of FIG. 53 showing the capture and isolation of an encapsulating tissue volume.

Motor 674 continues to be energized, in turn, to continue to drive saddle cam 668 forwardly and, thus, continues to drive the capture component 610 forwardly. However, during this movement, the halted pursing cables are tensioned and the leafs 614a–614f of the capture component 610 converge at the leading edge 498 to envelop, isolate and, thus capture the encapsulated tissue volume, which incorporates targeted tissue 690 as represented at FIG. 54. Note in FIGS. 53 and 54, that the pursing cables, one of which is seen at 620f remain interiorly of the capture component and encapsulating volume and that the current return path flux lines as at 692 remain outwardly from the capture component and the encapsulated tissue volume.

Figure 55:
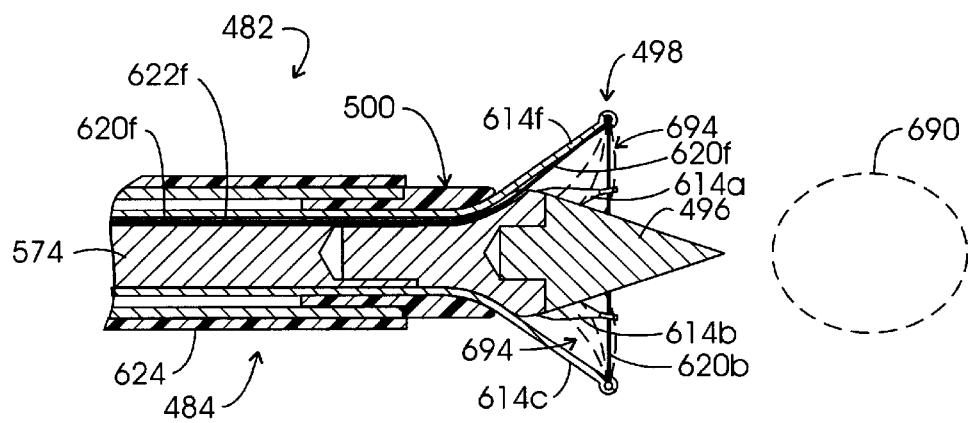
FIG. 55 is a partial sectional view of the forward region of an instrument according to the invention showing an implementation wherein a forward trocar is employed as an electrosurgical return and is showing resultant current paths from a cutting electrode to the return.
Figure 56:
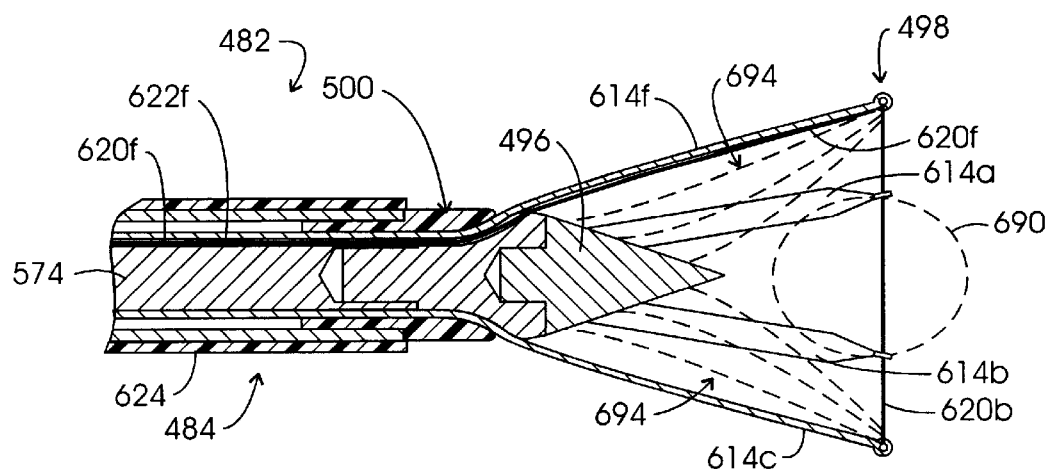
FIG. 56 is a partial sectional view of the instrument of FIG. 55 showing a next stage in the procedure of electrosurgically cutting and isolating and encapsulating tissue volume and showing developed current paths.
Figure 57:
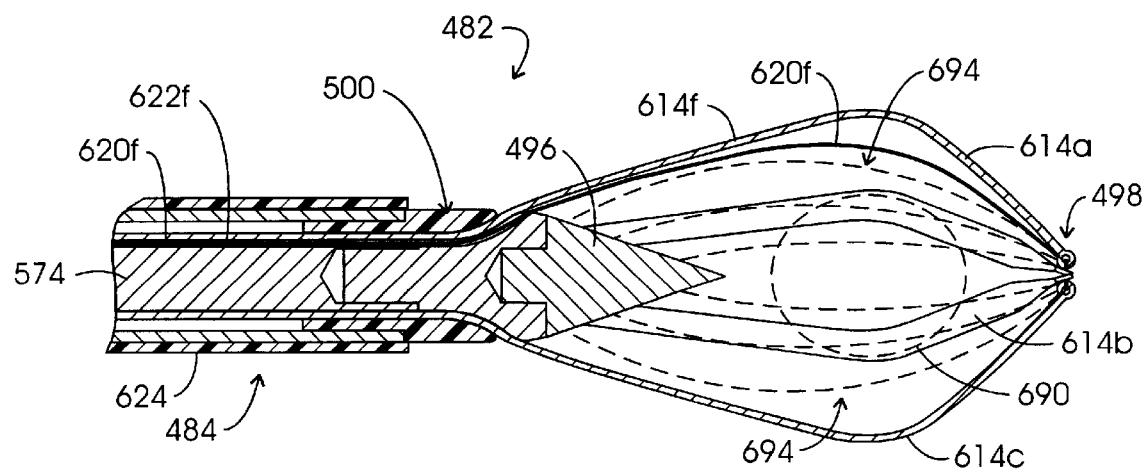
FIG. 57 is a partial sectional view of the instrument of FIG. 55 showing a completion of the isolation of an encapsulating tissue volume and further showing current flow paths at final contraction of a capture component.

The corresponding operation of the instrument 482 in a configuration wherein the trocar tip 496 constitutes a return electrode is represented in conjunction with FIGS. 55–57. FIGS. 55–57 illustrate the same capture and isolation procedure as discussed above in connection with FIGS. 52–54. However, the desirably shortened current return paths between the cables 620a–620f and the return trocar tip 496 now are illustrated as the dashed current flux line arrays 694.

A positioning of the instrument 482, such that the trocar tip 496 is in confronting adjacency with a tissue volume to be encapsulated generally involves preliminary and preferably real time imaging procedures. Conventional preliminary imaging, for example, will utilize x-ray guidance mammography or fluoroscopy. More recently, real time imaging has been approached utilizing magnetic resonance imaging (MRI) or ultrasound procedures. Among the techniques for localization of a lesion is the utilization, for example, of echogenic markers such as microspheres. For example, titanium clips or staples may be attached which remain in place at the lesion following a biopsy. Needle positioned devices such as coils, or radio-opaque marker may be implanted at the site of a lesion and used in conjunction with imaging systems to achieve instrument positioning. Such location marking appliances may be combined with stereotactic guidance systems as well as the noted imaging systems.

Practitioners also have utilized an MRI-compatible needle or localization wire, sometimes referred to as a "J-wire" because of the presence of a barb or hook-shaped distal tip configured to engage the lesion with a thin shaft extending outwardly from the skin or epidermis of the patient. That localization needle, then subsequently is utilized by surgeons for guidance to the lesion during surgery. Positioning of this localization wire typically is through the utilization of an MRI-compatible or acoustic wave compatible needle. See for example, publications (11) and (12) supra.

Instrument 482 may utilize such localization wires for guidance procedures in locating the trocar tip 496 at the noted confronting adjacency with a suspicious lesion. In this regard, the auxiliary channel 576 (FIG. 44) may be employed in conjunction with this guidance procedure.

Figure 58A:
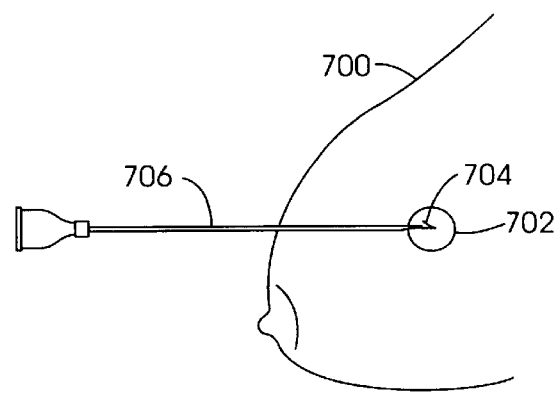
FIG. 58A is a drawing of a human breast and symbolic targeted tissue along with a representation of the implantation of a lesion localization wire.
Figure 58B:
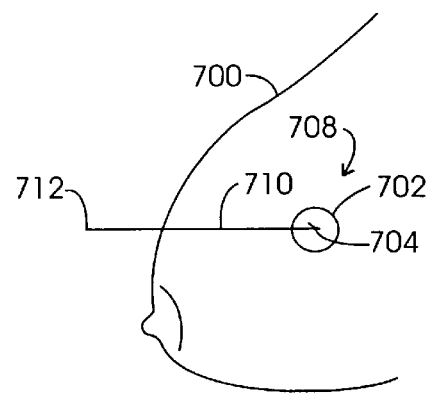
FIG. 58B is a partial view of a breast in symbolic target tissue showing the shank of a lesion localization wire extending from a breast.

Looking to FIG. 58A, a breast is schematically depicted at 700 in conjunction with an internally disposed suspicious lesion 702. A localization wire, the barbed proximal tip of which is represented at 704 is seen being positioned to engage the lesion 702. This engagement is carried out through utilization of imaging procedures in conjunction, typically, with an MRI-compatible or acoustic wave compatible needle 706. For example, an 18-guage Lufkin needle (E-Z-M, of Glen Falls, N.Y.) in combination with a Homer localization J-wire (NAMIC, Glen Falls, N.Y.), may be employed. The placement needle 706 then is withdrawn and the localization wire 708 with shaft 710, as seen in FIG. 58B extends outwardly from the breast 700 to its proximal tip 712.

Figure 58C:
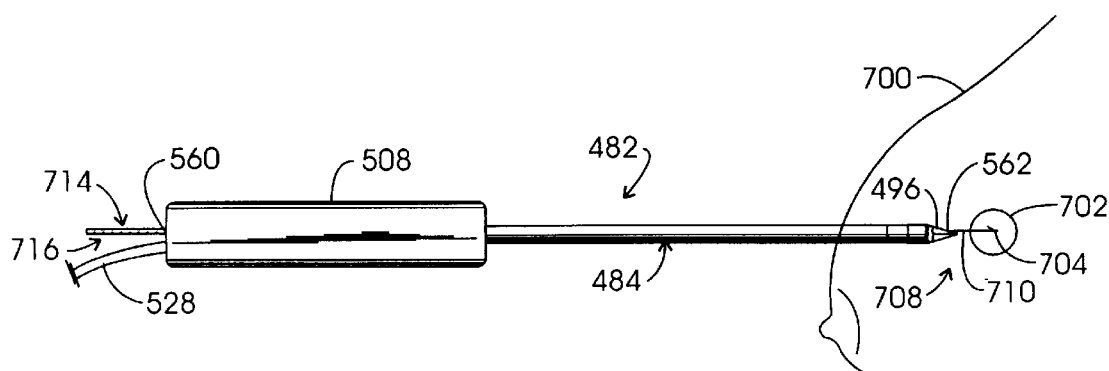
FIG. 58C is a schematic view of an instrument according to the invention during a placement procedure with respect to a human breast utilizing an auxiliary channel which receives the shaft of a lesion localization wire as described in FIG. 58B.

FIG. 58C illustrates the guidance procedure utilizing the localization wire shank 708 in conjunction with the instrument 482 auxiliary channel 576. To apprise the practitioner of the depth position of the trocar tip 562, a follower component 714 is freely slidably positioned within the auxiliary channel 572 as seen in FIG. 58C. In this regard, the component 714 is inserted through the access port 560 such that it extends in abutting adjacency with the proximal tip 712 of localization wire 708. The end region 716 of component 714 functions as a metering proximal end. That end extends outwardly from the access port 560 to an extent corresponding with the instantaneous position of the localization wire 708 proximal tip within the auxiliary channel 572. Indicia may be provided at the region 716 to provide a metering readout. FIG. 58C reveals that the exit opening 562 of the auxiliary channel 572 has slidably received the proximal tip 712 of the shank 710 of localization wire 708. Accordingly, the shank 710 functions as a guide toward the tip 704 and suspicious lesion 702 as the delivery cannula and trocar associated tip 496 is inserted through the breast 700 toward a position of confronting adjacency with respect to the lesion 702. That orientation of confronting adjacency is represented in the figure. Following such positioning, the above-described capturing, isolation removal procedure is carried out.

A further aspect of the procedure for positioning the instrument 482 at a location, for example, represented in FIG. 58C involves the parting of tissue required to gain access to the lesion confrontational instrument tip orientation. Utilization, for example, of the trocar tip 496 alone, generally will involve the dynamic alteration of tissue position wherein tissue in the course of such invasion may be displaced. Such displacement may include a displacement of the lesion itself such that a vectoring procedure may be called for in conjunction with real time imagining to achieve proper instrument placement. A typical outer diameter for the delivery cannula 484 will, for example, be about 5 millimeters. With the instrument 482, this diameter will permit the capture of encapsulated tissue having an effective diameter typically ranging from 20 millimeters to 30 millimeters and, further, may range up to about 40 millimeters. In general, where the lesion effective diameter exceeds the latter value, open surgical procedures commence to be contemplated by the surgical practitioner. Where larger lesions which are captured with instrument 482, additional consideration is called for with respect to the removal of the captured lesion through the initial pathway of access extending from the skin or epidermis and through tissue toward the lesion. For larger lesions, some surgical relief is called for in the nature of a linear incision. Ideally the implement called for might be termed a "perfect lancet" wherein tissue cutting is carried out without significant displacement thereof to evoke a generally physically unhindered accessing movement of the trocar tip 496.

FIGS. 59 through 65 illustrate an adaptation of the instrument 482 wherein a precursor electrosurgical lancet electrode assembly is incorporated with it. Inasmuch as, with the exception of the lancet electrode structuring, the remaining components of instrument 482 remain identical as previously described, identifying numeration is repeated in these figures where appropriate. In FIG. 59, delivery cannula 484 again is seen extending from control and support assembly 508 to a trocar tip 496. However, shown deployed from the exit port 720 of a precursor functioning auxiliary channel within instrument 482 is an electrosurgical lancet electrode assembly shown generally at 722. Assembly 722 is represented in its deployed orientation and is seen to be formed of two resilient wire electrodes 724 and 726. The distal ends of each of the electrode wires 724 and 726 are fixed to the forward region 490 of delivery cannula 484, and, for the instant embodiment, are attached to the rearward region of trocar tip 496 as seen respectively at 728 and 730. These ends 728 and 730 are electrically insulated from the instrument, and for this requirement, the trocar tip 496 may, for example, be formed of an electrically insulative material such as a polymer. As thus deployed, the electrode wires 724 and 726 are extended in coplanar fashion, being shown in the figure as being located within a common precursor or lancet plane 732. The electrode wires 724 and 726 are deployed in compression to define an arch structure of predetermined height and which establishes leading edges as shown respectively at 734 and 736 which extend forwardly of the trocar tip 496. Electrodes 724 and 726 are excited with electrosurgical cutting current and operate in conjunction with a remote return electrode such as that shown at 530 in FIG. 42. When used, the practitioner makes a shallow linear cut in the epidermis at the location of desired insertion of the delivery cannula 484. Then, the electrode leading edges 734 and 736 are inserted through this preliminary cut and carry out electrosurgical cutting to form an access path to an orientation confronting the targeted tissue as earlier described. Electrodes 724 and 726 then are retracted and the capture component activity as described above ensues.

Referring to FIG. 60, the lancet electrodes 724 and 726 are seen connected to an electrically insulative trocar tip 496 and extend from the exit port 720 of an elongate precursor or auxiliary channel 739. In general, the wire establishing electrode 724 and 726 may be about a 10 mil diameter stainless steel material. These wires are deployed in compression forwardly utilizing a lancet electrode actuating assembly which is seen in FIG. 59 in general at 740. By so compressibly urging the electrode wire 724 and 726 forwardly, advantage is taken of the inherent structural integrity of the arch, the connections at 728 and 730 providing a buttress defining form of connection.

Figure 61:
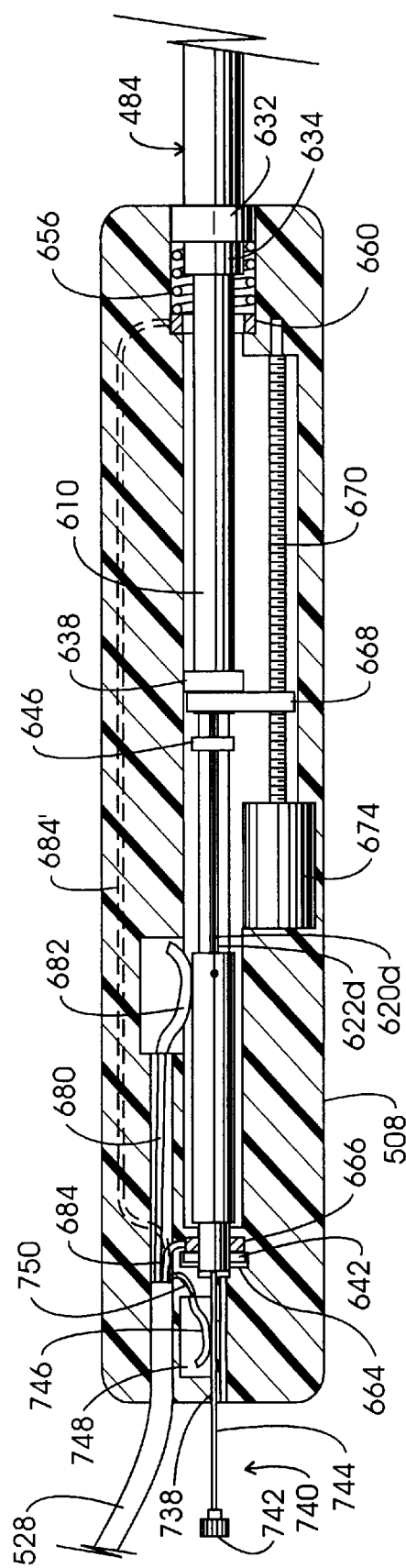
FIG. 61 is a partial sectional view of the control and support assembly of the instrument of FIG. 59 taken through the plane 61—61 shown therein.

FIG. 61 reveals that the lancet electrode actuating or deploying assembly 740 extends through the housing 508 and terminates in a cap 742 which is attached to a metal push rod 744 which, in turn, is electrically and mechanically connected to the proximal ends of electrode wires 724 and 726. Electrosurgical cutting current is delivered to the push rod 744 and from rod 744 to the electrode wire 724 and 726 through a brush 746 positioned within a brush cavity 748. The electrosurgical excitation current extends to the brush 746 from a lead branch 750 extending from cable 528.

Following the utilization of leading edges 734 and 736 to cut and part tissue to position the delivery cannula 484 into a targeting tissue confronting orientation, electrodes 724 and 726 are retracted. Looking to FIG. 62, the retracted orientation of the electrode 724 and 726 is depicted. When thus retracted, these electrodes will not interfere with the capture component leafs 614*a*–614*f* as they are deployed in the earlier-described capturing and isolating activity as represented in FIG. 62.

Figure 63:
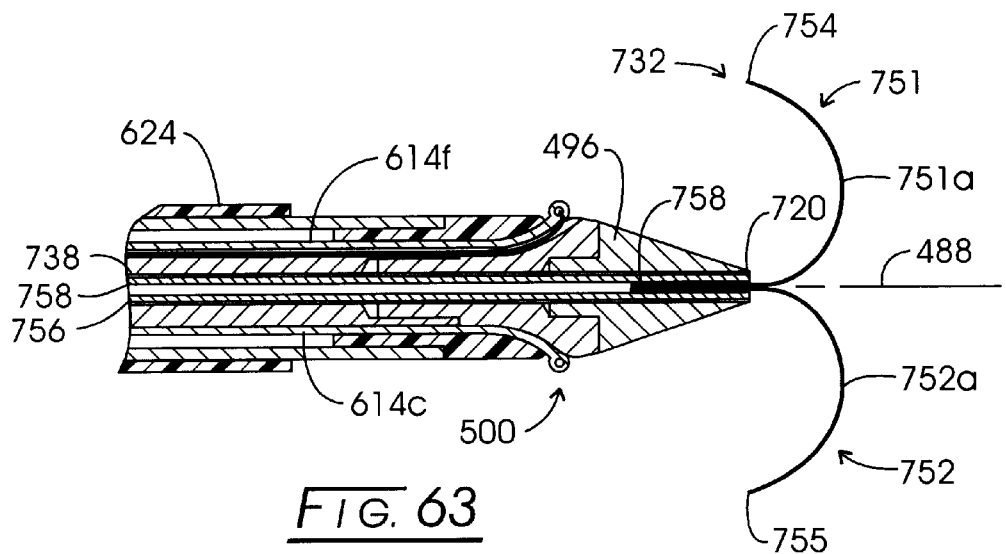
FIG. 63 is a partial sectional view of the instrument of FIG. 9 showing an alternate lancet electrode embodiment represented in a deployed orientation.
Figure 64:
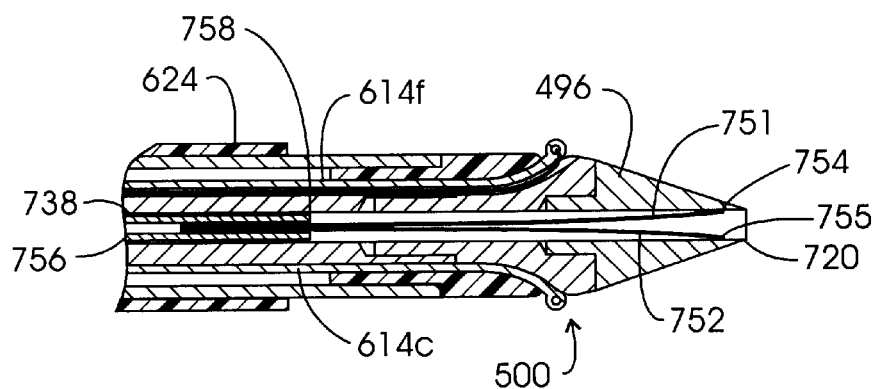
FIG. 64 is a partial sectional view of the instrument of FIG. 63 showing lancet electrodes in a retracted orientation.
Figure 65:
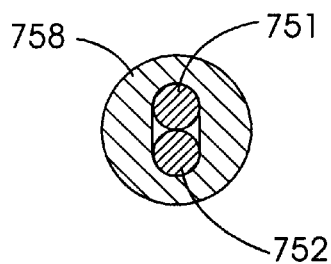
FIG. 65 is a partial sectional view of the deployment mechanism utilized with the instrument embodiment of FIG. 63 and 64.

FIGS. 63–65 reveal another embodiment for the lancet electrode assembly carrying out a precursing electrosurgical cutting function to provide an access path to the position of confronting adjacency with targeted tissue. FIG. 63 reveals two, wire-form lancet electrodes represented generally at 751 and 752. Rather than being embedded within the distal tip portion 496 of the instrument, the electrodes 751 and 752 extend to respective tips 754 and 755 and are pre-stressed or pre-bent resilient wire material such as stainless steel to present confronting electrode surfaces of arcuate configuration within the lancet plane 732 as represented respectively at 751*a* and 752*a*. Note that these arcuate surfaces extend forwardly of the exit port 720 of an auxiliary channel 756. In the deployed orientation shown, the electrode 751 and 752 extend transversely from the longitudinal axis 488 in the noted lancet plane 732 as illustrated in FIG. 59. The exit port 720 and channel 756 are seen to be disposed along longitudinal axis 488 and with the arrangement shown, the channel 756 may be employed for other purposes such as needle based sampling (FNA) and the like as described above. Electrode wires 751 and 752 are fixed to a generally tubular shaped deployment assembly 758 which is slidably mounted within the channel 756. FIG. 65 reveals this component 758 as it retains wire electrodes 751 and 752 in proper orientation for deployment and retraction. FIG. 64 shows the retracted orientation of the electrodes 751 and 752. As noted above, these electrodes along with the deployment mechanism 758 may be entirely removed from the instrument to permit other uses of the auxiliary channel 756. A remote return electrode as described at 54 in FIG. 1 is deployed for operation of these lancet electrodes.

Figure 66:
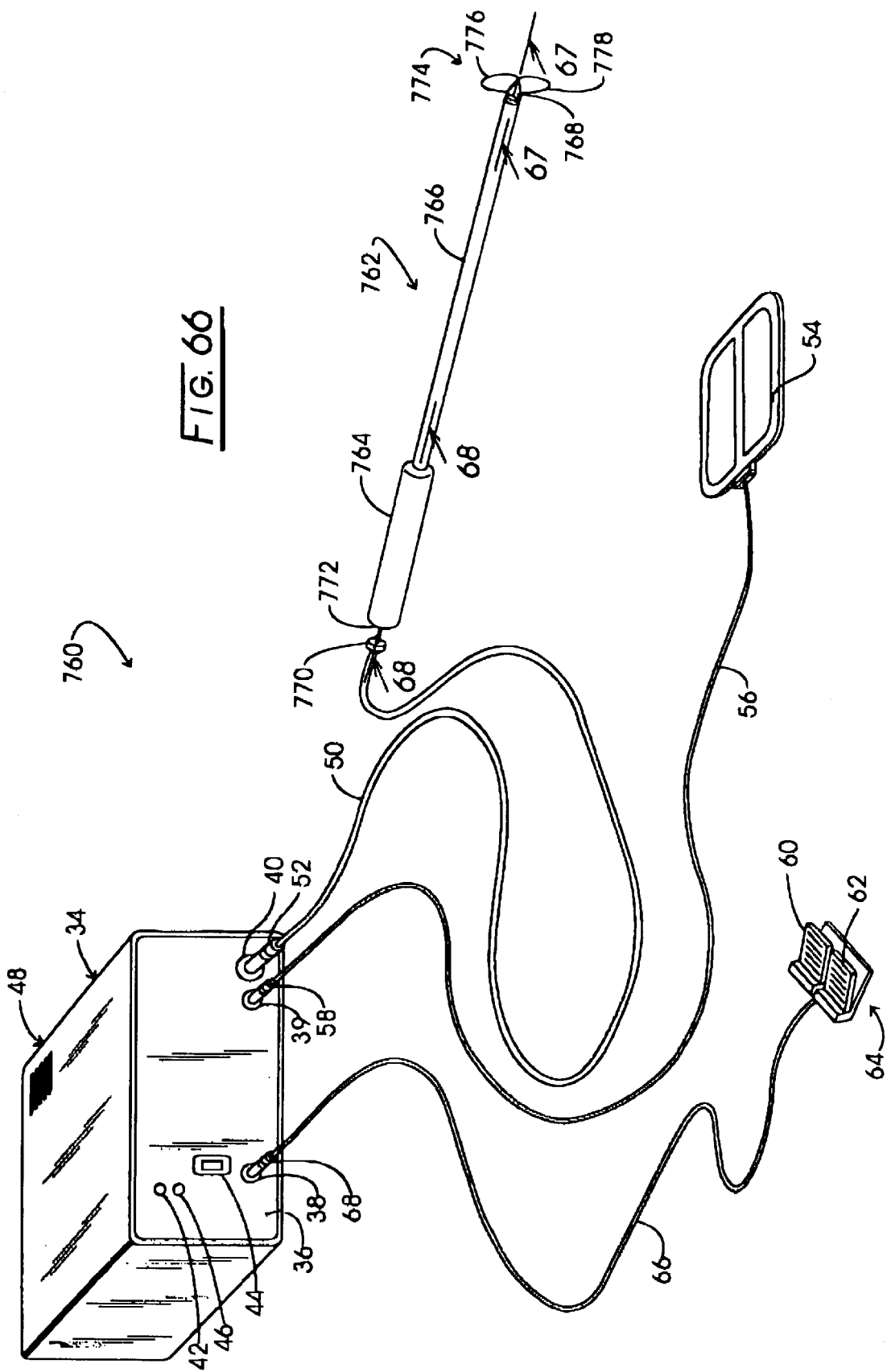
FIG. 66 is a perspective view of a system according to the invention showing an electrosurgical precursor lancet electrode supporting instrument in conjunction with a remote return.

The precursor lancet electrodes also may be employed with a separate dedicated instrument which is utilized in the same manner, i.e., forming a preliminary incision which parts tissue up to an orientation confronting the targeted tissue. Referring to FIG. 66, such a system is depicted generally at 760 with a dedicated instrument represented generally at 762 which is seen performing in association with a conventional electrosurgical generator arrangement such as that described in connection with FIG. 1. Accordingly, the numeration identifying generator and remote return components is repeated in the instant figure. In this regard, a selected footpedal switch 60 or 62 is actuated to supply electrosurgical cutting current via a cable 50 to instrument 762. A remote return 54 with associated cable 56 is coupled to the generator 34 as described earlier. Instrument 762 is seen to be formed with a deployment and support assembly at handle 764 to which is connected a delivery cannula 766 extending to a pointed tip 768. The hand actuable cap 770 of an actuating assembly represented generally at 772 is shown extending rearwardly from the handle 764. As before, a lancet electrosurgical assembly 774 is shown in a deployed orientation, being formed of two electrode wires which are compressibly forwardly driven to define arch-shaped wire electrodes 776 and 778.

Figure 67:
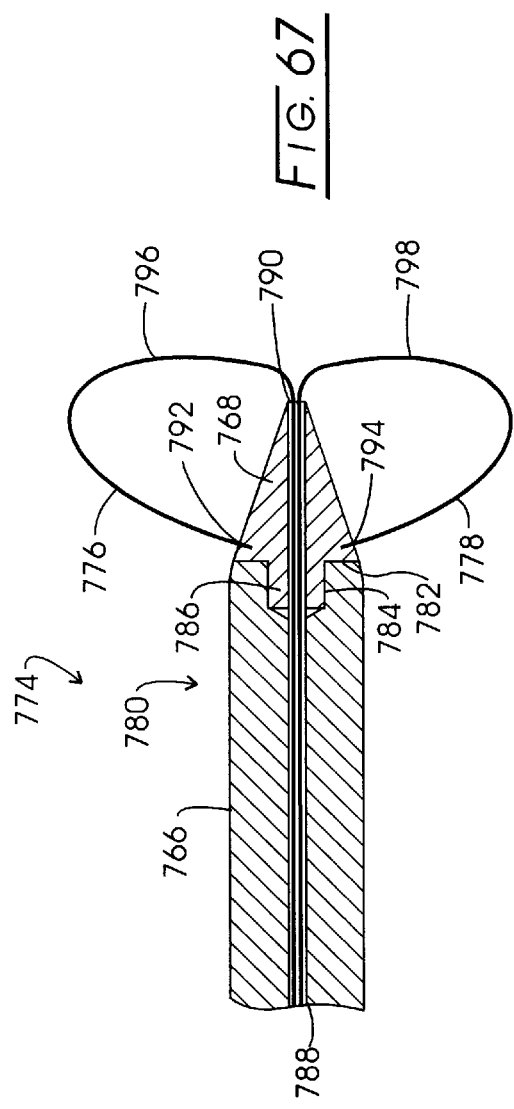
FIG. 67 is a sectional view of the instrument of FIG. 66 taken through the plane 67—67 therein.

Referring to FIG. 67, the distal end of delivery cannula 766 is revealed at 780, the cannula terminating in an annular surface 782 within which a receiving cavity or bore 784 is formed. Installed within the bore 784 is the protruding post 786 of the tip component 768. Extending through both the tip component 768 and the delivery cannula 766 is a precursor channel 788 which functions to carry the electrode wires 776 and 778 shown deployed and extending from the exit port 790 of channel 788. As before, the distal ends or tips of wires 776 and 778 are embedded or fixed within the tip 768 as represented respectively at 792 and 794. As noted above, with the arrangement, the respective leading edges 796 and 798 of electrode wires 776 and 778 extend in coplanar fashion forwardly of the exit port 790 and assume a compressive arch configuration which is quite stable and easily deployed. The extent of such deployment establishes the height of the leading edges 796 and 798. As the size of the targeted lesion increases, the outwardly deployed extent of the leading edges 796 and 798 is established accordingly.

Figure 68:
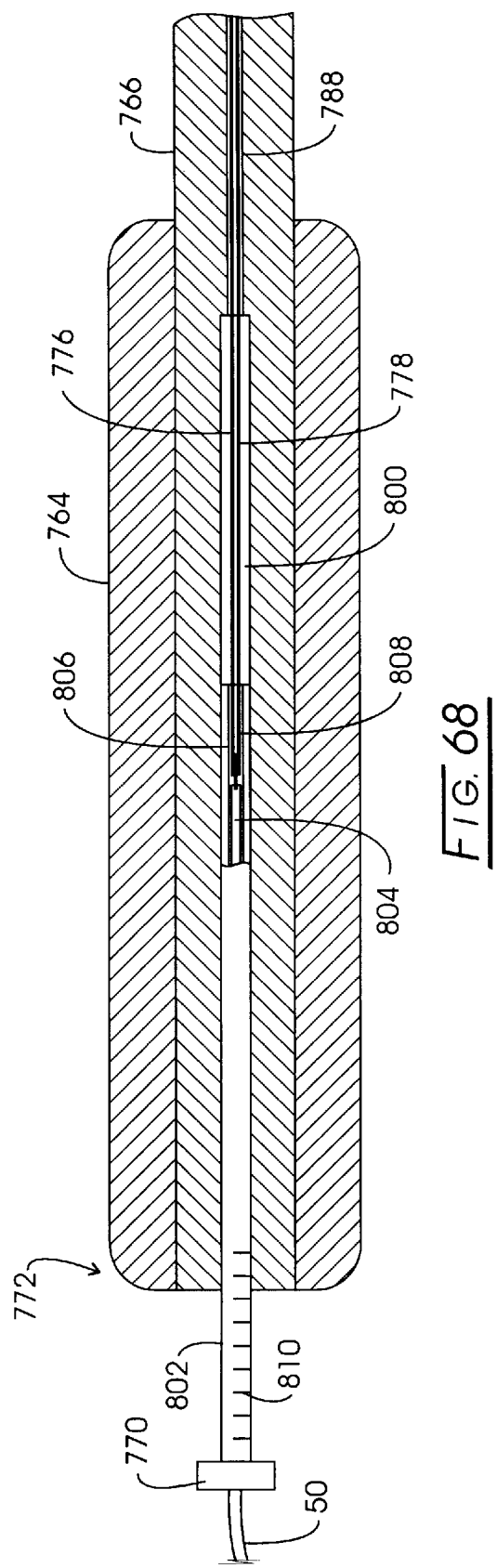
FIG. 68 is a sectional view of the instrument shown in FIG. 66 taken through the plane 68—68 therein.

Looking to FIG. 68, the deployment assembly which may be utilized with instrument 762 as well as with the instrument embodiment of FIGS. 60–65 is illustrated. In the figure, the delivery cannula 766 is shown to extend through handle 764 and the precursor channel 788 carrying electrode wire 776 and 778 extends to a cylindrical deployment chamber into which a push rod 802 attached to cap 770 is slidably inserted. The internal portion of push rod 802 incorporates an electrical lead 804 coupled in electrical communication with cable 50 and with the proximal ends 806 and 808 of respective electrode wires 776 and 778. Ends 806 and 808 are fixedly embedded within the push rod 802. Consequently, when the rod 802 is moved forwardly, the electrode wires 776 and 778 are moved forwardly in compression to deploy the arch shaped cutting configuration shown in FIG. 67 against the abutment defining connection 792 and 794.

Referring to FIG. 69, a block schematic representation of a dedicated electrosurgical generator and associated control assembly earlier generally described in connection with FIG. 42 at 510 is portrayed. The generator 510 functions in conjunction with remote return 530, triple footpedal switches 536–538 and motor drive 546 to support precursor lancet electrode based positioning of the instrument 482 in confronting relationship with the tissue encapsulating a targeted tumor and, subsequently, provides electrosurgical cutting and coagulation current and voltage to the cable-based electrosurgical cutting components of the system. These procedures call upon the practitioner to operate the menu driven display 518 in conjunction with the up-down switches 520. Blocks representing those functions are seen with the same identifying numeration in the instant figure. Initially shown are the connectors 516 and 544 emanating from cable 542 and footpedal switches 536–538. The connectors from a remote electrode 530 are shown again at 515 and 534 and connector 524, as well as 514 are reproduced in conjunction with branch cable 522 leading both to the motor control 546 and instrument 482. The figure further reveals a radiofrequency (RF) cutting current electrosurgical generator at block 820. Performing with either a full electrosurgical cutting waveform or a blend waveform, the generator 820 provides for selected cutting energization of both the pursing cables and the lancing electrodes such as those described at 724 and 726 in FIGS. 59 and 60. The second RF generation function is represented at block 822 and derives the earlier-described white coagulation currents and voltage waveforms. Generating functions 820 and 822 are under the general control of a control circuit represented at block 824. In this regard, actuating control to the cutting generator function 820 is represented at arrow 826, while a similar actuation control over the white coagulation generator function 822 is represented at arrow 828.

Control direction to the control circuit 824 with respect to the cutting currents evoked at generator function 820 is developed from a cutting and cable enable-motor on and motor stop logic function represented at block 830. This function 830 is controlled from a menu switching logic function represented at block 832 which, in turn, is controlled by the operator from the up-down switches now represented at block 520, such input being represented, in turn, at arrow 834. Control from the menu logic function 832 to the cutting logic function at block 830 is represented at arrow 836. In general, the function 830 enables the control circuit to develop electrosurgical cutting current at the pursing cables 620b, 620d and 620f essentially at the commencement of or just prior to the activation or engerization of drive motor 674 (FIGS. 50, 51). This activation is selected from logic represented at blocks 830 and 832 but initiated by the practitioner with the depression of footpedal switch 536. Where a precursor electrosurgical lancet electrode described in connection with FIGS. 59 and 60 at 724 and 726 is employed, then appropriate menu switching logic at block 832 is elected through the utilization of the up-down switches 520 by the operator. This, in turn, carries out a lancet enable activity represented at function block 838 which, in turn, enables the development of such cutting currents as are required from the control circuit 824 as represented by arrow 840. Menu switching logic input to the function at block 838 is represented at arrow 842. This lancet electrode cutting activity is under the control of the practitioner by virtue of the actuation of footpedal switch 537. A response to depression of any of these footpedals 536–538 is evoked at the menu switching logic function 832 as represented at arrow 844 and is directed the control circuit 824 as represented at arrow 846.

Looking now to the conveyance of electrosurgical cutting current and waveform in the instrumentation, the output of the generator function 820 is present at lines 848 and 850 and is directed to a switching function represented at block 852 which is seen to incorporate two solid state switches represented at switch symbols 854 and 856 corresponding with a switching association with respective lines 848 and 850. The output of the switches 854 and 856, when functionally closed, is directed to respective lines 858 and 860 which extend to the primary side of an isolation transformer 862. A secondary side of transformer 862 is present at lines 864 and 866 which are directed to the input of a high pass filter 868. The output of filter 868 is present at lines 870 and 872. Of these lines, line 872 is an electrosurgical return which is seen coupled through connectors 515 and 534, as well as cable 532 to the remote return described at 530 in FIG. 42. Line 870 is seen to be directed to a motor/lancet selection switching function represented at block 874 which is seen to be under the control of the cutting cable enable function at block 830 as represented by arrow 876 and under the control of the lancet enable function at block 838 as represented at arrow 878. Thus, the switching function 874 is actuated with the activation of cutting cable enable function 830 to provide a cutting output at line 880 which is directed to terminal 882b of a terminal block represented at 884. The return at line 872 is directed via line 874 to terminal 882a of terminal block 884 and the resultant electrosurgical cutting output is directed via cables 522 and 528 to the pursing cable of the instrument 482. When the lancet enable function is active as represented at block 838, then the switching function carries out a switching activity directing the electrosurgical cutting current along line 886 which is coupled with terminal 882d of terminal block 884. Depression of footpedal 536 as described in connection with FIG. 42 not only activates the delivery of electrosurgical cutting current to the pursing cables, but also activates or energizes the motor 674 (FIGS. 50–51). The signal deriving this energization of the motor is presented from the motor-on logic function at block 830, as represented at line 888, to terminal 882e. Returning momentarily to FIG. 51, when the saddle cam 668 and the drive follower 638 reach the terminus of their forward movement, motor 674 is stalled and the resultant back EMF is directed through the cables 528 and 522 to terminal 882f for redirection along lead 890 to the motor stop logic function at block 830. The result is a cessation of the conveyance of electrosurgical cutting current by virtue of signals presented to the control circuit 824 from the function block 830 as represented at arrow 892. Additionally, current to the motor is terminated and an aural and visual cue is given to the practitioner to release the footpedal 536 as represented at arrow 894 and display block 518.

Where the practitioner elects to carry out white coagulation, for example, during withdraw of a tissue sample, then the footpedal switch 538 is actuated. This provides an input as represented at line 846 to the control circuit 824 which, in turn, as represented at arrow 828 activates the coagulation current generation function as set forth at block 822. A resulting white coagulating electrosurgical current and voltage waveform is promulgated at lines 896 and 898 which is directed to respective switch components 900 and 902 of the logic switching function 852. The resultant output then is presented at respective lines 904 and 906 which are directed to the primary side of an isolation transformer 908. A secondary side of transformer 908 is coupled to return line 872 and to line 910 which is directed to the input of a high pass filter represented at block 912. The resultant output at line 914 is provided at terminal 882c of terminal block 884 and, ultimately, is combined with the output of terminal 882 for presentation to the pursing cables of the instrument 482.

FIGS. 70A, 70D combine as labeled thereon to provide a flow chart showing the utilization of the tissue isolation and retrieval instrument and supporting components of the invention. In FIG. 70A, the procedure commences as represented at the start node 920 and proceeds as represented at arrow 922 to the instructions at block 924. These instructions provide for the locating or localization of the target tissue utilizing an imaging modality such as radiography, ultrasonography, magnetic resonance imaging (MRI) or the like. Optionally, this locating of the target tissue can be accompanied by the affixation of a marker. Additionally, the practitioner is called upon to assess the size of the target tissue. This calls for then selecting an instrument configuration wherein the electrosurgical cutting leading edge portion of the capture component is expandable toward an outer peripheral dimension which corresponds with the assessed target tissue size. Recall, additionally, that marginal healthy tissue also is desired to be encapsulated about the target tissue to assure complete removal and to minimize any opportunity for seeding metastasis to occur. The procedure then continues as represented at arrow 926 and block 928 wherein the tissue isolation and retrieval instrument is selected based upon the noted assessed tumor size and corresponding desired margin of tissue which is healthy which surrounds tumor. As noted at block 928, about a 2 to 5 millimeter margin of such healthy tissue is retrieved with the target tissue, the entire agglomeration of tissue being referred to as "encapsulated tissue". The procedure then continues as represented at arrow 930 and block 932 wherein the guidance procedure employing imaging and/or guidance implements is utilized to position the working end of the isolation and retrieval instrument at a location in confronting adjacency with the target and surrounding marginal tissue. This positioning may be performed manually or with the aid of motion-controlled positioning apparatus, for example, additionally utilizing stereotaxy positioning implements. As discussed in conjunction with FIGS. 59–68, an electrosurgical precursor lancet electrode may be employed to aid in this instrument positioning procedure. A remote return electrode is employed for this precursor tissue parting approach and, in general, a scalpel or tissue parting device of conventional structure is employed to make an initial cut through the epidermis, whereupon the lancet electrodes are applied to provide a linear surgical incision extending toward the targeted tissue and marginal tissue surrounding it. The instrument working end, including the capture component leading edge, then is located in the noted confronting adjacency with the tissue to be encapsulated and the precursor electrodes are retracted and/or removed. The procedure continues as represented at arrow 934.

Arrow 934 reappears in FIG. 70B leading to an optional step in the procedure represented at dashed block 936. At block 936, an option for carrying out an FNA sampling is provided wherein a sampling needle, as described at 564 in conjunction with FIGS. 43 and 44, is employed to effect aspiration of tissue (cells) from the target tissue prior to its excision. Following such optional procedure, then as represented at arrow 938 and block 940, guidance toward the targeted tissue may be carried out as described in connection with FIGS. 58A–58C wherein the auxiliary channel of the tissue isolation and retrieval instrument is utilized in conjunction with a localization wire to provide instrument guidance into the noted position of confronting adjacency with the targeted and surrounding marginal tissue.

The procedure then continues as represented at arrow 942 and block 944 wherein an appropriate switch such as a footpedal switch is actuated to commence the energization of the cutting wire electrodes associated with the pursing cable structure. Either an electrosurgical cutting waveform or electrosurgical blend waveform may be used for this electrode excitation. As the excitation occurs, the capture component may be manually advanced to envelop the margin isolated target tissue volume. This advancement continues in until the leading edge portion of the capture component approaches the side of the targeted tissue opposite that side which is faced in confronting adjacency. Such an orientation is represented, for example, in FIGS. 52 and 55. While advancement of the leading edge of the capture component then may proceed, it does so in conjunction with the contraction of its leading edge by applying tension to the pursing cable structure. This achieves a capture component closure about the encapsulated tissue, whereupon, as represented at arrow 946 and block 948, the application of electrosurgical current to the cutting wire electrodes extending from the pursing cables is discontinued. This may be carried out, in one embodiment, by releasing a footpedal switch.

The procedure then continues as represented at arrow 950 which reappears in FIG. 70C extending to the dashed optional step represented in dashed block 952. The procedure associated with block 952 is concerned with the motorized drive embodiment of the instrument of the invention, for example, as described in conjunction with FIGS. 50 and 51. As described above, depression of an appropriate footpedal as at 536 in FIG. 42 effects the commencement of electrosurgical cutting and the energization of the motor drive feature to commence the extension or expression of the tissue capture component such that it automatically envelops, isolates and effects a capturing of the encapsulated tissue. The motorized extension of the capture component continues following the blocking of pursing cable movement to cause contraction of its leading edge. At the termination of forward movement occasioned by motor drive, either switching or detection of a back EMF resulting from motor stall may be employed both to terminate the generation of electrosurgical cutting current and to de-energize the motor.

As an alternative structure, an uptake reel may be actuated to withdraw the pursing cable to cause the noted contraction of its leading edge while electrosurgical cutting energy is applied to the cutting cable portion of the pursing assembly.

As represented at arrow 954 and dashed block 956, a further option is available to the practitioner wherein a marker component deployed for the purpose of marking the cavity resulting from removal of the encapsulated tissue volume. This step may be carried out utilizing a separate placement instrument following removal of the encapsulated tissue.

The procedure then provides as represented at arrow 958 and block 960 wherein the capture component with encapsulated tissues is removed from the body of the patient. This removal is facilitated by the initial precursor lancet electrode cut which is selected having a linear dimension corresponding with the size of the removed tissue and the encapsulating capture component. Release of the encapsulated tissue component from the capture component is carried out with the simple expedient of severing the pursing cables and the released tissue volume then is subject to pathological examination.

The procedure continues as represented at arrow 962 which reappears in FIG. 70D extending to the optional procedure represented at dashed block 964. With this step, for example, footpedal switch 538, as described in conjunction with FIG. 42, may be actuated to carryout a white coagulation utilizing the cutting cable during withdraw of the capture component. This results in an assured sealing of any severed blood vessels and a cauterization of interior surfaces of tissue within the withdrawal track. That procedure, as described above, functions to minimize opportunity for what is sometimes referred to as "needle track metastasis" or metastasis which occurs within the surgical assess channel in consequence of the removal of the encapsulated tissue volume. The procedure then may continue as represented at arrow 966 to the optional treatment step represented at dashed block 968. In this regard, if excessive bleeding occurs before or after removal of the capture component, a hemostatic agent such as fibrin glue may be injected into the cavity previously occupied by the target tissue volume and/or the instrument access track to effect homeostasis. Alternately, a surgical balloon may be inserted into that cavity following removal of the capture component, whereupon it is inflated to apply tamponade to effect hemostasis. The procedure then ends as represented at arrow 970 and node 972.

Since certain changes may be made in the above-described apparatus, method and system without departing from the scope of the invention herein involved, it is intended that all matter contained in the description thereof or shown in the accompanying drawings shall be interpreted as illustrative and not in a limiting sense.

What is claimed is:

1. Apparatus for retrieving a tissue volume of predetermined peripheral extent, comprising, a delivery cannula having an outer surface surmounting an interior channel and extending from a proximal end portion along a longitudinal axis to a forward region, having a distal end positionable in confronting adjacency with said tissue volume;

a capture component positioned within said delivery cannula interior channel, having an expansible forward portion extending to a forwardly disposed electrically conducting electrosurgical cutting leading edge portion and being extendible and expandable toward an outer peripheral dimension selected for the circumscriptive engagement of said tissue volume peripheral extent when moved along said longitudinal axis to egress from said delivery cannula; and a deployment assembly extending within said interior channel, drivably coupled with said capture component and actuable to effect said movement of said capture component along said longitudinal axis, and for effecting a subsequent contraction of said leading edge portion to provide closure of said capture component leading edge portion, and including a terminal assembly for simultaneously effecting the conduction of electrical energy to said leading edge portion.

2. The apparatus of claim 1 in which said capture component leading edge portion comprises a flexible metal wire responsive to said conduction of electrical energy to effect electrosurgical cutting of tissue upon said movement and contraction.

3. The apparatus of claim 1 in which:

said capture component forward portion is generally tubular, including a plurality of discrete elongate cage defining leafs having sides extending in parallel with said longitudinal axis to tip portions; and said deployment assembly includes a guidance assembly fixed to said delivery cannula adjacent said distal end and configured to effect deployment of said leafs into tissue at a predetermined angle of attack when said deployment assembly is actuated.

4. The apparatus of claim 1 in which said guidance assembly is configured having a plurality of guidance slots, each configured for slidably receiving one of said discrete cage defining leafs and angularly oriented with respect to said longitudinal axis.

5. The apparatus of claim 3 in which:

said capture component leading edge portion comprises a flexible metal wire slideably connected to said tip portions of said leafs, expandable therewith when deployed into tissue, responsive to said conduction of electrical energy to effect electrosurgical cutting of tissue when said leafs are deployed into tissue.

6. The apparatus of claim 5 in which:

said tip portions of said leafs incorporate apertures; and said flexible metal wire extends in slideable relationship through said apertures and is formed as a component of a pursing cable assembly configured to draw said tip portions inwardly toward said longitudinal axis to effect said subsequent contraction of said leading edge.

7. The apparatus of claim 6 in which:

said capture component leafs are coupled in electrical communication with said terminal assembly and are configured to convey electrical energy to said flexible metal wire from said apertures.

8. The apparatus of claim 3 in which:

said deployment assembly guidance assembly extends forwardly from said delivery cannula distal end, is configured having a tissue parting pointed component, said pointed component being formed of electrically conductive material and is electrically coupled with said terminal assembly to function as a return electrode.

9. The apparatus of claim 3 in which:

said delivery cannula is formed of electrically conductive material and includes an electrically insulative layer located over said outer surface, said layer having a return electrode defining opening at said forward region, and said delivery cannula being electrically coupled with said terminal assembly to provide an electrical return electrode at said opening.

10. The apparatus of claim 1 including:

a support assembly coupled in supporting relationship with said delivery cannula at said proximal end portion;

an elongate auxiliary channel extending in generally parallel relationship with said longitudinal axis from an access port within said support assembly, through said interior channel to an exit opening at said delivery cannula distal end; and an elongate sampling needle extendable through said auxiliary channel a length effective to engage said tissue volume in tissue sample removing relationship when said delivery cannula distal end is in confronting adjacency with said tissue volume.

11. The apparatus of claim 1 including:

a support assembly coupled in supporting relationship with said delivery cannula at said proximal end portion; and an elongate auxiliary channel extending in parallel relationship with said longitudinal axis from an access port within said support assembly, through said interior channel to an exit opening adjacent said axis at said delivery cannula distal end, said auxiliary channel being configured to slidably receive the proximal tip and shank of a lesion localization wire; and a follower component slidably extending within said auxiliary channel, having a distal end contactable in abutting relationship with said localization wire proximal tip, and having a metering proximal end extensible from said access port to an extent corresponding with the instantaneous position of said localization wire proximal tip within said auxiliary channel.

12. The apparatus of claim 2 in which:

said flexible metal wire is formed of steel and has a principal cross sectional dimension of between about 3 mils and 20 mils.

13. The apparatus of claim 1 including:

a precursor electrosurgical lancet electrode assembly mounted at said delivery cannula distal end, actuable to move between a retracted orientation non-interfering with said capture component during said extension, and a deployed orientation defining a generally linear cutting edge extending normally to said longitudinal axis;

wherein said deployment assembly includes a lancet electrode actuating assembly for actuating said lancet electrode assembly; and a precursor terminal assembly for effecting the conduction of electrical energy to said lancet electrode assembly.

14. The apparatus of claim 13 in which:

said lancet electrode assembly comprises a first resilient lancet wire having first distal end fixed to said delivery cannula forward region and moveable in compression against said first distal end, when actuated into said deployed orientation to define a first arch within a lancet plane and extending outwardly from said longitudinal axis.

15. The apparatus of claim 14 in which said lancet electrode assembly comprises a second resilient lancet wire having a second distal end fixed to said delivery cannula forward region and moveable in compression against said second distal end to define a second arch within said lancet plane extending outwardly from said longitudinal axis oppositely from said first lancet wire.

16. The apparatus of claim 1 in which:

said delivery cannula includes a precursor channel extending along said longitudinal axis to an exit port at said distal end;

including first and second electrosurgical lancet electrodes moveably mounted within said precursor channel and moveable when actuated, to deploy by extending from said exit port transversely from said longitudinal axis;

said deployment assembly includes a lancet electrodes actuating assembly for actuating said first and second electrosurgical lancet electrode; and including a precursor terminal assembly for effecting the conduction of electrical energy to said first and second lancet electrodes when deployed.

17. The apparatus of claim 16 in which:

said first and second lancet electrodes comprise respective first and second resilient electrode wires extending to respective first and second distal ends fixed to said delivery cannula forward region, each of said first and second resilient electrode wires being extendably moveable in compression, when actuated, from a retracted orientation into a deployed orientation to define respective first and second arches within a lancet plane and extending outwardly from said longitudinal axis.

18. The apparatus of claim 17 in which said lancet electrode actuating assembly is further actuable to retract said first and second resilient electrode wires from said deployed orientation to said retracted orientation.

19. The apparatus of claim 16 in which said first and second electrosurgical lancet electrodes comprise respective first and second resilient electrode wires prestressed to form respective outwardly curving first and second electrode surfaces within a lancet plane when actuated to deploy.

20. The apparatus of claim 19 in which:

said capture component forward portion includes a plurality of discrete elongate cage defining leafs having sides extending in parallel with said longitudinal axis to tip portions;

said tip portions incorporate apertures; and said electrically conducting electrosurgical leading edge portion includes at least two electrically conductive pursing cables extending through said apertures, coupled with said deployment assembly terminal assembly for excitation therefrom with electrosurgical cutting current and tensioned at said deployment assembly to effect said subsequent contraction by drawing said tip portions toward said longitudinal axis.

21. The apparatus of claim 1 in which:

said capture component forward portion includes a plurality of discrete elongate cage defining leafs having sides extending in parallel with said longitudinal axis to tip portions;

said tip portions incorporate apertures; and said electrically conducting electrosurgical leading edge portion includes at least two electrically conductive pursing cables extending through said apertures, coupled with said deployment assembly terminal assembly for excitation therefrom with electrosurgical cutting current and tensioned at said deployment assembly to effect said subsequent contraction by drawing said tip portions toward said longitudinal axis.

22. The apparatus of claim 21 in which the number of said pursing cables is equal to the number of said plurality of leafs.

23. The apparatus of claim 21 in which said deployment assembly effects said subsequent contraction of said leading edge portion by restraining movement of said pursing cables while effecting said movement of said capture component along said longitudinal axis.

24. The apparatus of claim 21 in which said deployment assembly effects said subsequent contraction of said leading edge portion by retracting said pursing cables.

25. The apparatus of claim 1 in which:

said capture component is slidably positioned within said delivery cannula interior channel and restrained therein along said longitudinal axis to exhibit a compressibly stressed initial state, said capture component leading edge including an electrically conductive cutting assembly and being elastically expandable toward an outer peripheral dimension selected for the circumscriptive engagement of said tissue volume peripheral extent upon releasing movement from said interior channel; and said deployment assembly is actuable to effect the expression of said capture component along said axis from said delivery cannula interior channel and to effect the elastic expansion of said capture component leading edge.

26. The apparatus of claim 25 in which said capture component is structured as an array of metal stems surmounting voids when expanding defining a truncated cone shape extending from said leading edge toward said distal end at the commencement of said expression from said delivery cannula.

27. The apparatus of claim 25 in which:

said delivery cannula forward region is cylindrically shaped when restrained and configured to elastically expand to exhibit a conical form when released from said restraint for movement; and said deployment assembly includes a confinement sleeve slideably mounted over said delivery cannula outer surface and movable from a forward position restraining said forward region to said cylindrical shape to a retracted position releasing said forward region for said elastic expansion.

28. The apparatus of claim 25 including:

a trocar component slideably mounted within said capture component when restrained within said delivery cannula interior channel, having a point portion extendible from said distal end and movable rearwardly to a retracted position; and said deployment assembly being drivably coupled with said trocar component to move it to said retracted position.

29. The apparatus of claim 25 in which said capture component is an open metal mesh structure stressed into a cylindrical shape when in said initial state.

30. The apparatus of claim 29 in which said capture component cutting assembly comprises spaced apart blades formed integrally with said metal mesh structure.

31. The apparatus of claim 25 in which said deployment assembly includes a pursing cable assembly engaged with said capture component leading edge and configured to draw said leading edge inwardly toward said longitudinal axis to effect an envelopment of said tissue volume with said capture component.

32. The apparatus of claim 25 in which said capture component, when expanded, is configured as a matrix of metal struts mutually spaced to define parallelogramic voids.

33. The apparatus of claim 32 in which:

said capture component leading edge includes a plurality of spaced apart eyelets; and said deployment assembly includes a pursing cable assembly engaged within said eyelets and configured to draw said leading edge inwardly toward said longitudinal axis to effect envelopment of said tissue volume.

34. A system for retrieving a tissue volume, comprising:

a source of electrical energy having an electrosurgical cutting output exhibiting a cutting voltage level and waveform for providing a cutting of tissue;

a delivery cannula having an outer surface surmounting an interior channel and extending from a proximal end portion along a longitudinal axis to a forward region, having a distal end positionable in confronting adjacency with said tissue volume;

a capture component positioned within said delivery cannula interior channel, having an expansible forward portion extending to a forwardly disposed, electrically conducting electrosurgical cutting leading edge portion and being expandable toward an outer peripheral dimension selected for circumscriptive engagement of said tissue volume when moved along said longitudinal axis to egress from said delivery cannula;

a deployment mechanism extending within said interior channel, drivably coupled with said capture component and actuable to effect said movement of said capture component along said longitudinal axis, and for effecting a subsequent contraction of said leading edge portion to effect closure movement of said capture component leading edge portion toward said longitudinal axis; and a control and support assembly coupled in supporting relationship with said delivery cannula at said proximal end portion for actuating said deployment mechanism and applying said electrosurgical cutting output to said capture component leading edge portion.

35. The system of claim 34 in which:

said capture component leading edge portion comprises a metal wire responsive to said electrosurgical cutting output to effect electrosurgical cutting of tissue during said movement and contraction.

36. The system of claim 34 in which:

said capture component forward portion is generally tubular, having a plurality of discrete elongate cage defining leafs therein having sides extending in parallel with said longitudinal axis to tip portions; and said deployment assembly includes a guidance assembly fixed to said delivery cannula adjacent said distal end and configured to effect deployment of said leafs into tissue at a predetermined angle of attack when said deployment assembly is actuated.

37. The system for claim 34 in which said guidance assembly is configured having a plurality of guidance slots, each configured for slidably receiving one of said discrete cage defining leafs and angularly oriented with respect to said longitudinal axis.

38. The system of claim 36 in which:

said capture component leading edge portion comprises a metal wire slideably connected to said tip portions of said leafs, expandable therewith when deployed into tissue, responsive to said conduction of electrical energy to effect electrosurgical cutting of tissue when said leafs are deployed into tissue.

39. The system of claim 38 in which:

said tip portions of said leafs incorporate apertures; and said metal wire extends in slideable relationship through said apertures and is formed as a component of a pursing cable assembly configured to draw said tip portions inwardly toward said longitudinal axis to effect said subsequent contraction of said leading edge; and said pursing cable is coupled with said deployment mechanism.

40. The system of claim 39 in which said capture component leafs are coupled in electrical communication with said terminal assembly and are configured to convey said electrosurgical cutting output applied from said control and support assembly to said flexible metal wire from said apertures.

41. The system of claim 34 in which:

said source of electrical energy is switchable to have a white coagulation output exhibiting a non-cutting voltage level less than said cutting voltage level; and said control and support assembly is actuable to switch said source to apply said white coagulation output to said capture component leading edge portion subsequent to applying said electrosurgical cutting output thereto.

42. The system of claim 34 in which:
said deployment assembly includes an electrically conductive forward component extending forwardly from said delivery cannula distal end; and
said control and support assembly is configured to electrically couple said forward component with said source as an electrical return.

43. The system of claim 34 in which:
an electrically conductive return electrode is located at said delivery cannula forward region; and
said control and support assembly is configured to electrically couple said return electrode with said source as an electrical return.

44. The system of claim 34 including:
an elongate auxiliary channel extending in parallel relationship with said longitudinal axis from an access port with said support assembly, through said interior channel to an exit opening at said delivery cannula distal end; and
an elongate sampling needle extendable through said auxiliary channel a length effective to engage said tissue volume in tissue sample removing relationship when said delivery cannula distal end is in confronting adjacency with said tissue volume.

45. The system of claim 34 including:
a support assembly coupled in supporting relationship with said delivery cannula at said proximal end portion; and
an elongate auxiliary channel extending in parallel relationship with said longitudinal axis from an access port within said support assembly, through said interior channel to an exit opening adjacent said axis at said delivery cannula distal end, said auxiliary channel being configured to slidably receive the proximal tip and shank of a lesion localization wire; and
a follower component slidably extending within said auxiliary channel, having a distal end contactable in abutting relationship with said localization wire proximal tip, and having a metering proximal end extensible from said access port to an extent corresponding with the instantaneous position of said localization wire proximal tip within said auxiliary channel.

46. The system of claim 34 in which:
said capture component forward portion includes a plurality of discrete elongate cage defining leafs having sides extending in parallel with said longitudinal axis to tip portions;
said tip portions incorporate apertures; and
said electrically conducting electrosurgical cutting leading edge portion includes at least two electrically conductive pursing cables extending through said apertures, coupled with said control and support assembly for excitation therefrom with said electrosurgical cutting outlet and tensioned by said deployment mechanism to effect said subsequent contraction by drawing said tip portions toward said longitudinal axis.

47. The system of claim 46 in which the number of said pursing cables is equal to the number of said plurality of leafs.

48. The system of claim 46 in which said deployment mechanism effects said subsequent contraction of said leading edge portion by restraining movement of said pursing cables while effecting said movement of said capture component along said longitudinal axis.

49. The system of claim 46 in which said deployment mechanism effects said subsequent contraction of said leading edge portion by retracting said pursing cables.

50. The system of claim 34 in which:
said capture component is restrained within said delivery cannula along said longitudinal axis to exhibit a compressibly stressed initial state, and being elastically expandable upon releasing movement from said interior channel toward said outer peripheral dimension.

51. The system of claim 50 including a trocar component slideably mounted within said internal channel, having a point portion extensible from said distal end when said delivery cannula distal end is positioned in said confronting adjacency with said tissue volume and movable rearwardly within said internal channel to a retracted position;
said deployment mechanism being drivably coupled with said trocar component and actuable to move said trocar component to said retracted position; and
said control and support assembly effects said actuation of said deployment mechanism to move said trocar component to said retracted position.

52. The system of claim 50 wherein:
said capture component is restrained to a cylindrical shape extending along said longitudinal axis within said delivery cannula interior channel from said leading edge to a driving edge when in said initial state; and
said deployment mechanism includes a drive tube mounted within said interior channel, engaged with said capture component driving edge and slideably movable forwardly to effect said releasing movement of said capture component.

53. The system of claim 50 in which:
said delivery cannula forward region extends rearwardly from said distal end and is configured to elastically expand outwardly to exhibit a conical form when released from a restrained condition; and
said deployment mechanism includes a confinement sleeve mounted over said delivery cannula outer surface and movable from a forward position retaining said forward region in said restrained condition to a retracted position releasing said forward region for said elastic expansion.

54. The system of claim 50 in which said capture component leading edge portion comprises spaced apart blades formed integrally with said metal mesh structure.

55. The system of claim 50 in which:
said capture component leading edge portion comprises a plurality of regularly spaced electrically conductive cutting blades;
the surfaces of said metal capture component are electrically insulated; and
said deployment mechanism initial actuation effects a rotation of said capture component to an extent wherein said cutting blades define a continuous cut locus.

56. The system of claim 50 in which said capture component is an open metal mesh structure stressed into a cylindrical shape when in said initial state.

57. The system of claim 56 in which said capture component cutting leading edge portion comprises spaced apart blades formed integrally with said metal mesh structure.

58. The system of claim 57 in which said deployment mechanism effects rotation of said capture component during said slideable movement outwardly from said forward region.

59. The system of claim 50 in which said deployment mechanism includes a pursing cable assembly engaged with said capture component leading edge portion and configured to draw said leading edge portion inwardly toward said longitudinal axis to effect an envelopment of said tissue volume with said capture component.

60. The system of claim 50 in which said capture component, when expanded, is configured as a matrix of metal struts mutually spaced to define parallelogramic voids.

61. The system of claim 50 in which:

said capture component leading edge portion includes a plurality of spaced apart eyelets; and said deployment mechanism includes a pursing cable assembly engaged within said eyelets and configured to draw said leading edge portion inwardly toward said longitudinal axis to effect envelopment of said target tissue volume.

62. The system of claim 50 in which:

said source of electrical energy comprises an electrosurgical generator controllable to provide a monopolar said output in electrical association with a remote return;

said cutting leading edge portion comprises a plurality of spaced electrically conductive cutting blades;

the surfaces of said capture component are electrically insulated; and said deployment mechanism effects rotation of said capture component during said movement.

63. The system of claim 62 in which:

said deployment mechanism includes a pursing cable assembly engaged with said capture component leading edge portion and configured to draw said leading edge portion inwardly toward said longitudinal axis to effect an envelopment of said targeted tissue volume with said capture component; and said control and support assembly effects application of said output to said cutting blades when said leading edge is drawn inwardly toward said longitudinal axis.

64. The system of claim 34 including:

a precursor electrosurgical lancet electrode assembly mounted at said delivery cannula distal end, actuable to move between a retracted orientation non-interfering with said capture component during said expansion, and a deployed orientation defining a generally linear cutting edge extending normally to said longitudinal axis;

a lancet electrode actuating assembly for actuating said lancet electrode assembly; and a lancet electrode control and support assembly for applying said electrosurgical cutting output to said lancet electrode assembly upon being actuated to said deployed orientation.

65. The system of claim 64 in which:

said lancet electrode assembly comprises a first resilient lancet wire having first distal end fixed to said delivery cannula forward region and moveable in compression against said first distal end, when actuated into said deployed orientation to define a first arch within a lancet plane and extending outwardly from said longitudinal axis.

66. The system of claim 65 in which said lancet electrode assembly comprises a second resilient lancet wire having a second distal end fixed to said delivery cannula forward region and moveable in compression against said second distal end to define a second arch within said lancet plane extending outwardly from said longitudinal axis oppositely from said first lancet wire.

67. The system of claim 34 in which:

said delivery cannula includes an auxiliary channel extending along said longitudinal axis to an exit port at said distal end;

including first and second electrosurgical lancet electrodes moveably mounted within said auxiliary channel and moveable when actuated, to deploy by extending from said exit port transversely from said longitudinal axis;

including a lancet electrode actuating assembly for actuating said first and second electrosurgical lancet electrodes; and a lancet electrode control and support assembly for applying said electrosurgical cutting output to said first and second electrosurgical lancet electrodes when deployed.

68. The system of claim 67 in which:

said first and second lancet electrodes comprise respective first and second resilient electrode wires extending to respective first and second distal ends fixed to said delivery cannula forward region, each of said first and second resilient electrode wires being extendably moveable in compression, when actuated, from a retracted orientation into a deployed orientation to define respective first and second arches within a lancet plane and extending outwardly from said longitudinal axis.

69. The system of claim 68 in which said lancet electrode actuating assembly is further actuable to retract said first and second resilient electrode wires from said deployed orientation to said retracted orientation.

70. The system of claim 67 in which said first and second electrosurgical lancet electrodes comprise respective first and second resilient electrode wires prestressed to form respective outwardly curving first and second electrode surfaces within a lancet plane when actuated to deploy.

71. The system of claim 34 in which:

said delivery cannula includes an elongate auxiliary channel extending along said longitudinal axis to a port at said distal end;

including first and second thin, resilient lancet electrodes slidably positioned within said auxiliary channel and restrained therein when in a retracted position and actuable to move within said channel through said port between said retracted position and a deployed orientation transversely disposed from said longitudinal axis defining first and second curved confronting electrode surfaces extending forwardly from said distal end within a common lancet plane; and including a lancet electrode deploying and retracting assembly for actuating said first and second lancet electrodes and applying said electrosurgical cutting output thereto.

72. The method for isolating and retrieving a targeted volume of tissue of predetermined peripheral extent situate within adjacent tissue of a patient, comprising the steps of:

(a) providing an electrosurgical generator controllable to derive an electrosurgical cutting output of predetermined cutting voltage level and an associated electrical return;

(b) providing a tissue isolation and retrieval instrument having a delivery cannula with an outer surface and an internal channel and extending from a proximal end portion along a longitudinal axis to a forward region extending inwardly from a distal end, said instrument having a capture component positioned within said delivery cannula interior channel, having an expansible forward portion extending to a forwardly disposed, electrically conducting electrosurgical cutting leading edge portion and being expandable toward an outer peripheral dimension selected to correspond at least with the dimension of said targeted tissue peripheral extent, said instrument having a deployment mechanism drivably coupled with said capture component for effecting said movement of said capture component along said longitudinal axis and for effecting a contraction of said leading edge portion toward said longitudinal axis;

(c) positioning said delivery cannula within said adjacent tissue with said distal end in confronting relationship with one side of said targeted volume of tissue peripheral extent;

(d) expressing said capture component forward portion from said delivery cannula forward region to effect expansion of said leading edge portion outwardly toward said outer peripheral dimension;

(e) when said leading edge portion approaches a side of said targeted tissue opposite said one side, effecting a said contraction of said leading edge portion;

(f) simultaneously with said steps (d) and (e), controlling said electrosurgical generator to apply said electrosurgical cutting output to said electrically conductive leading edge portion to create an incision within said adjacent tissue extending around, substantially enveloping, isolating and effecting a capturing of said targeted volume of tissue;

(g) controlling said electrosurgical generator to terminate said electrosurgical cutting output; and (h) removing said delivery cannula and capture component with said captured tissue from adjacency with said adjacent tissue.

73. The method of claim 72 wherein:

said step (b) provides said instrument with a support assembly for supporting said delivery cannula at said proximal end portion and said deployment mechanism and said instrument including an elongate auxiliary channel extending in generally parallel relationship with said longitudinal axis from an access port within said support assembly, through said interior channel to an exit opening at said delivery cannula distal end; and including the steps of:
   (i) providing an elongate sampling needle;
   (j) prior to said step (d), inserting said sampling needle into said access port, through said auxiliary channel, out of said exit opening and into said targeted volume of tissue;
   (k) drawing a sample from said targeted volume of tissue into said sampling needle; and
   (l) then removing said needle from said auxiliary channel.

74. The method of claim 72 wherein:

said step (a) provides a said electrosurgical generator having a white coagulation output exhibiting a non-cutting voltage level less than said cutting voltage level; and said step (h) is carried out while applying said white coagulation output to said capture component leading edge portion.

75. The method of claim 74 wherein:

said step (b) provides said instrument with an electrically conductive tissue parting pointed component extending forwardly from said delivery cannula distal end; and said steps (f) and (h) are carried out while simultaneously applying said electrical return to said tissue parting pointed component.

76. The method of claim 72 wherein:

said step (b) provides said instrument with an electrically conductive tissue parting pointed component extending forwardly from said delivery cannula distal end; and said step (f) is carried out while simultaneously applying said electrical return to said tissue parting pointed component.

77. The method of claim 74 in which:

said step (b) provides said instrument delivery cannula as having a return electrode at said forward region; and said steps (f) and (h) are carried out while simultaneously applying said electrical return to said return electrode.

78. The method of claim 72 in which:

said step (b) provides said instrument delivery cannula as having a return electrode at said forward region; and said step (f) is carried out while simultaneously applying said electrical return to said return electrode.

79. The method of claim 72 in which:

said step (b) provides said tissue isolation and retrieval instrument as having a said capture component leading edge portion comprising a metal wire; and said step (f) is carried out by applying said electrosurgical cutting output to said metal wire.

80. The method of claim 79 in which:

said step (b) provides said capture component forward portion as being generally tubular, having a plurality of discrete, elongate cage defining, leafs therein having sides extending in parallel with said longitudinal axis to tip portions, and said deployment mechanism is provided having a guidance assembly fixed to said delivery cannula and configured to effect deployment of said leafs at a predetermined angle of attack; and said step (d) is carried out by expressing said leafs through said guidance assembly at said angle of attack.

81. The method of claim 80 in which:

said step (b) provides said capture component tip portions of said leafs as incorporating apertures through which said metal wire slidably extends as a component of a pursing cable assembly; and said step (e) is carried out by tensioning said pursing cable assembly.

82. The method of claim 72 in which:

said step (b) provides said tissue isolation and retrieval instrument as having a said capture component restrained within said delivery cannula along said longitudinal axis to exhibit a compressibly stressed initial state and being elastically expandable upon releasing movement from said delivery cannula interior channel; and said step (d) expresses said capture component forward portion from said delivery cannula to effect said expansion.

83. The method of claim 82 in which:

said step (b) provides said capture component as an open metal mesh structure stressed into a cylindrical shape when in said initial state and said cutting leading edge portion comprises a plurality of electrically conductive cutting blades;

said step (d) includes the step of rotating said capture component to an extent wherein said cutting blades define a continuous cut locus.

84. The method of claim 83 in which:

said step (b) provides said deployment mechanism as including a pursing cable engaged with said capture component cutting leading edge portion and configured to draw said cutting leading edge portion inwardly toward said longitudinal axis when tensioned; and said step (e) includes the step of tensioning said pursing cable.

85. The method of claim 72 in which:

said step (b) includes the step of providing an electrosurgical lancet electrode having a tissue confronting electrode surface extending within a lancet plane;

said step (c) includes the steps:
   (c1) parting the epidermis of said patient with an incision at a location selected for an insertion of said delivery cannula forward region;
   (c2) positioning said lancet electrode confronting electrode surface upon said incision;
   (c3) simultaneously applying said electrosurgical cutting output to said lancet electrode and applying said electrical return to said patient at a location remote from said incision; and
   (c4) electrosurgically cutting an instrument access path with said tissue confronting electrode surface effective for positioning said delivery cannula within said adjacent tissue.

86. The method of claim 85 in which:

said step (b) provides said lancet electrode within said delivery cannula as having retracted and deployed orientations;

said step (c2) includes the step of deploying said electrosurgical lancet electrode from said retracted to said deployed orientation; and said step (c4) includes the step of retracting said electrosurgical lancet electrode subsequent to the cutting said instrument access path.

* * * * *